US012703108B2

(12) United States Patent
Cheng et al.

(10) Patent No.: US 12,703,108 B2
(45) Date of Patent: Aug. 11, 2026

(54) APPARATUS FOR FACILITATING AUTOMATED CONNECTION

(71) Applicant: Multiply Labs Inc., San Francisco, CA (US)

(72) Inventors: Christopher Jin Cheng, Castro Valley, CA (US); Jeffrey Ackerman Curhan, Warwick, RI (US); Roger Dean Lo, San Francisco, CA (US); Dorothy Szymkiewicz, San Francisco, CA (US)

(73) Assignee: Multiply Labs Inc., San Francisco, CA (US)

( * ) Notice: Subject to any disclaimer, the term of this patent is extended or adjusted under 35 U.S.C. 154(b) by 0 days.

(21) Appl. No.: 19/011,483

(22) Filed: Jan. 6, 2025

(65) Prior Publication Data

US 2025/0224059 A1 Jul. 10, 2025

Related U.S. Application Data

(60) Provisional application No. 63/698,008, filed on Sep. 23, 2024, provisional application No. 63/618,280, filed on Jan. 5, 2024.

(51) Int. Cl.
*B25J 15/04* (2006.01)
*C12M 1/00* (2006.01)
*C12M 1/36* (2006.01)
*C12M 3/00* (2006.01)
(Continued)

(52) U.S. Cl.
CPC .......... *B25J 15/0408* (2013.01); *C12M 23/38* (2013.01); *C12M 23/40* (2013.01); *C12M 23/42* (2013.01); *C12M 23/44* (2013.01); *C12M 23/46* (2013.01); *C12M 23/48* (2013.01); *C12M 29/04* (2013.01); *C12M 29/06* (2013.01); *C12M 41/48* (2013.01); *F16L 37/084* (2013.01); *G01N 35/0099* (2013.01)

(58) Field of Classification Search
CPC ... F16L 37/084; F16L 37/1225; F16L 41/001; A61M 2039/1027; A61M 2039/2072; A61M 39/20
See application file for complete search history.

(56) References Cited

U.S. PATENT DOCUMENTS 5,413,147 A * 5/1995 Moreiras ............. F16L 25/0036
9,770,579 B1 * 9/2017 Narciso-Martinez ........................ A61M 39/02
12,171,975 B1 * 12/2024 Tomita .................. A61M 39/18

* cited by examiner

*Primary Examiner* — Zachary T Dragicevich
(74) *Attorney, Agent, or Firm* — Morgan, Lewis & Bockius LLP

(57) ABSTRACT

An apparatus includes a port body for holding a first device and a retainer for retaining the port body. The port body includes a base, a stem extending from the base, and one or more first anti-rotation members disposed at the base. The retainer includes first and second retaining members, with the base of the port body disclosed in between. A through-hole larger than the stem of the port body is formed at the first retaining member, allowing the stem to pass through and to move relative to the first retaining member. One or more second anti-rotation members are disposed at the first or second retaining member and coupled with the one or more first anti-rotation members. The retainer restricts the port body from rotating but allows it to move translationally relative to the retainer to accommodate axial misalignment when connecting the first device with a second device.

30 Claims, 49 Drawing Sheets

(51) Int. Cl.

| | |
|---|---|
| ***F16L 37/084*** | (2006.01) |
| ***G01N 35/00*** | (2006.01) |

100

200

310

320

500

100-1

900
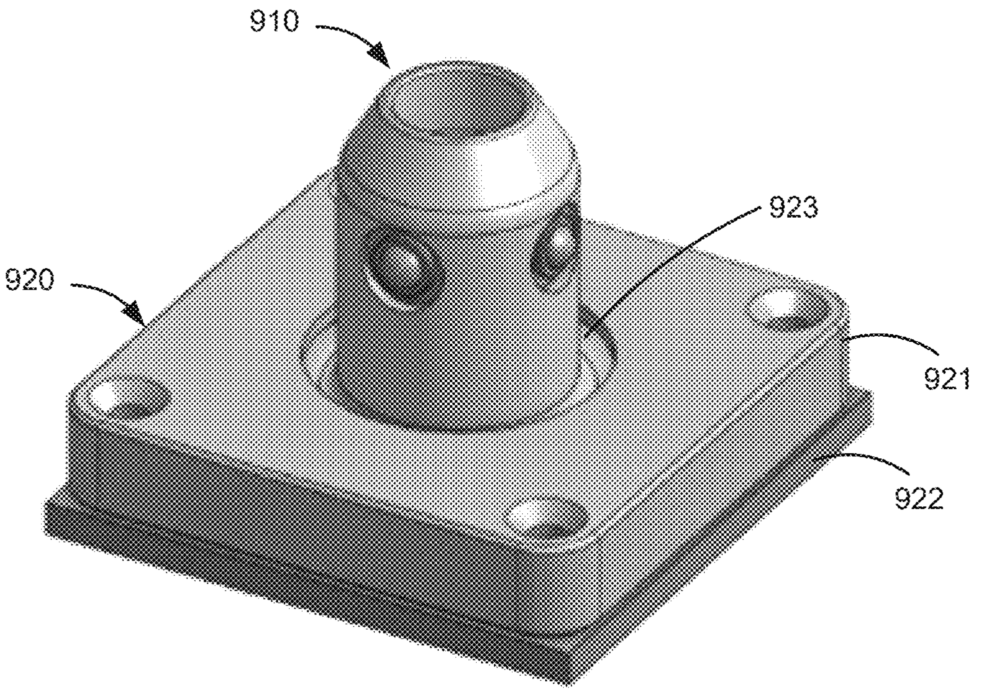
Figure 9A
910
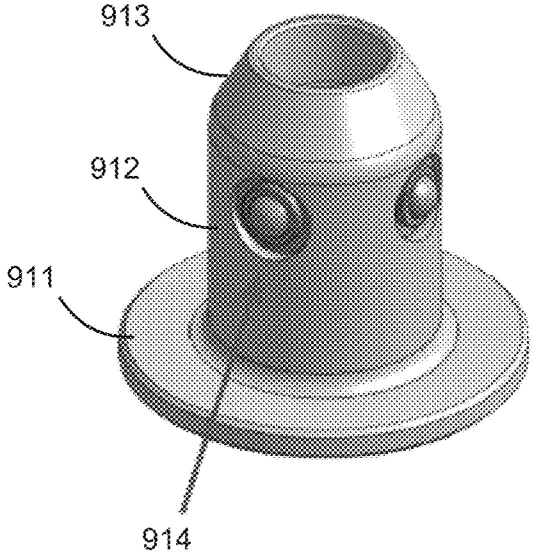
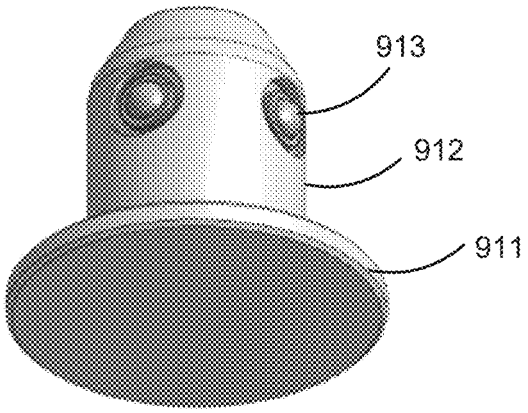
Figure 9B Figure 9C

1030

1050

1100

1200

APPARATUS FOR FACILITATING AUTOMATED CONNECTION

CROSS-REFERENCE TO RELATED APPLICATION

The present application claims priority to U.S. Provisional Patent Application No. 63/618,280 filed Jan. 5, 2024, and U.S. Provisional Patent Application No. 63/698,008 filed Sep. 23, 2024, each of which is hereby incorporated by reference in its entirety for all purposes.

TECHNICAL FIELD

The present disclosure generally relates to devices, systems and methods for facilitating automated manufacturing at a biological foundry, and in particular to apparatuses for facilitating automated connections and the like.

BACKGROUND

Cell therapies are next-generation drugs where live cells are used to treat a subject. This is in contrast with traditional small-molecule and biologic drugs, where small or large molecules—but not whole living cells—are used to treat patients. Many of the most recent and promising innovations in medicine are represented by cell therapies in which the cells of a subject (either the patient or a donor) are extracted, genetically engineered in a lab, grown in an incubator, and finally infused in the patient in order to achieve a therapeutic effect. However, despite the life-saving effects of many cell therapies, there are significant bottlenecks to their widespread adoption. For instance, one obstacle is represented by the current limits in manufacturing capacity for cell therapies. Conventional cell therapy production processes are still largely labor-based and inefficient.

Traditionally, cell therapies are produced with labor-intensive processes. These conventional processes require not only a large number of manufacturing operators, but also the employment of highly skilled (and expensive) technicians. These constraints make it particularly difficult to manufacture cell therapies at an industrial scale. Cell therapy manufacturing processes are low-scale and labor-intensive because they were originally developed in the context of academic research. The original lab processes—which were developed to demonstrate the feasibility of cell therapies—were then hastily modified and retrofitted in order to fulfill regulatory requirements and achieve good manufacturing practices.

This conventional approach allowed drug manufacturers to bring to the market the first approved cell therapies. However, this labor-intensive, lab-oriented approach is unsuitable to achieve industrial scale. At their core, current cell manufacturing processes were designed to be manually completed by highly trained personnel—such as the researchers that conduct scientific experiments in an academic environment. Requiring this type of skillset becomes a disadvantage in an industrial setting. Cell manufacturing processes depend on highly trained, highly educated manual labor, and this makes them incompatible with the efficiency of mass-manufacturing industrial processes.

The dominant conventional approach to cell manufacturing is based on a set of separate individual pieces of manufacturing equipment placed on a clean room bench. This manufacturing process still looks exactly like a research laboratory, where all the machinery is manually operated and directly supervised by highly skilled operators. In order to execute the cell manufacturing processes, these skilled operators gown up, enter a clean room, and manually activate the machines. The operators also transfer the batch material from machine to machine, manually sample the batches to perform quality control testing, ensure that reagents are delivered to the cells, and ensure that waste material is removed. This labor-based conventional approach is very different from the organization of industrial-scale processes, where most tasks are autonomously executed by specialized machinery, which is supervised by ordinary manufacturing technicians (not engineers, nor scientists).

As such, the conventional labor-based approach to cell therapy manufacturing has at least three fundamental limits. First, the conventional approach is not scalable and not robust to operator variability. Because the conventional approach is extremely labor-intensive, cell therapy manufacturing is limited to small-scale applications. Increasing throughput beyond a few hundred products per year has proven extremely difficult, because such an effort would require hiring, training, retaining, and managing a large number of highly skilled, expensive operators. Moreover, labor-based processes are typically unable to reach industrial scale, and cell manufacturing is not an exception. This pronounced reliance of labor presents additional disadvantages, including the fact that—because of operator variability—the yield and the features of the finished cell therapy product are hard to predict and to control. This operator variability makes scaling the process of manufacturing cell therapy products even harder—particularly in terms of margins, in which a higher number of rejected batches increases the cost per batch.

Additionally, the conventional approach to manufacturing cell therapy products is inefficient. Since individual machines for the cell therapy manufacturing process are utilized in series (e.g., the machines are used one at a time, with a single batch manually moved from a piece of machinery to the next), when a machine is active all the others are idle. This results in a low utilization rate for all machines, since most of the machines are waiting for the batch to arrive, while a single machine is being used. The problem of a very low utilization rate is particularly evident for cell manufacturing processes, which are characterized by machines with markedly different cycle times. More specifically, systems like bioreactors process a single batch for weeks, while machines like thawing and freezing systems are only used for a few hours on a single batch. This results in utilization rates that are even lower for the faster machines—because the slower machines are the bottleneck and limit the rate of the rest of the serial process.

Finally, the conventional approach to manufacturing cell therapy products has low throughput. Because the process is managed and executed by human operators, only one batch can be produced at any given time on a serial production line. For instance, if two batches were manufactured at the same time on the same production line, in fact, there would be high risk of cross-contamination or of mix-up errors by the operators. Since all the serial machines are used for just one product at a time, the resulting throughput of the production line is extremely low. As a reference, typically a cell therapy product takes two to three weeks to be manufactured. This means that, in order to avoid mix-ups, a whole production line must be reserved for a single product for about half of a month—a rate that is incompatible with industrial scale. Because of this temporal constraint, a whole manufacturing suite (typically consisting of about 1,000 square feet of clean room space) must be reserved for a single serial production line. Therefore, the only way to increase throughput via this conventional approach is by creating facilities with multiple independent suites that replicate the same process. However, each suite can only handle one product at a time, occupies significant clean room space, and is entirely operated by skilled labor. As such, this conventional approach is not scalable, and not suitable to manufacture more than a few hundreds of cell therapies per year—with very high production costs.

One solution to this conventional approach are closed system cell therapy machines that have been developed to attempt to address the shortcomings of the traditional approach. However, even this solution is still labor-intensive and inadequate to reach industrial scale. For instance, this solution can be described as an end-to-end serial system that is contained into a single machine. Different parts of the same machine perform the different steps of the production process. In other words, a single piece of equipment contains all the sub-systems that are needed to perform the cell manufacturing process. An intricate set of tubes connects all of these systems, so that the cell therapy product (which is typically in liquid form) can be transferred from one subsystem to the next without being exposed to the external environment, which provides the closed system.

However, these end-to-end, closed systems are sold as a unique piece of machinery. As such, the machinery cannot be modified by the buyer: once a system is bought, the buyer is constrained to run the exact process for which that machine was designed. Additionally, the machinery still needs to be operated by a highly skilled technician, who needs to perform a complicated set of actions to set up, monitor, and manage the manufacturing process. More specifically, highly trained operators set up the intricate network of tubes that is required by each batch. These operators are also tasked with opening and closing the valves that regulate the flow of material from one part of the system to the next. Furthermore, technicians also manually sample the batch, whenever testing is needed for quality control.

As such, this prior closed system solution suffers disadvantages, in that the closed system solution is overcomplicated. Setting up dozens of tubes, liquid reservoir bags, and reagents requires highly trained labor. This setting up process also takes a long time—even for a skilled technician—to set up, operate, and supervise the machinery. This results in the need for a number of operators that increases proportionally to the number of production system—making it impossible to achieve industrial scale and contain manufacturing costs.

Furthermore, the prior closed system solution is inefficient. Since the architecture of the closed system is still serial, this approach suffers of the same efficiency constraints as the dominant (bench-based) approach. At any given time, most of the subsystems inside of the end-to-end machine are unused. This happens because only one system can be used at a time—this is a serial production line with the hard limit of a single product per production run. Moreover, since some parts of the process are particularly slow (for example, the expansion of the cells into a bioreactor), the subsystems are characterized by an even lower utilization rate than the slower subsystems of the machinery.

Additionally, this closed system lacks design flexibility. This inflexibility drawback is typical of closed systems that are built specifically to execute a particular process. Once the machinery is bought, it is not possible to replace an outdated subsystem with a better one (for example, a subsystem that performs a task better, or with a higher throughput). Any modification to the original closed system machinery requires massive engineering and retooling costs, comparable to building a whole new end-to-end system from scratch. This lack of flexibility is particularly disadvantageous in the case of cell therapy manufacturing—where processes are often tuned and improvement at all stages of clinical development.

Moreover, since each closed system is end-to-end and can only manufacture a single product at a time, the only way to increase throughput is to buy more of these closed systems. This in turn worsens the above-mentioned complexity and underutilization problems. In other words, deploying more complex systems increases the need for skilled operators, which in turn increases the cost of manufacturing. Since each machine is largely underutilized (only one subsystem is active at any given time), chronic underutilization also characterizes a facility that is equipped with multiple end-to-end systems.

Additionally, a major problem of labor-based cell manufacturing processes is that human operators need to sample each batch manually. In cell manufacturing processes, sterility must be always ensured. This is particularly important, because cell therapies cannot be sterilized at the end of the manufacturing process (that would kill the cells). At the same time, guaranteeing the quality of cell manufacturing processes requires a large number of quality control steps. And, in order to perform quality control tests, the cell therapy products must be frequently sampled (e.g., a part of the product must be removed from the batch, while ensuring the sterility of both the sample and the product). In conventional cell manufacturing processes, sampling tasks are executed by human operators.

One disadvantage of this conventional approach to sampling is that human operators are a significant potential source of contamination for cell therapy products. Every time a batch is sampled manually, there is a high risk of contamination because the operator must manually remove a part of the liquid containing the cell product. Even semi-automated sampling procedures, where an operator activates a system that performs the sampling task, present significant risk of contamination due to requiring the presence of a human technicians in close proximity to the process.

Another critical issue is that sampling procedures are performed extremely frequently in cell manufacturing processes. Cell therapy products are sometimes sampled multiple times during a single day. Since cell manufacturing processes have a long completion time (most require more than a week, and many can take up to fifteen to twenty days), manual sampling is repeated dozens of times for every single batch. Repeating risky sampling procedures with this extreme frequency greatly increases the risk of contamination.

Given the above background, there is a need in the art for improved systems, methods, and apparatuses for facilitating an improved manufacture of cell therapies that addresses these dilemmas.

The information disclosed in this background section is only for enhancement of understanding of the general background of the invention and should not be taken as an acknowledgement or any form of suggestion that this information forms the prior art already known to a person skilled in the art.

SUMMARY

To address the shortcomings discussed above and/or other issues, the present disclosure provides apparatuses that include a floating non-rotating design compatible with a variety of fluid and non-fluid connectors and incorporate an external lead-in feature for the mating coupler. One of the key innovations of such apparatuses is the combination of the port body shape which has a tip (e.g., a large chamfered tip) to engage with a mating coupler and corresponding size multi-directional planar float of the port body that accommodates axial misalignment but resists torsional loads typically associated with a threaded connector. The port body is designed to house fluid, gas, and electrical connectors effectively converting an array of industry standard connectors into robotic compatible connectors due to the external mating feature and position tolerance compensation via the floating design (e.g., movable) of the port body. The present disclosure also provides apparatuses that include a dual function design with external drive and alignment features and internal features for compatibility with a variety of fluid and non-fluid connectors. One of the key innovations of such apparatuses is the dual function aspect of the design that can convert a variety of industry standard connectors into robot-grippable-robot-drivable (twist) connectors with specific features to accommodate axial misalignment during mating with the corresponding port. The present disclosure further provides robotic end of arm tools (EOATs) that include novel robotic grasp and rotate mechanisms. In some embodiments, a robotic EOAT includes the combination of axial grasping with position control along the rotation axis, and the simultaneous ability to rotate the grasped part (e.g., a coupler) via a friction drive wheel against the exterior of the part (hold and rotate the part while the EOAT body remains stationary). As such, the apparatuses of the present disclosure advantageously leverage advanced robotic features and technologies while retaining the benefits of conventional devices. This enables the transformation of cellular engineering target manufacturing from labor-based and low-throughput processes to fully industrialized, high-throughput processes with high scale, efficiency and repeatability.

In various embodiments, the present disclosure provides an apparatus for facilitating automated connection of a first device and a second device. The apparatus includes a port body and a retainer. The port body includes a base, a stem, a bore, a tip and one or more first anti-rotation members. The stem extends from the base. The bore extends from an upper end portion of the stem to a lower end portion of the base and configured for receiving at least a portion of the first device. The tip is disposed at a free end portion of the stem and configured for guiding the second device when connecting the second device and the first device. The one or more first anti-rotation members are disposed at the base. The retainer includes a first retaining member, a second retaining member, a first circular or substantially circular through-hole, and one or more second anti-rotation members. The first retaining member has a first surface. The second retaining member is coupled or formed with the first retaining member and has a second surface spaced apart from the first surface of the first retaining member in an axial direction of the port body. In some such embodiments, the base of the port body is disposed between the first surface of the first retaining member and the second surface of the second retaining member. The first circular or substantially circular through-hole is disposed on the first retaining member and has a diameter larger or substantially larger than an outer diameter of the stem to allow the stem of the port body to pass through and to move relative to the first retaining member. The one or more second anti-rotation members are disposed at the first retaining member or the second retaining member and coupled with the one or more first anti-rotation members to restrict the port body from rotating relative to the retainer. As such, while restricted from rotating relative to the retainer, the port body is movable translationally relative to the retainer in a plane substantially perpendicular to the axial direction of the port body.

In an exemplary embodiment, the base is circular.

In another exemplary embodiment, the base is non-circular.

In some embodiments, the base is substantially planar.

In some such embodiments, a thickness of the base equals or substantially equals a distance between the first surface of the first retaining member and the second surface of the second retaining member.

In some embodiments, the first device includes a fluid connector, a gas connector, an electrical connector, or any combination thereof.

In some embodiments, the second device includes a corresponding fluid connector, a corresponding gas connector, a corresponding electrical connector, or any combination thereof.

In some embodiments, at least a portion of the stem is circular or substantially circular.

In some embodiments, the port body further includes a plurality of internal ribs disposed on an inner surface of the stem and distributed circumferentially. In some such embodiments, each internal rib in the plurality of internal ribs includes a surface for abutting an external wall of the first device to secure the first device with the port body.

In some embodiments, each internal rib in at least a subset of the plurality of internal ribs includes a first rib portion disposed at or adjacent the free end portion of the stem, and a second rib portion disposed between the free end portion of the stem and the base.

In some such embodiments, the second rib portion contacts with a knurled surface of the first device.

In some embodiments, the stem includes a first stem member and a second stem member removably coupled with each other.

In some such embodiments, at least one internal rib in the plurality of internal ribs is formed on each of the first stem member and the second stem member.

In some embodiments, the first stem member and the second stem member are coupled with each other by snap-fit.

In an exemplary embodiment, the first stem member includes a plurality of internal recesses formed on the first stem member, and the second stem member includes a plurality of protrusions, each snap-fitted into a corresponding internal recess in the plurality of internal recesses formed on the first stem member.

In some embodiments, the first stem member is monolithically formed with the base as a single piece.

In some embodiments, the second stem member includes an upper portion, and at least a segment of the upper portion is inserted into a groove of the first device, thereby helping to secure the first device on the port body and restrict the first device from moving axially relative to the port body.

In some embodiments, the second retaining member is a component of another device.

In some embodiments, a second circular or substantially circular through-hole is formed on the second retaining member and concentric with the first circular or substantially circular through-hole formed on the first retaining member.

In some such embodiments, one or more slots are formed at the second retaining member, each extending from the second circular or substantially circular through-hole to an edge of the second retaining member to accommodate tubing or cable.

In some embodiments, each of the one or more first anti-rotation members is formed adjacent to an outer edge of the base.

In an exemplary embodiment, each of the one or more first anti-rotation members is a pin formed on the base. Each of the one or more second anti-rotation members is a hole formed on the second retaining member to receive a corresponding pin formed on the base. A size of the hole is larger than a size of the corresponding pin.

In some embodiments, the retainer further includes a rim formed on the first surface of the first retaining member or the second surface of the second retaining member to set a boundary for translational movement of the port body.

In some embodiments, the port body is movable translationally relative to the retainer in the plane substantially perpendicular to the axial direction of the port body within a range defined by (i) a gap between the first circular or substantially circular through-hole formed on the first retaining member and the stem, (ii) a gap between each respective first anti-rotation member in the one or more first anti-rotation members and a corresponding second anti-rotation member in the one or more second anti-rotation members, (iii) a gap between the rim formed on the first surface of the first retaining member or the second surface of the second retaining member and an outer edge of the base of the port body, or (iv) a combination thereof.

In some embodiments, the rim is formed on the second surface of the second retaining member.

In an exemplary embodiment, the rim includes one or more rim segments.

In another exemplary embodiment, the rim is in a closed form shape surrounding the base.

In various embodiments, the present disclosure provides an apparatus for facilitating automated connection of a first device and a second device. The apparatus includes a port body and a retainer. The port body a base, a stem, a bore, and a tip. The a stem extends from the base, and at least a portion of the stem includes a circular or substantially circular cross-section. The bore extends from an upper end portion of the stem to a lower end portion of the base, and configured for receiving at least a portion of the first device. The tip is disposed at a free end portion of the stem and configured for guiding the second device when connecting the second device and the first device. The retainer includes a first retaining member, a second retaining member, a first circular or substantially circular through-hole, and a rim. The first retaining member has a first surface. The second retaining member is coupled with the first retaining member and has a second surface spaced apart from the first surface of the first retaining member in an axial direction of the port body. In some such embodiments, the base of the port body is disposed between the first surface of the first retaining member and the second surface of the second retaining member. The first circular or substantially circular through-hole is formed on the first retaining member and has a diameter larger than an outer diameter of the stem to allow the stem of the port body to pass through and to move relative to the first retaining member. The rim is formed on the first surface of the first retaining member or the second surface of the second retaining member to set a boundary for translational movement of the port body. The port body is movable translationally relative to the retainer in a plane substantially perpendicular to the axial direction of the port body within a range defined by (i) a gap between the first circular or substantially circular through-hole formed on the first retaining member and the stem, (ii) a gap between the rim formed on the first surface of the first retaining member or the second surface of the second retaining member and an outer edge of the base of the port body, or (iii) a combination thereof.

In various embodiments, the present disclosure provides an apparatus for facilitating automated connection of a first device and a second device. The apparatus includes a port body and a retainer. The port body includes a base, a stem, a bore, a tip, and a plurality of internal ribs. The stem extends from the base and includes a first stem member and a second stem member removably coupled with each other. The bore extends from an upper end portion of the stem to a lower end portion of the base and configured for receiving at least a portion of the first device. The tipis disposed at a free end portion of the stem and configured for guiding the second device when connecting the second device and the first device. The plurality of internal ribs is formed on the stem and distributed circumferentially for abutting an external wall of the first device to secure the first device with the port body, In some such embodiments, (i) at least one internal rib in the plurality of internal ribs is formed on each of the first stem member and the second stem member, and (ii) each internal rib in at least a subset of the plurality of internal ribs includes a first rib portion disposed at or adjacent the free end portion of the stem and a second rib portion disposed between the free end portion of the stem and the base. The retainer is coupled with the port body and configured to restrict the port body from rotating relative to the retainer but allow the port body to move translationally relative to the retainer in a plane substantially perpendicular to the axial direction of the port body.

In some embodiments, the first stem member is monolithically formed with the base as a single piece.

In various embodiments, the present disclosure provides an automation-compatible apparatus including a first coupling member and a second coupling member. The first coupling member includes a first side wall defining a first bore that receives at least a portion of a first device. The second coupling member is connected to or formed with the first coupling member at a proximal end portion of the first coupling member. The second coupling member includes a second side wall having an exterior surface defined by revolving a continuous curve about a rotational axis of the apparatus to facilitate operation by a robotic arm. In some such embodiments, the revolving exterior surface includes a first revolving segment proximal to the first coupling member and a second revolving segment distal to the first coupling member. Each of the first and second revolving segments of the revolving exterior surface has a first side and a second side that is narrower than the first side, and the second sides of the first and second revolving segments of the revolving exterior surface face each other.

In some embodiments, the first device includes a fluid connector, a gas connector, an electrical connector, or any combination thereof.

In some embodiments, the first coupling member is connected to the first device by a retainer.

In an exemplary embodiment, the retainer is a component of the first device.

In some embodiments, the retainer is a clip having an open side to allow the clip to fit on the first coupling member.

In some embodiments, the first coupling member includes a first external recess and a second external recess formed on the first side wall at or adjacent a distal end portion of the first coupling member. The clip includes an upper wall, an outer side wall, a first clip protrusion, and a second clip protrusion. The upper wall is configured for abutting a surface of the distal end portion of the first coupling member and a surface of the first device to restrict the first device from moving relative to the first coupling member in the rotational axis of the apparatus. In some embodiments, the upper wall includes an outer curved edge. The outer side wall extends downward from at least a portion of the outer curved edge of the upper wall and includes a first clip end and a second clip end at the open side of the clip. The first clip protrusion protrudes inward from the outer side wall at or adjacent to the first clip end for engaging with the first external recess formed on the first side wall. The second clip protrusion protrudes inward from the outer side wall at or adjacent to the second clip end for engaging with the second external recess formed on the first side wall.

In an exemplary embodiment, each of the first and second external recesses is a circumferential groove.

In some embodiments, the upper wall of the clip further includes an inner curved edge. The clip further includes an inner side wall extending upward from at least a portion of the inner curved edge of the upper wall to assist in retaining the first device.

In some embodiments, the first coupling member includes a plurality of first internal ribs formed on the first side wall and distributed circumferentially around the rotational axis of the apparatus for abutting an external side wall of the first device to restrict the first device from rotating relative to the first coupling member around the rotational axis of the apparatus.

In some embodiments, the first coupling member includes one or more external strengthening members formed on the first side wall thereof.

In some such embodiments, the one or more external strengthening members include one or more external rims, one or more external ribs, or any combination thereof.

In some embodiments, the first coupling member includes an external flange at or adjacent the proximal end portion thereof, and the second coupling member includes a shoulder at or adjacent the proximal end portion thereof to hold the external flange of the first coupling member.

In an exemplary embodiment, the external flange of the first coupling member and the shoulder of the second coupling member are connected to each other by ultrasonic welding.

In some embodiments, the proximal end portion of the first coupling member is inserted into the proximal end portion of the second coupling member.

In some such embodiments, the proximal end portion of the first coupling member includes a plurality of first external ribs formed on the first side wall and distributed circumferentially around the rotational axis of the apparatus for abutting the proximal end portion of the second coupling member to assist in securing the first coupling member with the second coupling member.

In some embodiments, the first and second revolving segments of the revolving exterior surface are substantially the same in size and shape.

In an exemplary embodiment, one of the first and second revolving segments of the revolving exterior surface is a conical or substantially conical surface, and the other of the first and second revolving segments of the revolving exterior surface is an inverted conical or substantially conical surface.

In some embodiments, the revolving exterior surface further includes a third revolving segment between the first and second revolving segments and connecting the second side of the first revolving segment with the second side of the second revolving segment.

In an exemplary embodiment, the third revolving segment of revolving exterior surface is a cylindrical or substantially cylindrical surface.

In some embodiments, the second side wall of the second coupling member defines a second bore to receive at least a portion of a second device.

In some embodiments, the second device includes a port body.

In some embodiments, the port body is a floating port body.

In some embodiments, the second coupling member includes an internal chamfer formed at a second end portion of the second coupling member to guide connection of the apparatus with the second device.

In some such embodiments, the internal chamfer is formed collectively by a plurality of second internal ribs on the second side wall and distributed circumferentially around the rotational axis of the apparatus.

In an exemplary embodiment, the second coupling member has a substantially uniform wall thickness.

In some embodiments, a tapered internal recess is formed circumferentially on the second side wall of the second coupling member at or adjacent the internal chamfer to facilitate smooth interaction between the apparatus and the second device.

In various embodiments, the present invention provides an automation-compatible apparatus including a rotational axis, a first coupling member, a second coupling member and a clip. The first coupling member and the second coupling member are connected to or formed with each other at proximal end portions thereof. The first coupling member includes a first side wall defining a first bore to receive at least a portion of the first device. The first coupling member also includes a first external recess and a second external recess formed on the first side wall at or adjacent a distal end portion of the first coupling member. The second coupling member includes a revolving exterior surface around the rotational axis of the apparatus to facilitate operation by a robotic arm. The clip has an open side to allow the clip to fit on the first coupling member. The clip includes an upper wall, an outer side wall, a first clip protrusion, and a second clip protrusion. The upper wall is configured for abutting a surface of the distal end portion of the first coupling member and a surface of the first device to restrict the first device from moving relative to the first coupling member in the rotational axis of the apparatus. The upper wall includes an outer curved edge. The outer side wall extends downward from at least a portion of the outer curved edge of the upper wall and includes a first clip end and a second clip end at the open side of the clip. The first clip protrusion protrudes inward from the outer side wall at or adjacent to the first clip end for engaging with the first external recess formed on the first side wall. The second clip protrusion protrudes inward from the outer side wall at or adjacent to the second clip end for engaging with the second external recess formed on the first side wall.

In some embodiments, the first coupling member includes a plurality of first internal ribs formed on the first side wall and distributed circumferentially around the rotational axis of the apparatus for abutting an external side wall of the first device to restrict the first device from rotating relative to the first coupling member around the rotational axis of the apparatus.

In various embodiments, the present disclosure provides an automation-compatible apparatus including a rotational axis, a first coupling member, and a second coupling member. The first coupling member is configured for connecting the first device to the apparatus. The second coupling member is connected to or formed with the first coupling member. The second coupling member includes a bore, a revolving exterior surface around the rotational axis of the apparatus, an internal chamfer, and a tapered internal recess. The bore is configured to receive at least a portion of a device. The revolving exterior surface is configured to facilitate operation by a robotic arm. The internal chamfer is formed at or adjacent an end portion distal to the first coupling member and configured for guiding connection of the apparatus with the device. The tapered internal recess is formed circumferentially on an interior surface of the second coupling member at or adjacent the internal chamfer to facilitate smooth interaction between the apparatus and the device.

The methods and apparatuses of the present disclosure have other features and advantages which will be apparent from or are set forth in more detail in the accompanying drawings, which are incorporated herein, and the following Detailed Description, which together serve to explain certain principles of the present invention.

BRIEF DESCRIPTION OF THE DRAWINGS

FIG. 9A is a perspective view illustrating an exemplary apparatus in accordance with some exemplary embodiments of the present disclosure.

FIG. 9B is a perspective view illustrating an exemplary port body in accordance with some exemplary embodiments of the present disclosure.

FIG. 9C is another perspective view illustrating the exemplary port body of FIG. 9B.

Figure 1A:
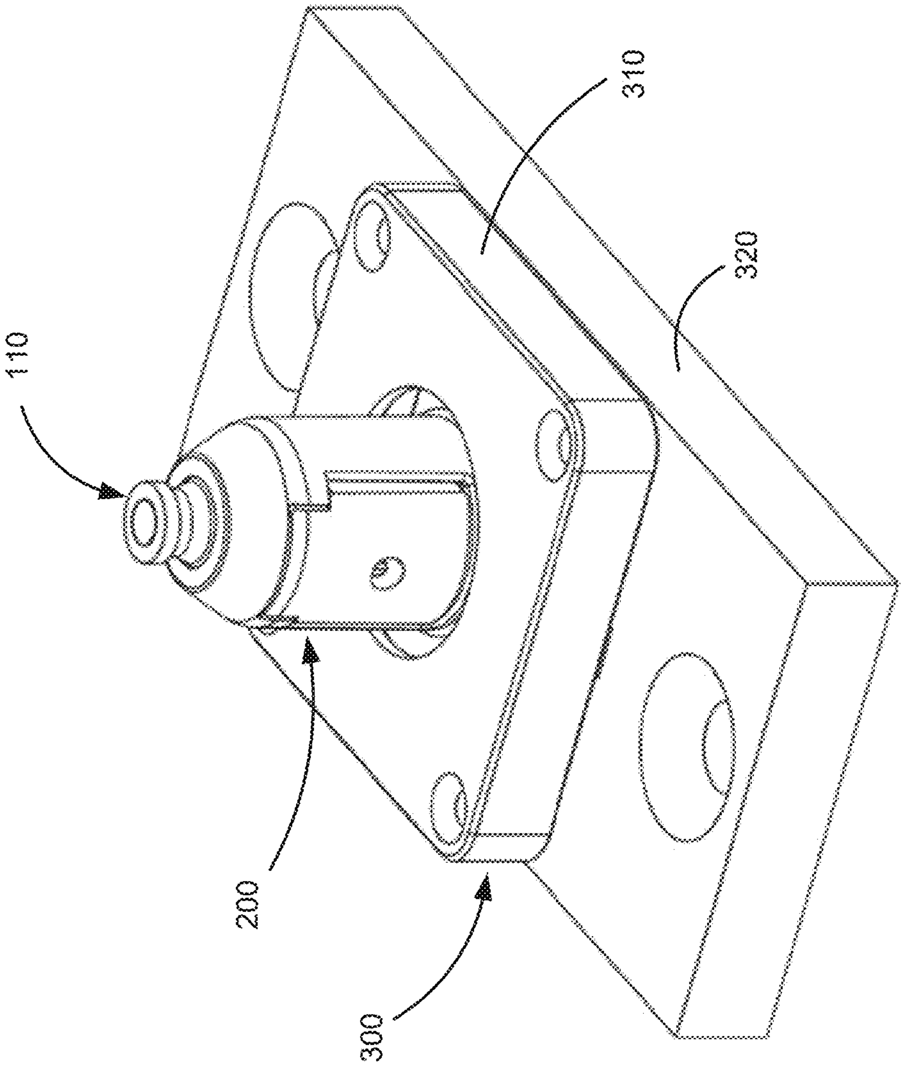
FIG. 1A is a perspective view illustrating an exemplary apparatus (also referred herein as a port assembly) in accordance with some exemplary embodiments of the present disclosure.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

In some embodiments, the present disclosure provides apparatuses that include a floating, non-rotating, or minimally rotating, design compatible with a variety of fluid and non-fluid connectors and incorporate an external lead-in feature for the mating coupler. One of the key innovations of such apparatuses is the combination of the port body shape which has a tip (e.g., a large, chamfered end portion) to engage with a mating coupler and corresponding size multi-directional planar float of the port body that accommodates axial misalignment but resists torsional loads typically associated with a threaded connector. In some embodiments, the port body is designed to house fluid, gas, and electrical connectors effectively converting an array of industry standard connectors into robotic compatible connectors due to the external mating feature and position tolerance compensation via the floating design (e.g., movable) of the port body. In some embodiments, the present disclosure also provides apparatuses that include a dual function design with external drive and alignment features and internal features for compatibility with a variety of fluid and non-fluid connectors. One of the key innovations of such apparatuses is the dual function aspect of the design that can convert a variety of industry standard connectors into robot-graspable-robot-drivable (twist) connectors with specific features to accommodate axial misalignment during mating with the corresponding port. In some embodiments, the present disclosure further provides robotic end of arm tools (EOATs) that include novel robotic grasp and rotate mechanisms. In some embodiments, a robotic EOAT includes the combination of axial grasping with position control along the rotation axis, and the simultaneous ability to rotate the grasped part (e.g., a coupler) via a friction drive wheel against the exterior of the part (hold and rotate the part while the EOAT body remains stationary). As such, the apparatuses of the present disclosure advantageously leverage advanced robotic features and technologies while retaining the benefits of conventional devices. This enables the transformation of cellular engineering target manufacturing from labor-based and low-throughput processes to fully industrialized, high-throughput processes with high scale, efficiency and repeatability.

Reference will now be made in detail to various embodiments of the present disclosure, examples of which are illustrated in the accompanying drawing and described below. While the disclosure will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the present invention as defined by the appended claims.

It will also be understood that, although the terms first, second, etc. may be used herein to describe various elements, these elements should not be limited by these terms. These terms are only used to distinguish one element from another. For example, a first instrument could be termed a second instrument, and, similarly, a second instrument could be termed a first instrument, without departing from the scope of the present disclosure. The first instrument and the second instrument are both instruments, but they are not the same instrument.

The terminology used in the present disclosure is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and or "comprising," when used in this specification, specify the presence of stated features, integers, steps, operations, elements, and or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Furthermore, when a reference number is given an "$i^{th}$" denotation, the reference number refers to a generic component, set, or embodiment. For instance, an application termed "application i" refers to the $i^{th}$ application in a plurality of applications.

The term "about" or "approximately" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

For purposes of explanation, the description herein has been described with reference to specific implementations. However, the illustrative discussions are not intended to be exhaustive or to limit the implementations to the precise forms disclosed. Many modifications and variations are possible in view of the above teachings. The implementations are chosen and described in order to best explain the principles and their practical applications, to thereby enable others skilled in the art to best utilize the implementations and various implementations with various modifications as are suited to the particular use contemplated.

In the interest of clarity, not all of the routine features of the implementations described herein are shown and described. It will be appreciated that, in the development of any such actual implementation, numerous implementation-specific decisions are made in order to achieve the designer's specific goals, such as compliance with use case- and business-related constraints, and that these specific goals will vary from one implementation to another and from one designer to another. Moreover, it will be appreciated that such a design effort might be complex and time-consuming, but nevertheless be a routine undertaking of engineering for those of ordering skill in the art having the benefit of the present disclosure.

Figure 1B:
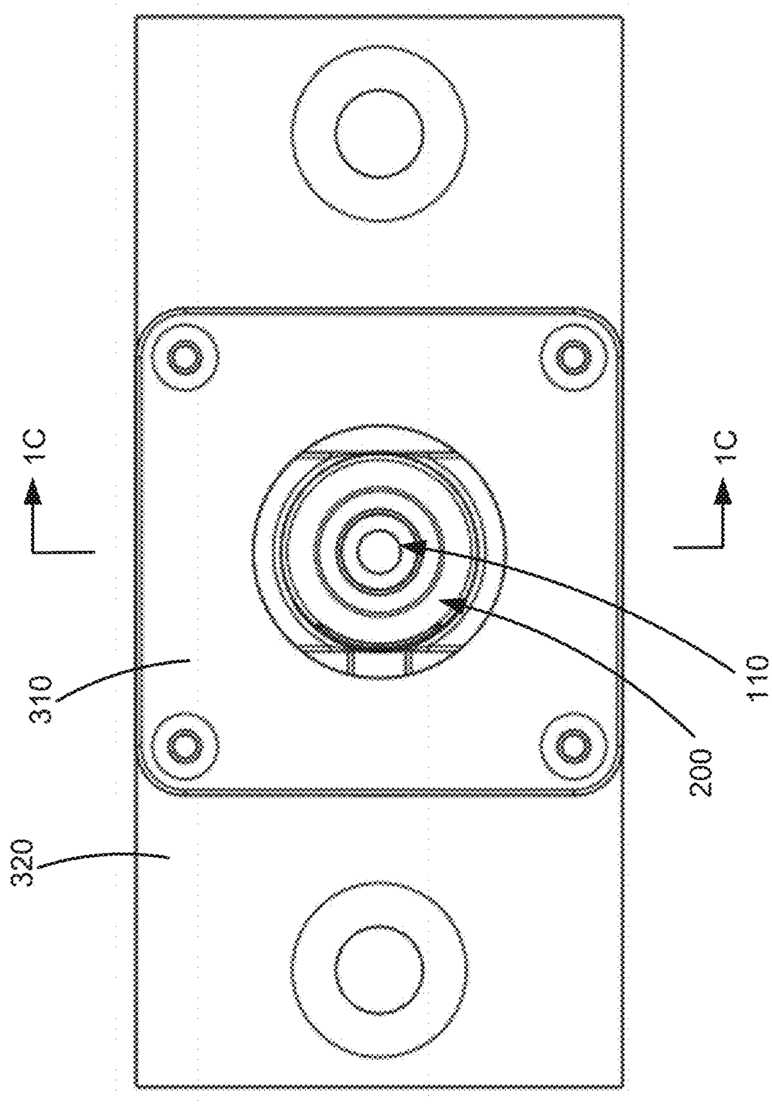
FIG. 1B is a top view illustrating the exemplary apparatus of FIG. 1A.
Figure 1C:
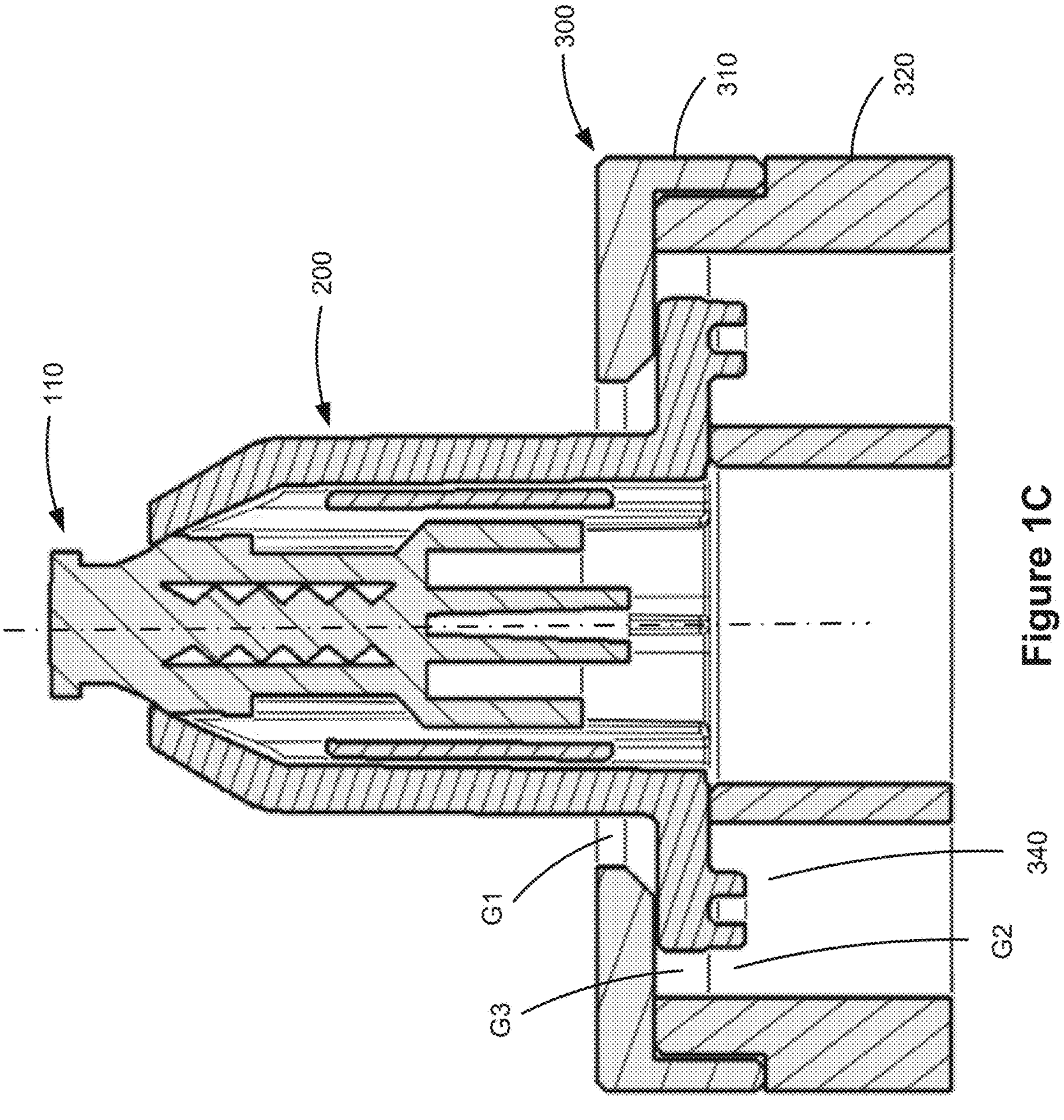
FIG. 1C is a cross-sectional view taken along line 1C-1C of FIG. 1B.

Referring to FIGS. 1A-1C, there is depicted an exemplary apparatus, generally designated 100, in accordance with some exemplary embodiments of the present disclosure. In various embodiments, the apparatus includes a floating non-rotating design that is compatible with a variety of fluid and non-fluid connectors and incorporates an external lead-in feature for the mating coupler. Accordingly, the apparatus is also referred herein as a port assembly, a port, or a floating port. One of the key innovations is the combination of the port body shape which has a tip (e.g., a chamfered end portion) to engage with a mating coupler and corresponding size multi-directional planar float of the port body that accommodates axial misalignment but resists torsional loads typically associated with a threaded connector. The port body is designed to house fluid, gas, and electrical connectors effectively converting an array of industry standard connectors into robotic compatible connectors due to the external mating feature and position tolerance compensation via the floating design (e.g., movable) of the port body. In some embodiments, the apparatus is configured for accommodating axial misalignment during mating with a device or a component of a device.

In some embodiments, the apparatus 100 includes a port body, such as a port body 200, and a retainer, such as a retainer 300. In some embodiments, the port body and the retainer are coupled to each other. In some embodiments, the port body is configured to hold a first device (e.g., a connector), such as a first device 110. In some embodiments, the retainer is configured to restrict the port body from rotating relative to the retainer but allow the port body to move translationally relative to the retainer in a plane substantially perpendicular to an axial direction of the port body. Accordingly, the retainer restricts the first device, which is held by the port body, from rotating relative to the retainer but allows the first device to move translationally relative to the retainer in the plane substantially perpendicular to the axial direction of the port body. Advantageously, this can accommodate axial misalignment when connecting the first device with a second device while constraining its rotation so that connection of the first and second devices can be made by twisting.

Figure 2B:
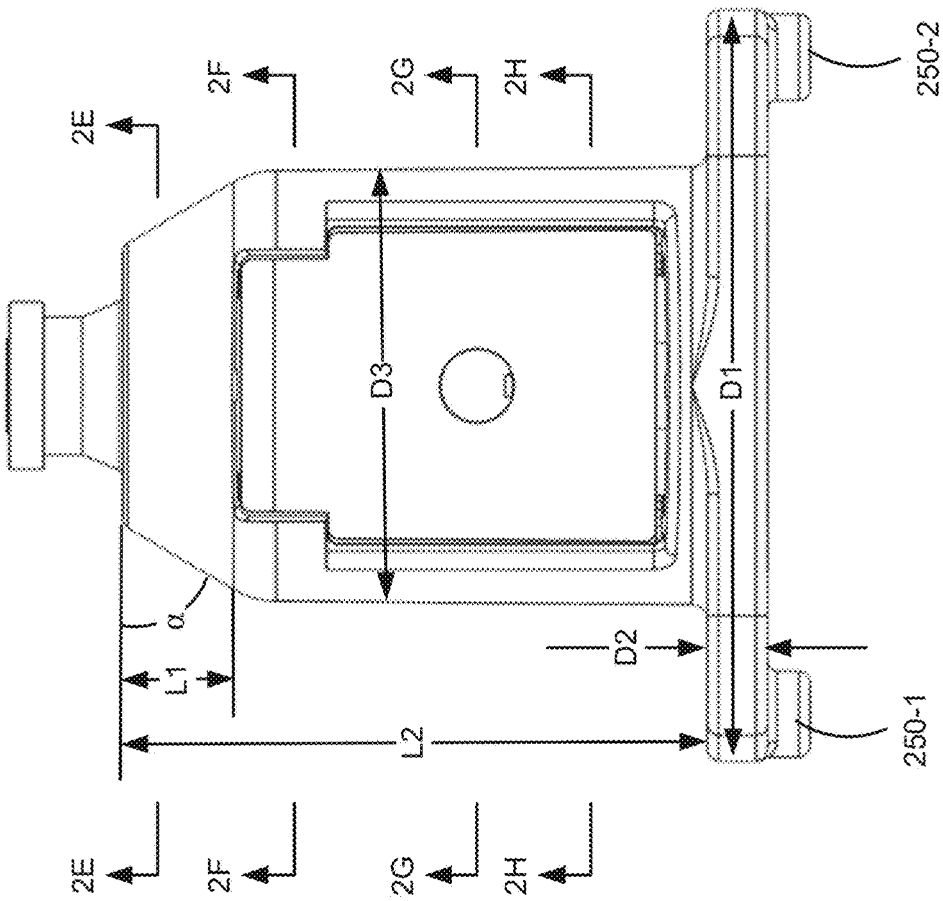
FIG. 2B is a front view illustrating the exemplary port body of FIG. 2A.
Figure 2A:
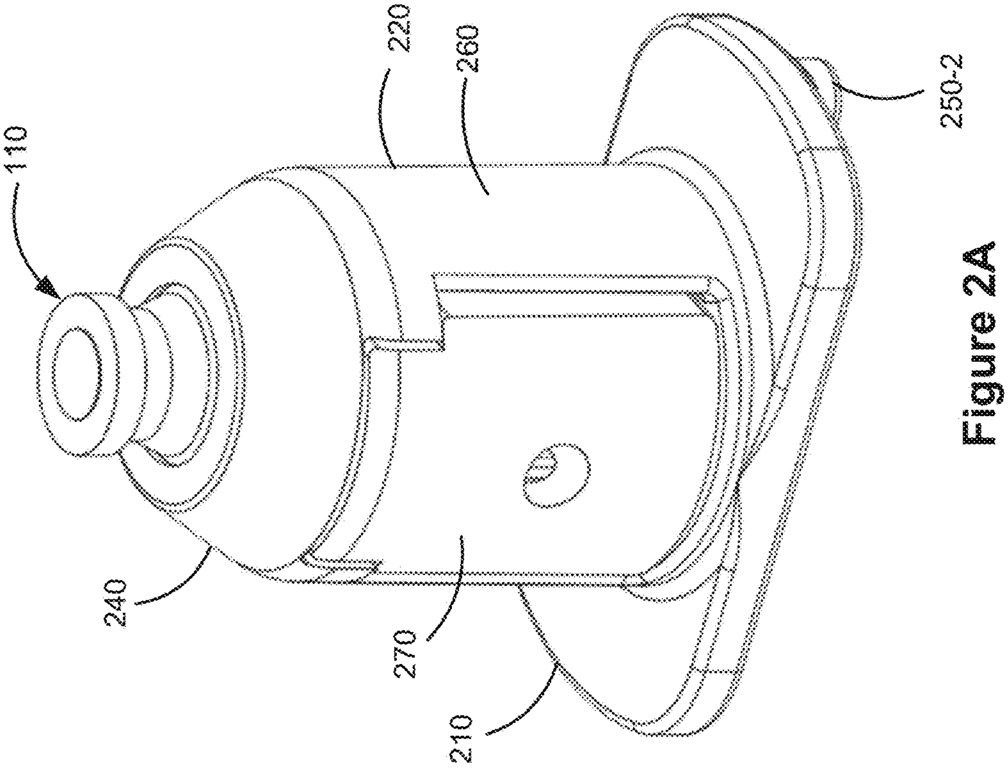
FIG. 2A is a perspective view illustrating an exemplary port body in accordance with some exemplary embodiments of the present disclosure.
Figure 2C:
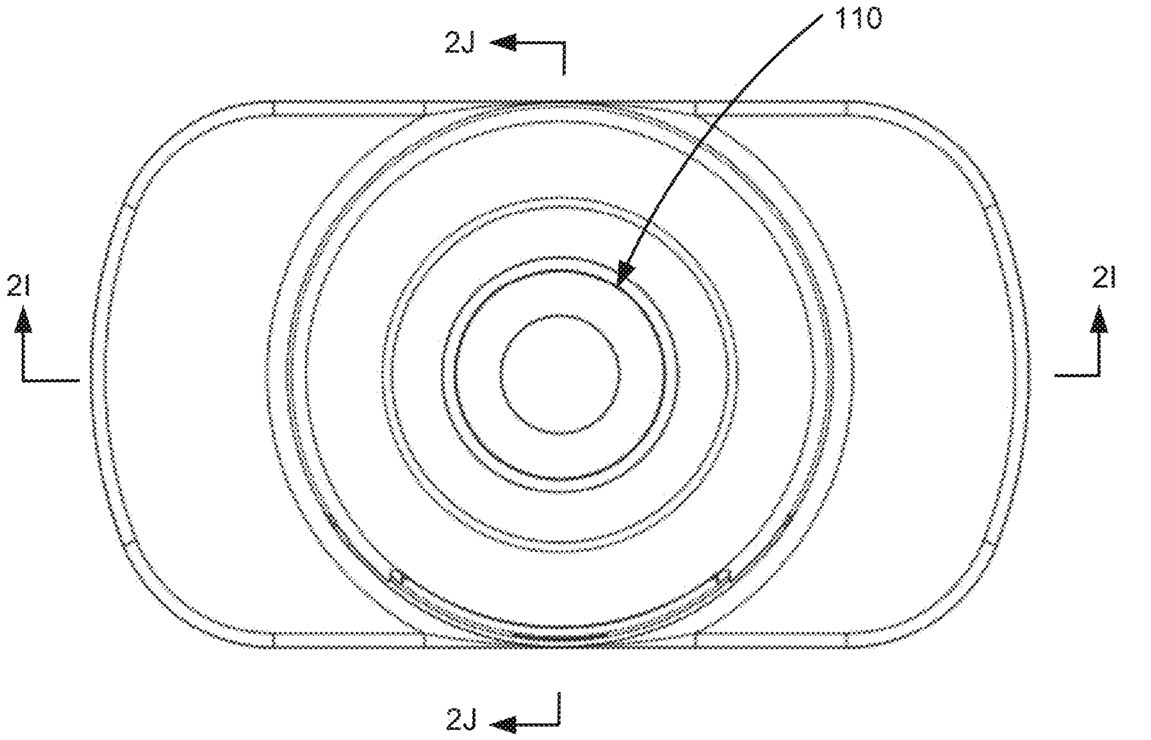
FIG. 2C is a top view illustrating the exemplary port body of FIG. 2A.
Figure 2D:
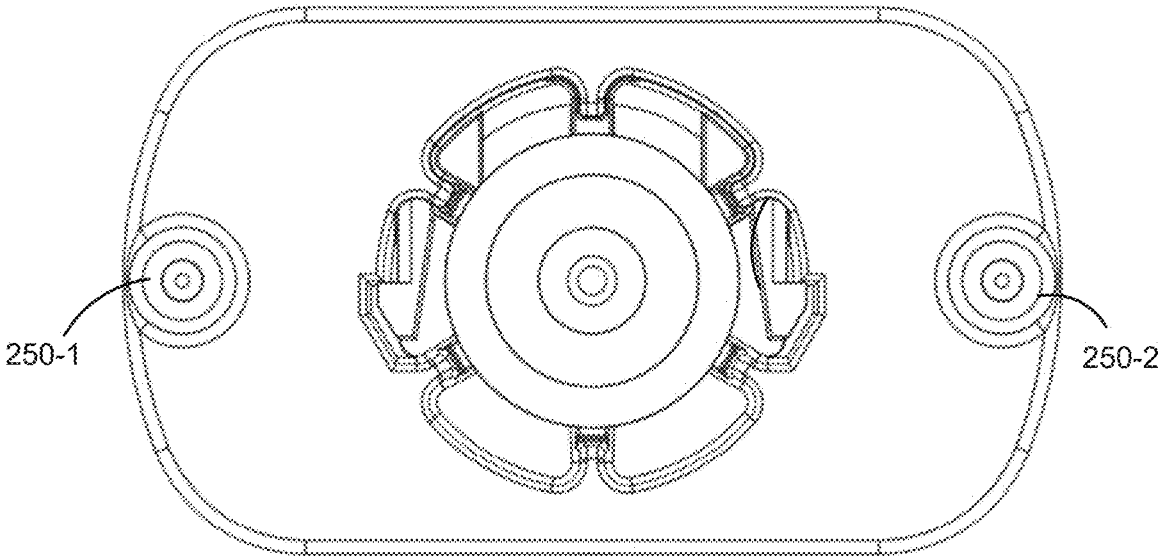
FIG. 2D is a bottom view illustrating the exemplary port body of FIG. 2A.
Figure 2E:
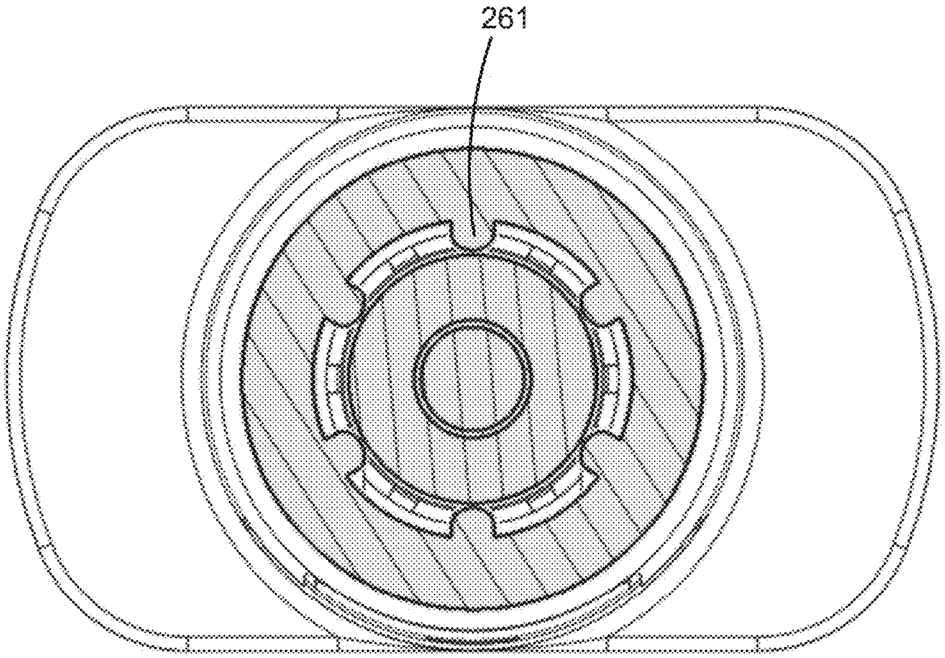
FIG. 2E is a cross-sectional view taken along line 2E-2E of FIG. 2B.
Figure 2F:
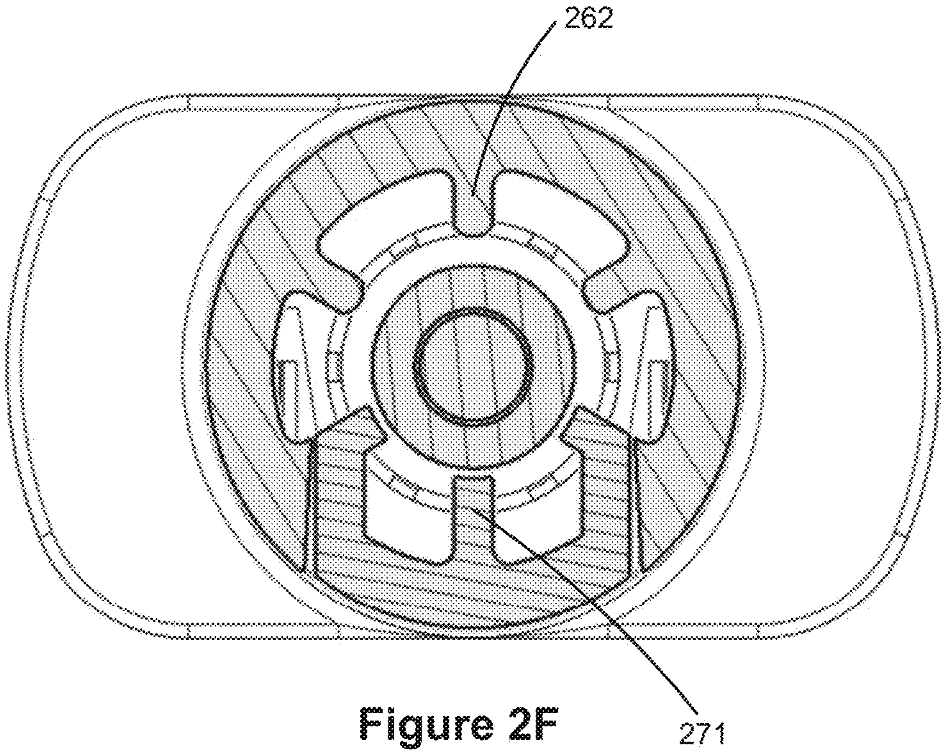
FIG. 2F is a cross-sectional view taken along line 2F-2F of FIG. 2B.
Figure 2G:
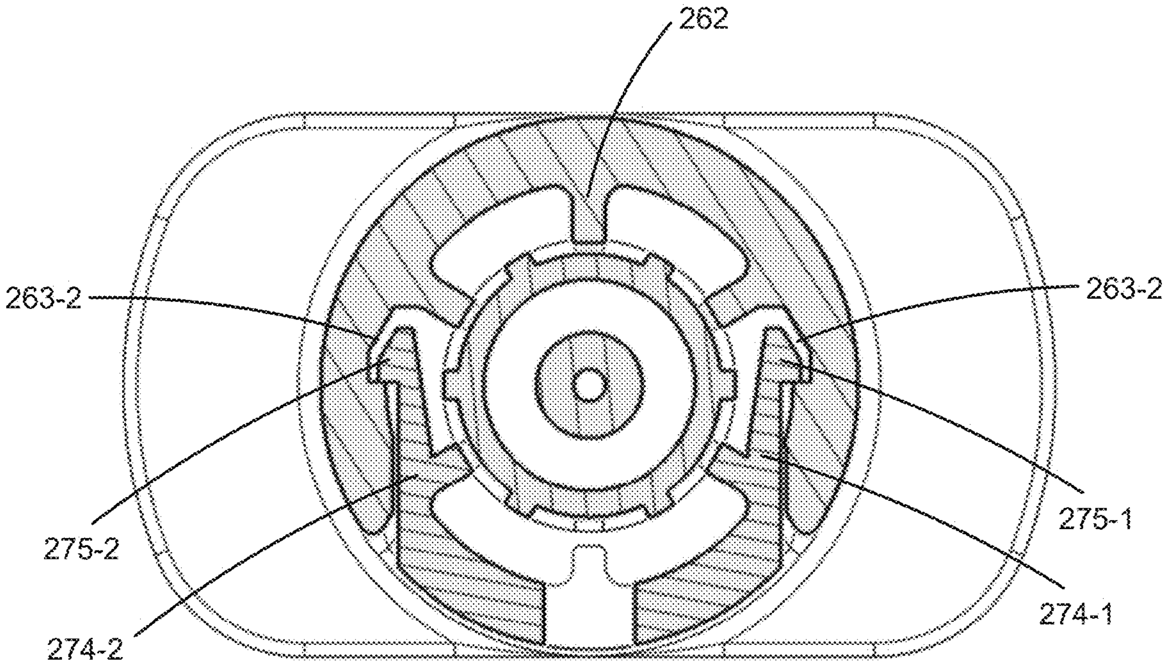
FIG. 2G is a cross-sectional view taken along line 2G-2G of FIG. 2B.
Figure 2H:
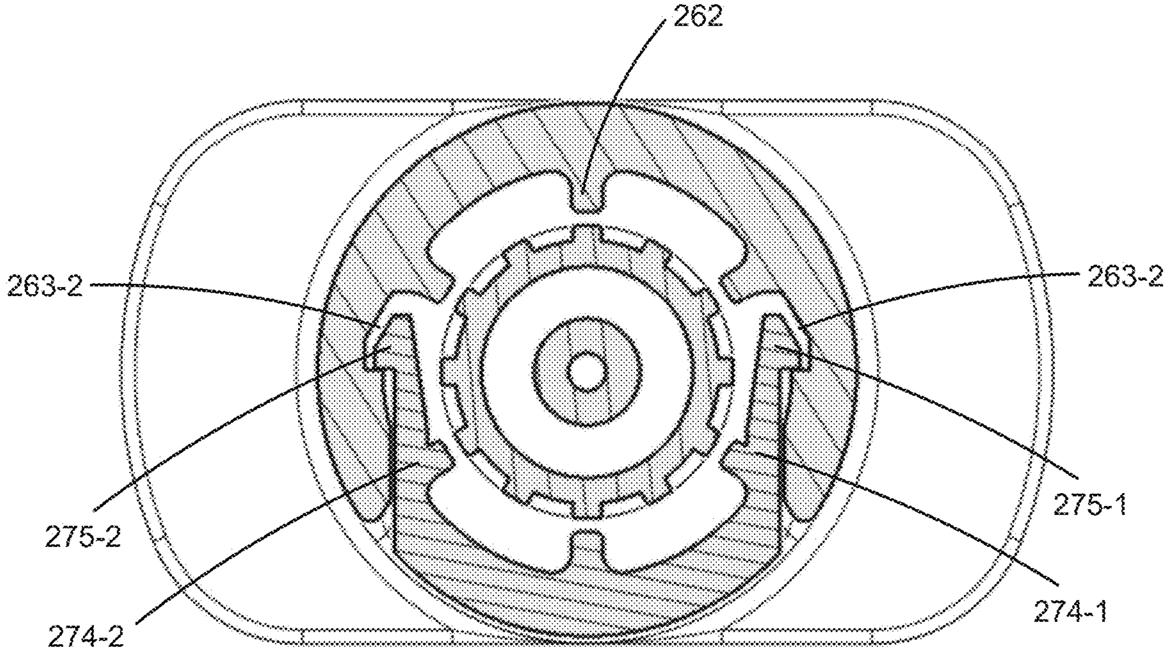
FIG. 2H is a cross-sectional view taken along line 2H-2H of FIG. 2B.
Figure 2J:
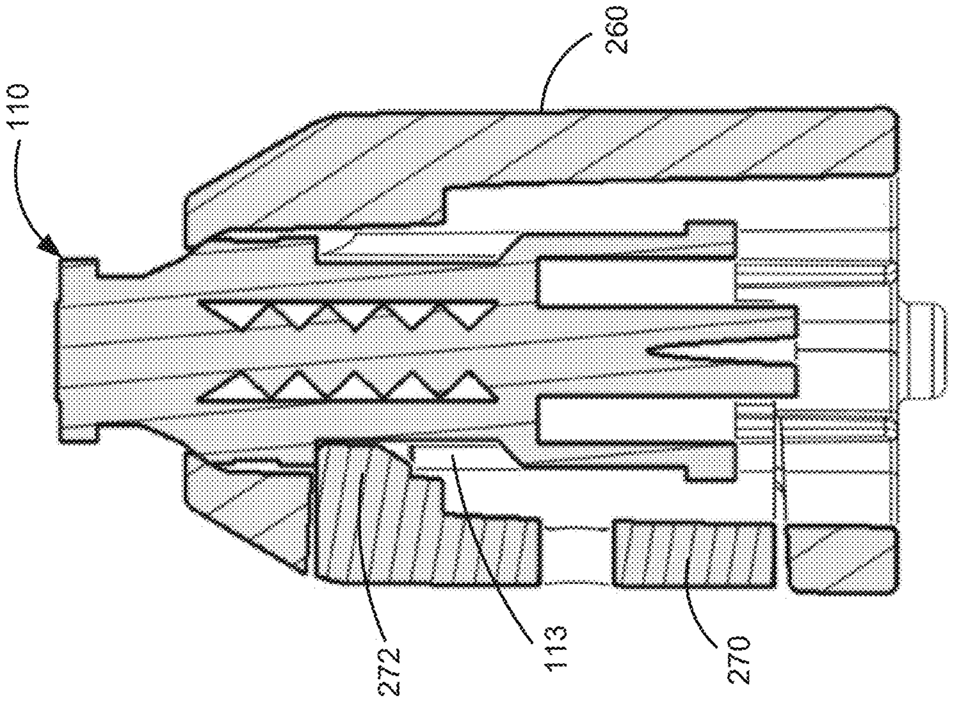
FIG. 2J is a cross-sectional view taken along line 2J-2J of FIG. 2C.
Figure 2I:
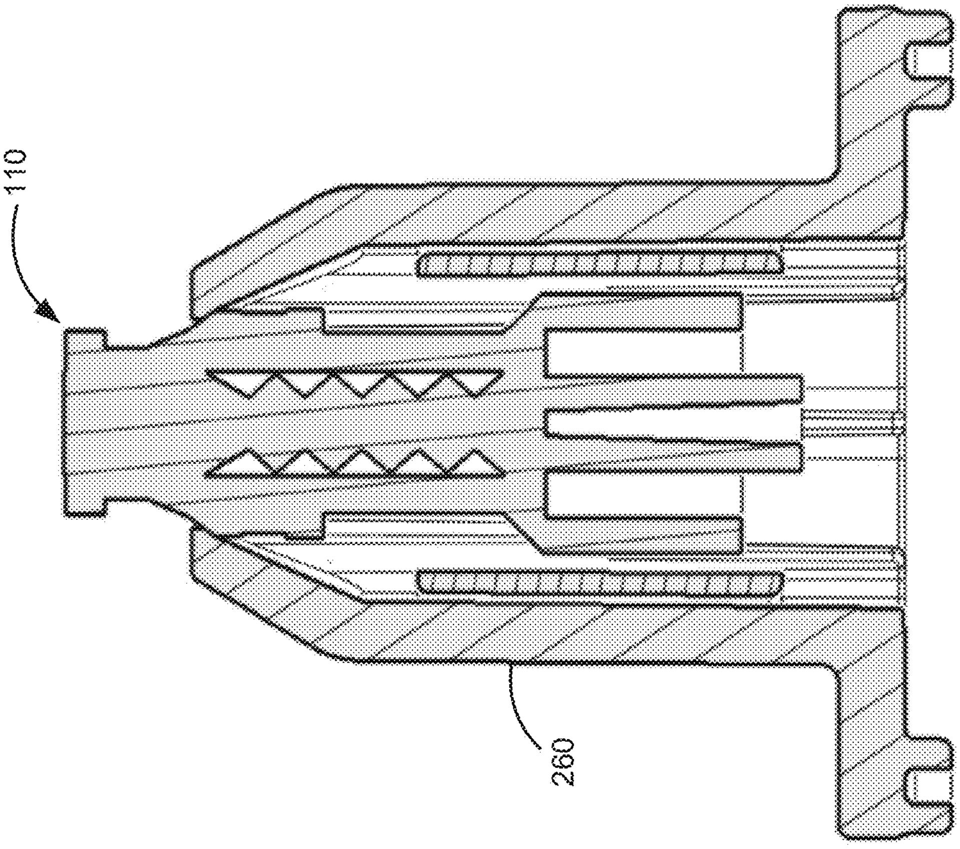
FIG. 2I is a cross-sectional view taken along line 2I-2I of FIG. 2C.
Figure 2M:
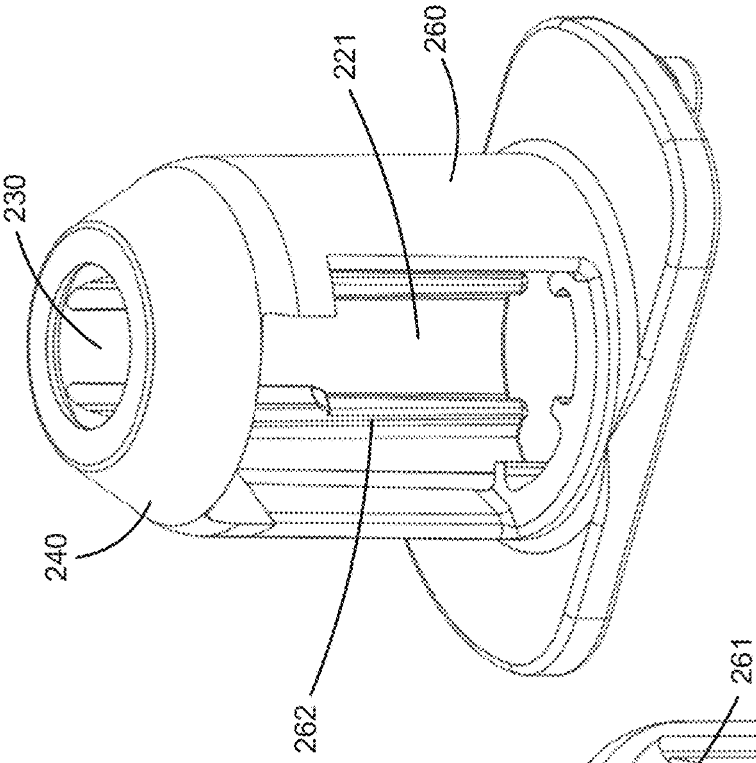
FIG. 2M is another perspective view illustrating an interior of the exemplary port body of FIG. 2A in accordance with some exemplary embodiments of the present disclosure.
Figure 2L:
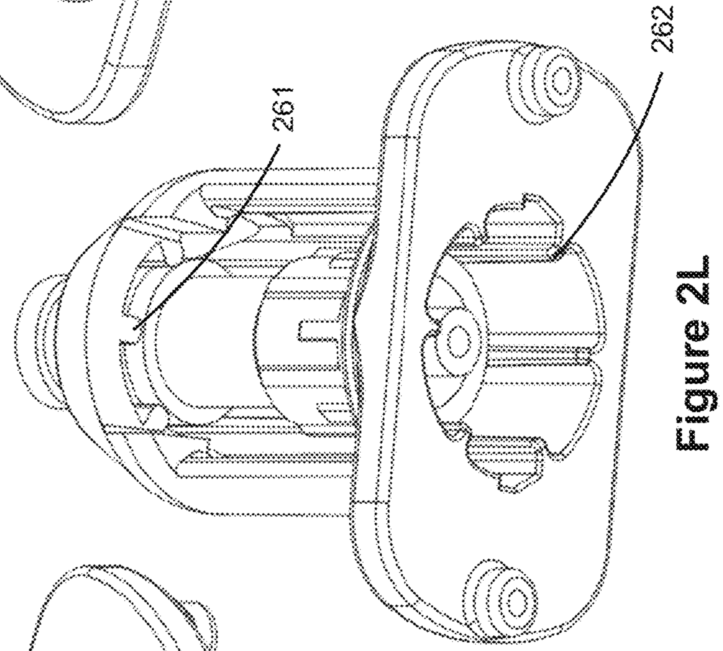
FIG. 2L is another perspective view illustrating an interior of the exemplary port body of FIG. 2A, with a connector held by exemplary port body, in accordance with some exemplary embodiments of the present disclosure.
Figure 2K:
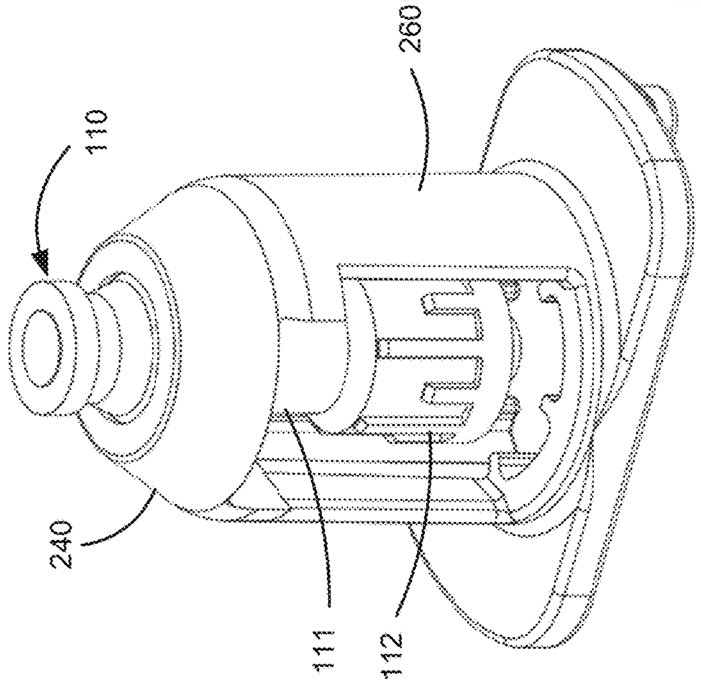
FIG. 2K is a perspective view illustrating an interior of the exemplary port body of FIG. 2A, with a connector held by exemplary port body, in accordance with some exemplary embodiments of the present disclosure.
Figure 2N:
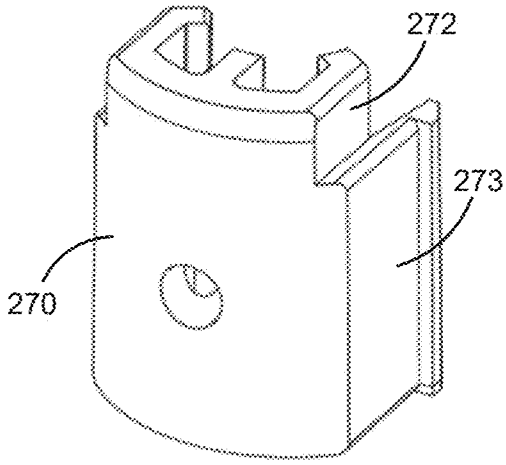
FIG. 2N is a perspective view illustrating a component of the exemplary port body of FIG. 2A in accordance with some exemplary embodiments of the present disclosure.
Figure 2O:
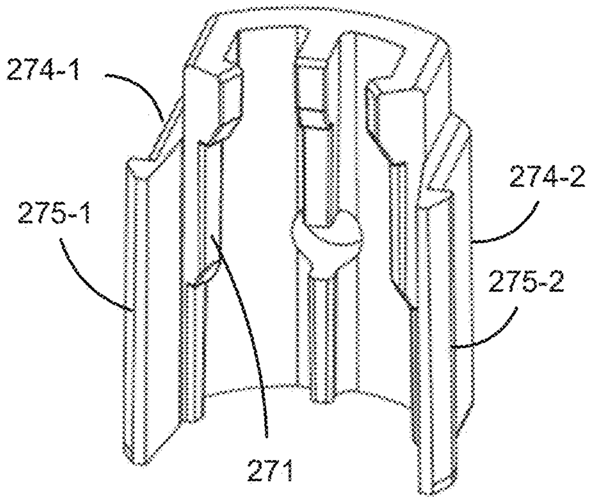
FIG. 2O is another perspective view illustrating the component of FIG. 2N.
Figure 2P:
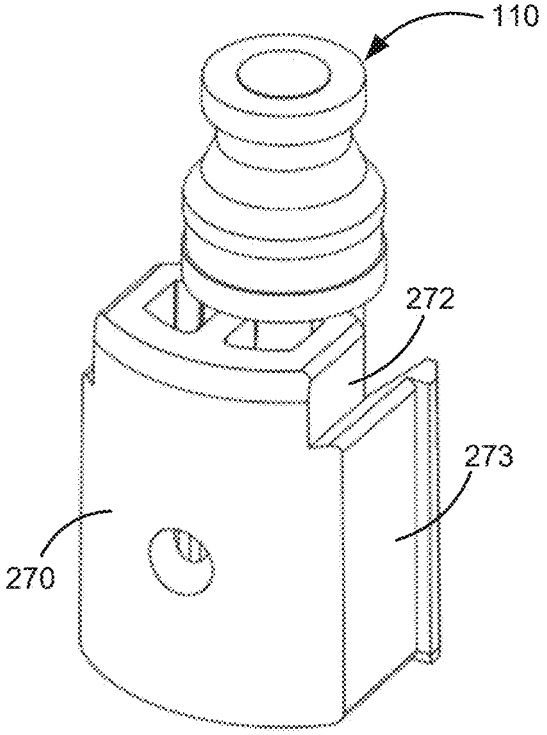
FIG. 2P is a perspective view illustrating the component of FIG. 2N with a connector.
Figure 2Q:
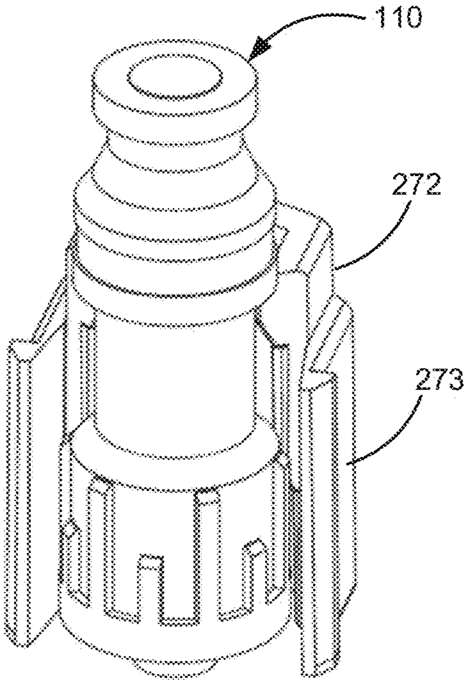
FIG. 2Q is another perspective view illustrating the component of FIG. 2N with a connector.
Figure 3A:
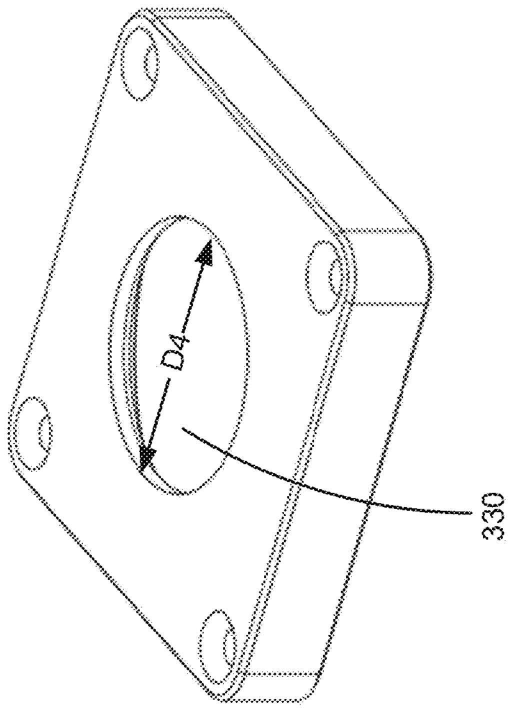
FIG. 3A is a perspective view illustrating a component of an exemplary retainer in accordance with some exemplary embodiments of the present disclosure.
Figure 3B:
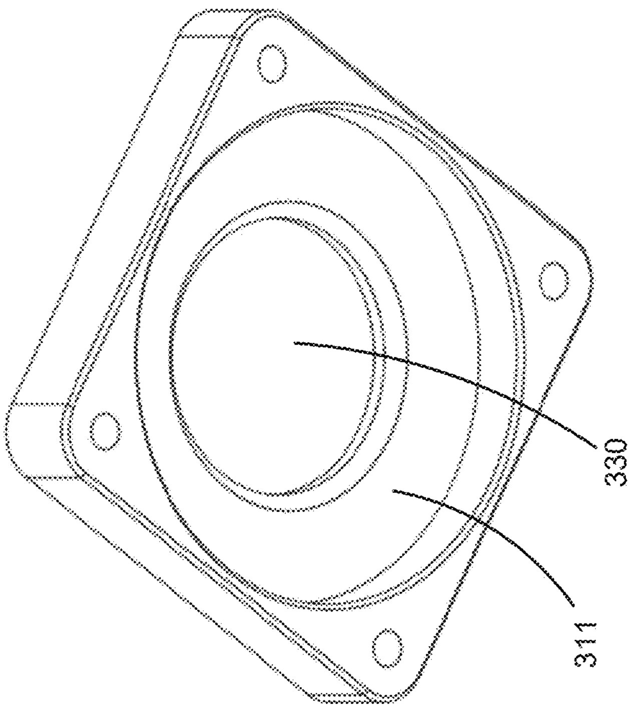
FIG. 3B is another perspective view illustrating the component of an exemplary retainer of FIG. 3A.
Figure 3C:
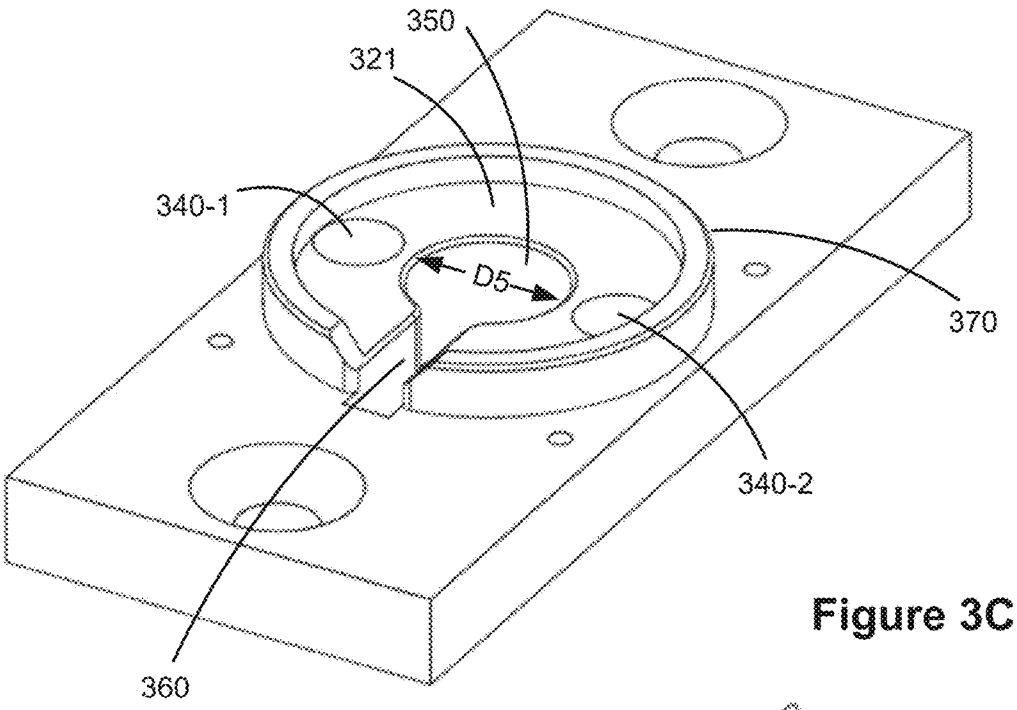
FIG. 3C is a perspective view illustrating another component of an exemplary retainer in accordance with some exemplary embodiments of the present disclosure.
Figure 3D:
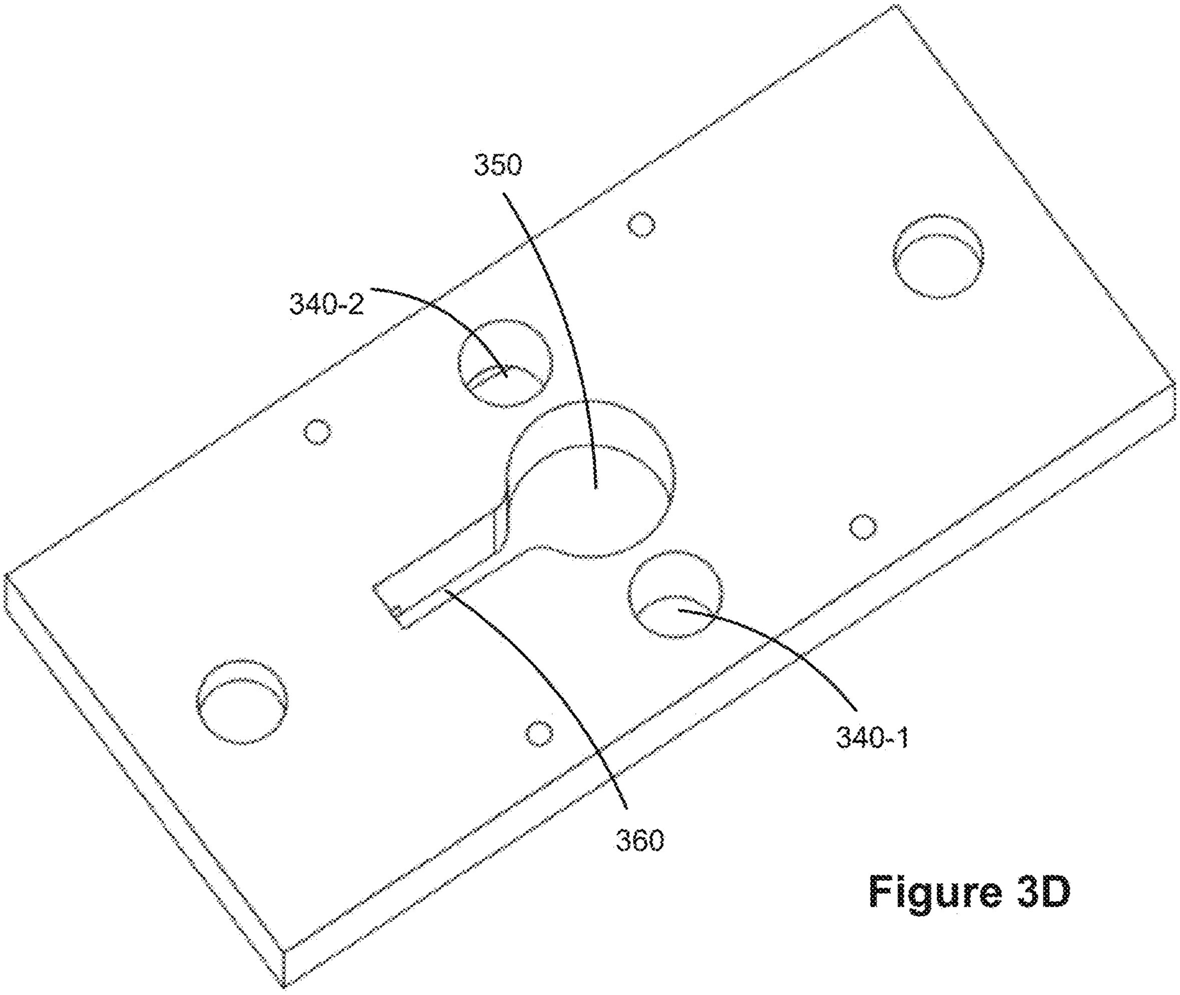
FIG. 3D is another perspective view illustrating the component of an exemplary retainer of FIG. 3C.

Referring to FIGS. 2A-2Q, in some embodiments, the port body 200 includes a base, such as a base 210. While the base is illustrated to be of an oblong shape, it should be noted that this is by way of example and the present disclosure is not limited thereto. For instance, the base can have a circular shape or substantially circular shape. The base can also have other regular or irregular shapes. In some embodiments, the base is planar or substantially planar. The base is characterized by a first dimension (e.g., a width, a diameter) "D1" and a second dimension (e.g., a thickness) "D2."

In some embodiments, the port body 200 includes a stem, such as a stem 220, extended from the base. In some embodiments, the stem is generally cylindrical or substantially cylindrical, with at least a portion of the stem having a circular or substantially circular cross section. The stem is characterized by a third dimension (e.g., an outer diameter) "D3" that is smaller than the first dimension "D1" of the base. In some embodiments, the stem includes two or more stem members that are removably coupled (e.g., snap-fitted, interference-fitted) with each other and configured to help secure the first device at the port body. For instance, in an exemplary embodiment, the stem includes a first stem member 260 and a second stem member 270 removably coupled with each other. In some embodiments, the first stem member is monolithically formed with the base as a single piece, and the second stem member is formed as a separate piece (e.g., an insert) to removably couple with the single piece. In some embodiments, the port body or one or more components of the port body (e.g., the first stem member, the first stem member together with the base, or the second stem member) are formed by molding (e.g., injection molding) of a plastic (e.g., a medical grade plastic).

In some embodiments, the stem is configured to restrict the first device from moving relative to the stem body, e.g., from moving axially and/or rotating around its axis. For instance, in some embodiments, the stem includes a plurality of internal ribs, such as one or more ribs 261, one or more ribs 262, one or more ribs 271, or any combination thereof. In some embodiments, the plurality of internal ribs is disposed on an inner surface 221 of the stem. Each internal rib in the plurality of internal ribs is configured for abutting an external wall 111 of the first device (e.g., having a surface that forms a contact with the external wall) to secure the first device with the port body. In some embodiments, at least some internal ribs in the plurality of internal ribs are distributed circumferentially on the inner surface of the stem.

In some embodiments, each internal rib in at least a subset of the plurality of internal ribs includes a first rib portion disposed at or adjacent the free end portion of the stem and a second rib portion disposed between the free end portion of the stem and the base. For instance, as illustrated in FIGS. 2K-2L, the rib 262 includes a first rib portion disposed at or adjacent the free end portion of the stem and a second rib portion disposed between the free end portion of the stem and the base. In some embodiments, the second rib portion contacts with a knurled surface 112 of the first device. In some embodiments where the stem includes the first stem member and the second stem member, at least one internal rib in the plurality of internal ribs is formed on each of the first stem member and the second stem member. For instance, in some embodiments, one or more ribs 261, one or more ribs 262, or any combination thereof are formed on the first stem member, and one or more ribs 271 are formed on the second stem member.

In some embodiments, the second stem member includes an upper portion 272 and a lower portion 273. In some embodiments, a segment of the upper portion 272 is inserted into a groove 113 (e.g., a neck, a recess, etc.) of the first device as illustrated in FIGS. 2J, 2P and 2Q, thereby helping to secure the first device on the port body and restrict the first device from moving axially relative to the port body. In some embodiments, the lower portion 273 has a pair of arms 274 configured to couple the second stem member with the first stem member. For instance, in some embodiments, each arm includes an engaging member (e.g., a snap-fitting joint) 275 to engage with a complementary engaging member disposed at the first stem member as illustrated in FIGS. 2G and 2H. In an exemplary embodiment, the first stem member includes a plurality of internal recesses, such as recesses 263, formed on the first stem member. The second stem member includes a plurality of protrusions, such as protrusions 275 (e.g., each engaging member 275 is in a form of a protrusion), each snap-fitted into a corresponding internal recess in the plurality of internal recesses formed on the first stem member.

In some embodiments, the port body 200 includes a bore, such as a bore 230, for housing at least a portion of the first device. The bore extends from an upper end portion of the stem to a lower end portion of the base. In other words, the bore passes completely through the port body. To help secure the first device with the port body, in some embodiments, a plurality of internal ribs are disposed on an inner surface of the stem or the port body (e.g., an interior surface that defines the bore). In some embodiments, the internal ribs are distributed circumferentially, with each internal rib having a surface configured for abutting an external wall of the first device and thus assists in securing the first device with the port body. In some embodiments, at least one internal rib in the plurality of internal ribs is formed on each of the first stem member and the second stem member.

In some embodiments, the port body 200 includes a tip, such as a tip 240, at a free end portion of the stem and configured for guiding a second device (not shown) when connecting the second device and the first device. As used herein, the free end portion of the stem refers to an end portion of the stem that is distal to the base and not disposed within the retainer. In some embodiments, the tip is a chamfered tip having a chamfer angle "α" and a chamfer length "L1." In some embodiments, the tip is a large chamfered tip with the chamfer angle of at least 45 degrees, at least 50 degrees, at least 55 degrees, or at least 60 degrees. In some embodiments, the stem has a length "L2," and the chamfer length "L1" of the tip is at least 10%, at least 15%, at least 20%, or at least 25% of the length "L2" of the stem. In an exemplary embodiment, the tip is a large chamfered tip with the chamfer angle within a range of from about 50 degrees to about 60 degrees and/or the chamfer length within a range of from about 15% to about 25% of the length of the stem. As such, the tip of the present disclosure makes it easy for robotic systems to interface with the apparatus when connecting the first device and a second device. In some embodiments, the cambered tip includes a surface having a curvature of radius greater than zero. In some embodiments, the forms a head portion.

In some embodiments, the port body 200 includes one or more first anti-rotation members, such as one or more first anti-rotation members 250. The one or more first anti-rotation members are disposed at the base and configured to couple with one or more second anti-rotation members disposed at the retainer to restrict the port body from rotating relative to the retainer around an axis of the port body (e.g., the axis indicated by the dash line in FIG. 1C). The port body can include any suitable number (e.g., 1, 2, 3, or more than 3) of first anti-rotation members. For instance, in an exemplary embodiment, the port body includes two first anti-rotation members. Moreover, the one or more first anti-rotation members can be disposed at any suitable locations. For instance, in an exemplary embodiment, each of the one or more first anti-rotation members is formed at or adjacent to an outer edge of the base. Further, the one or more first anti-rotation members can be configured with any suitable shape that can be coupled with the second anti-rotation members disposed at the retainer. For instance, in a non-limiting embodiment, each of the one or more first anti-rotation members is a pin formed on the base. In addition, in embodiments with multiple first anti-rotation members, the first anti-rotation members can be but do not have to identical to each other, and can be but do not have to be disposed at locations symmetrical to each other.

Referring to FIGS. 3A-3D, in some embodiments, the retainer 300 includes a first retaining member, such as a first retaining member 310. The first retaining member has a first surface 311. A first through-hole, such as a first through-hole 330, is formed at the first retaining member. In some embodiments, the first through-hole is a circular or substantially circular through-hole. The first through-hole is characterized by a fourth dimension (e.g., a diameter) "D4." The fourth dimension "D4" of the first through-hole is larger or substantially larger than the third dimension "D3" of the stem, thereby allowing the stem of the port body to pass through and to move relative to the first retaining member. Moreover, the fourth dimension "D4" of the first through-hole is smaller than the first dimension "D1" of the base, thereby preventing the base of the port body from pulling out of the retainer via the first through-hole.

In some embodiments, the retainer 300 includes a second retaining member, such as a second retaining member 320, coupled or formed with the first retaining member. The second retaining member has a second surface 321 spaced apart from the first surface of the first retaining member in an axial direction of the port body, with the base of the port body disposed between the first surface of the first retaining member and the second surface of the second retaining member.

In some embodiments, the second dimension "D2" (e.g., the thickness) of the base equals or substantially equals a distance between the first surface of the first retaining member and the second surface of the second retaining member. For instance, in an exemplary embodiment, the thickness of the base equals or substantially equals a distance between the first surface of the first retaining member and the second surface of the second retaining member with a manufacturing clearance between the base and the first surface of the first retaining member and/or the second surface of the second retaining member. As such, the retainer restricts the base and thus the port body from moving in a direction parallel to the axis of the port body. Accordingly, the retainer restricts the first device from moving in a direction parallel to the axis of the port body.

In some embodiments, the retainer 300 includes one or more second anti-rotation members, such as second anti-rotation members 340, configured for coupling with the one or more first anti-rotation members of the port body, thereby restricting the port body from rotating relative to the retainer. The one or more second anti-rotation members can be disposed at the first retaining member or the second retaining member. As a non-limiting example, the one or more second anti-rotation members are illustrated at the second retaining member. Like the port body, the retainer can include any suitable number (e.g., 1, 2, 3, or more than 3) of second anti-rotation members. For instance, in an exemplary embodiment, the retainer includes two second anti-rotation members. The one or more second anti-rotation members can be configured with any suitable shape that can be coupled with the first anti-rotation members disposed at the retainer. For instance, in a non-limiting embodiment, each of the one or more second anti-rotation members is a hole formed at the second retaining member to receive a corresponding pin formed on the base. The hole can be a blind hole (e.g., a hole that does not pass completely through the second retaining member) or a through hole (e.g., a hole that passes completely through the second retaining member). As a non-limiting example, a through hole is illustrated. The size of the hole is generally larger than the size of the corresponding pin.

However, the present disclosure is not limited thereto. For instance, in some alternative embodiments, each of the one or more second anti-rotation members is a pin disposed at the first retaining member or the second retaining member. Each of the one or more first anti-rotation members is a hole formed at the base to receive a corresponding pin disposed at the first retaining member or the second retaining member.

In some embodiments, one or more through-holes and/or one or more slots are formed at the second retaining member to facilitate connecting the first device with an input or output tube of the consumable kit. For instance, as a non-limiting example, it is illustrated that a second through-hole 350 and a slot 360 are formed on the second retaining member. The second through-hole is configured to allow an access to the first connector, and characterized by a fifth dimension (e.g., a diameter) "D5" of the second through-hole. The first dimension "D5" of the second through-hole is smaller than the first dimension "D1" of the base, thereby preventing the base of the port body from pulling out of the retainer via the second through-hole. In some embodiments, the second through-hole is a circular or substantially circular through-hole and concentric with the first through-hole formed on the first retaining member. The slot is configured to accommodate tubing or cable (e.g., an input or output tube of the consumable kit). In some embodiments, the slot extends from the second through-hole all the way to an outer edge of the second retaining member.

In some embodiments, the retainer 300 includes a rim, such as a rim 370, to help set a boundary for translational movement of the port body relative to the retainer. The rim can be disposed on the first surface of the first retaining member or the second surface of the second retaining member. In some embodiments, the rim is an integral part of the first or second retaining member. As a non-liming example, it is illustrated that the rim 370 is formed at the second surface of the second retaining member. The rim can be a single continuous rim or composed of multiple separate rim segments. It can be in a closed form shape or an open form shape. By way of example, the rim is shown to be continuous and in a closed form shape (except the portion cut off by the slot 360) that surrounds the base.

Referring back to FIG. 1C, in some embodiments, the port body 200 and the retainer 300 are configured such that one or more gaps are present between the port body and the retainer to confine the translational movement of the port body relative to the retainer. The one or more gaps include but are not limited to: (i) a first gap "G1" between the stem of the port body and the first through-hole formed on the first retaining member (e.g., a gap between an outer surface of the stem 220 and a surface of the first retaining member that defines the first through-hole 330), (ii) a second gap "G2" between each respective first anti-rotation member in the one or more first anti-rotation members and a corresponding second anti-rotation member in the one or more second anti-rotation members (e.g., a gap between an outer surface of the pin 250 disposed at the base and a surface of the second retaining member that defines the hole 350), (iii) a third gap "G3" between the rim (e.g., an inner surface of the rim) formed on the first surface of the first retaining member or the second surface of the second retaining member and an outer edge of the base of the port body, or (iv) any combination thereof. In some such embodiments, the port body is movable translationally relative to the retainer in the plane substantially perpendicular to the axial direction of the port body within a range defined by the first gap, the second gap, the third gap, or any combination thereof. In some embodiments, the port body is movable translationally relative to the retainer in a radial direction of the port body. In some embodiments, the one or more gaps allow the port body to move translationally relative to the retainer in a radial direction of the port body for at least 1 mm, at least 1.5 mm, at least 2 mm, at least 2.5 mm, or at least 3 mm. in some embodiments, the one or more gaps allow the port body to move translationally relative to the retainer in a radial direction of the port body for at most 5 mm, at most 4.5 mm, at most 4 mm, at most 3.5 mm, or at most 3 mm. In some embodiments, the one or more gaps allow the port body to move translationally relative to the retainer in a radial direction of the port body from about 2 mm to about 3 mm. In an exemplary embodiment, the one or more gaps allow the port body to move translationally relative to the retainer in a radial direction of the port body for about 2.5 mm.

The port body 200 and/or the retainer 300 can have additional, optional or alternative components to suit various applications. For instance, the port body can be configured with additional, optional or alternative components to house any specific device such as a fluid connector, a gas connector, an electrical connector, or any combination thereof. The second retaining member 320 of the retainer can be configured for mounting the retainer on another device. The second retaining member of the retainer can also be a component (e.g., a wall, a plate, a block, or the like) of another device. Further, the second retaining member of one retainer can be an individual piece or monolithically formed with one or more second retaining members of other retainers.

As a first non-limiting example, FIGS. 4A-4H illustrates an exemplary port body, generally designated 400, in accordance with some exemplary embodiments of the present disclosure. Like the port body 200, the port body 400 is configured to couple with a retainer disclosed here (e.g., the retainer 300 disclosed in FIGS. 3A-3B, 6A-6C, 7A-7H and 8A-8D) to accommodate axial misalignment but resist torsional loads when connecting a first device (e.g., the first device 110) and a second device.

In some embodiments, the port body 400 includes a base, such as a base 410. The base 410 is similar to the base 210 except the base 410 is illustrated to be of a circular shape while the base 210 is illustrated to be of an oblong shape. For instance, in some embodiments, the base 410 is planar or substantially planar. In some embodiments, the base 410 is characterized by the first dimension (e.g., a width, a diameter) "D1" and the second dimension (e.g., a thickness) "D2."

In some embodiments, the port body 400 includes a stem, such as a stem 420, extended from the base. The stem 420 is similar to the stem 220. For instance, in some embodiments, the stem 420 is generally cylindrical or substantially cylindrical, with at least a portion of the stem having a circular or substantially circular cross section. In some embodiments, the stem 420 is characterized by the third dimension (e.g., an outer diameter) "D3" that is smaller than the first dimension "D1" of the base 410. In some embodiments, the stem 420 includes two or more stem members that are removably coupled (e.g., snap-fitted, interference-fitted) with each other and configured to help secure the first device at the port body. For instance, in an exemplary embodiment, the stem 420 includes a first stem member 460 and a second stem member 470 removably coupled with each other. In some embodiments, the first stem member 460 is monolithically formed (e.g., molded) with the base 410 as a single piece, and the second stem member 470 is formed as a separate piece (e.g., an insert) to removably couple with the single piece.

In some embodiments, the stem 420 is configured to restrict the first device from moving relative to the stem body, e.g., from moving axially and/or rotating around its axis. For instance, in some embodiments, the stem 420 includes a plurality of internal ribs, such as one or more ribs 461, one or more ribs 462, one or more ribs 471, or any combination thereof. The plurality of internal ribs is disposed on an inner surface 421 of the stem. Each internal rib in the plurality of internal ribs is configured for abutting an external wall 111 of the first device (e.g., having a surface that forms a contact with the external wall) to secure the first device with the port body. In some embodiments, at least some internal ribs in the plurality of internal ribs are distributed circumferentially on the inner surface of the stem.

Figure 4B:
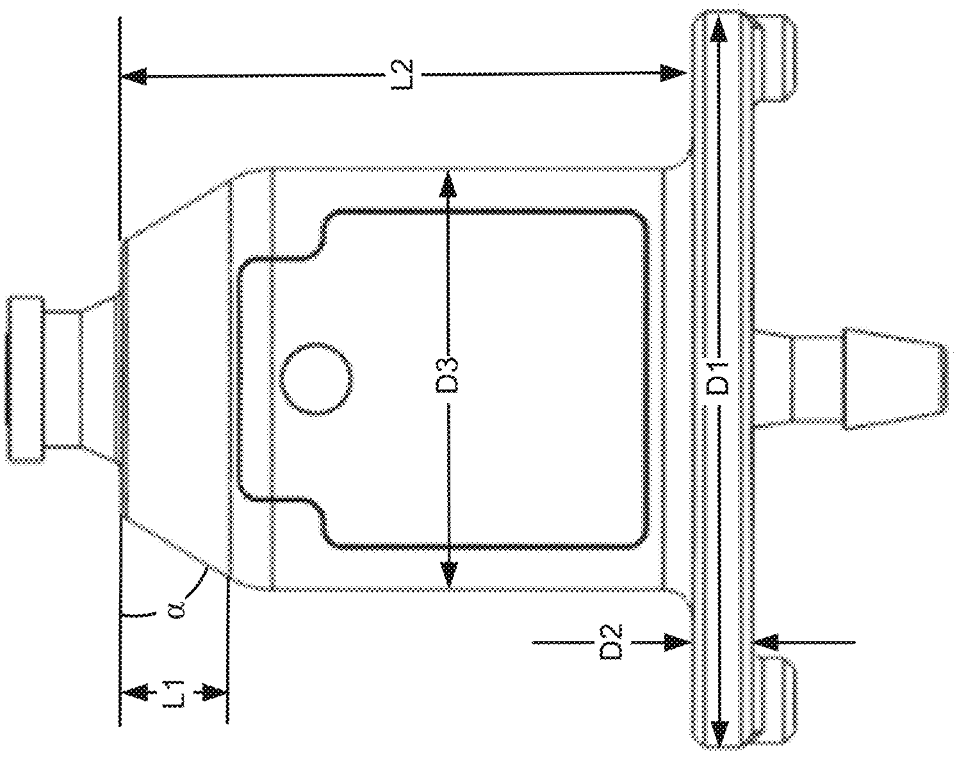
FIG. 4B is a side view illustrating the exemplary port body of FIG. 4A.
Figure 4A:
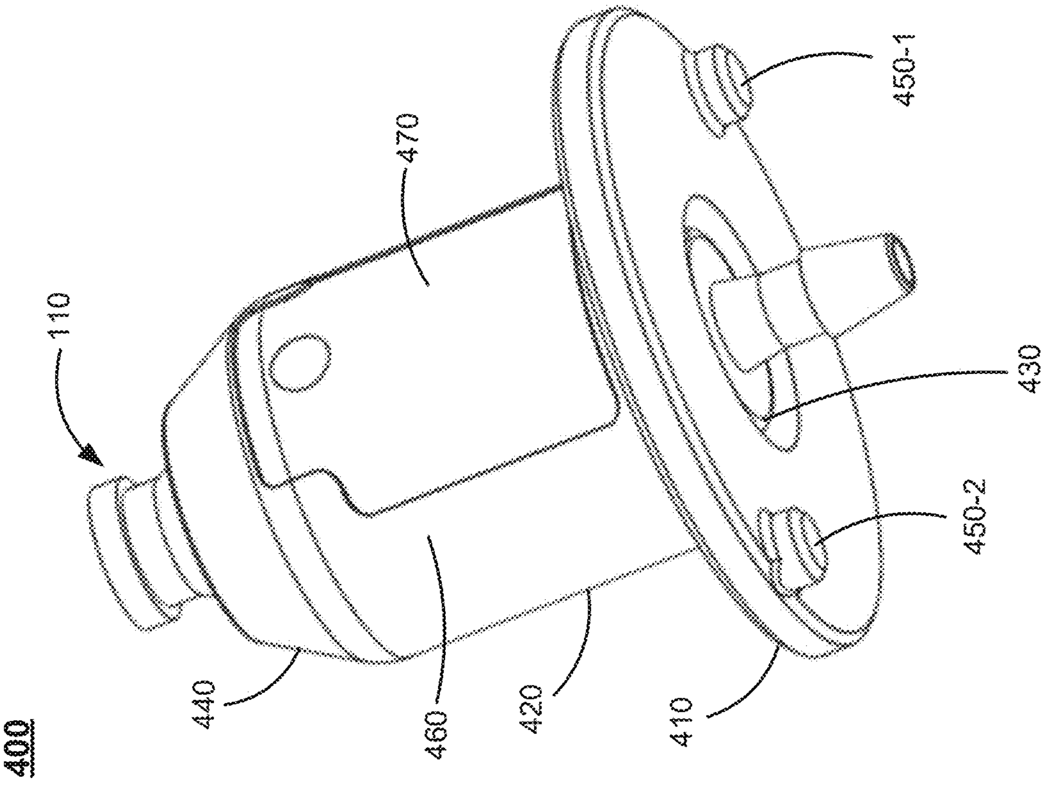
FIG. 4A is a perspective view illustrating an exemplary port body in accordance with some exemplary embodiments of the present disclosure.
Figure 4D:
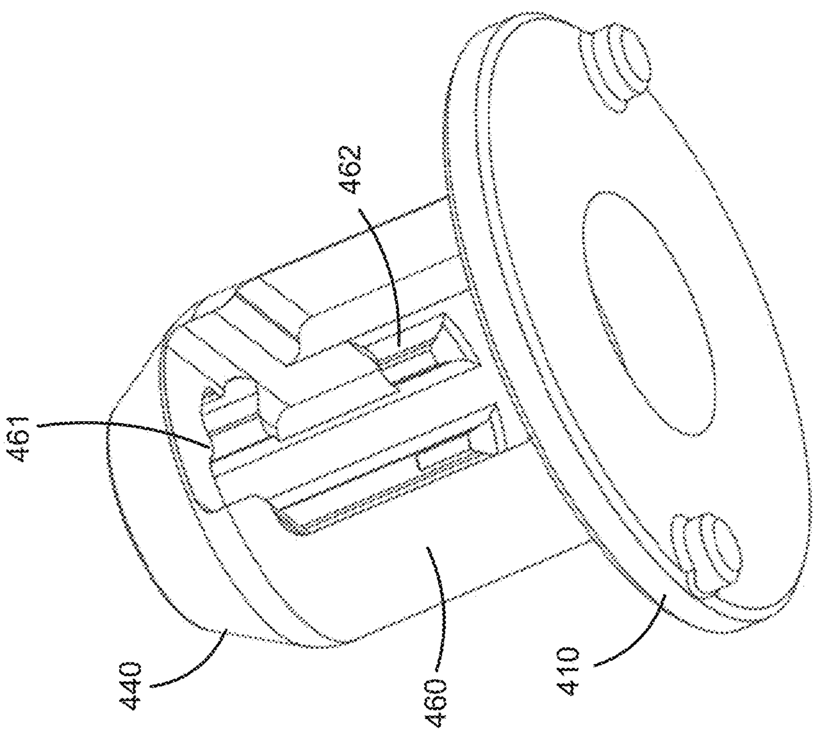
FIG. 4D is a perspective view illustrating an interior of the exemplary port body of FIG. 4A in accordance with some exemplary embodiments of the present disclosure.
Figure 4C:
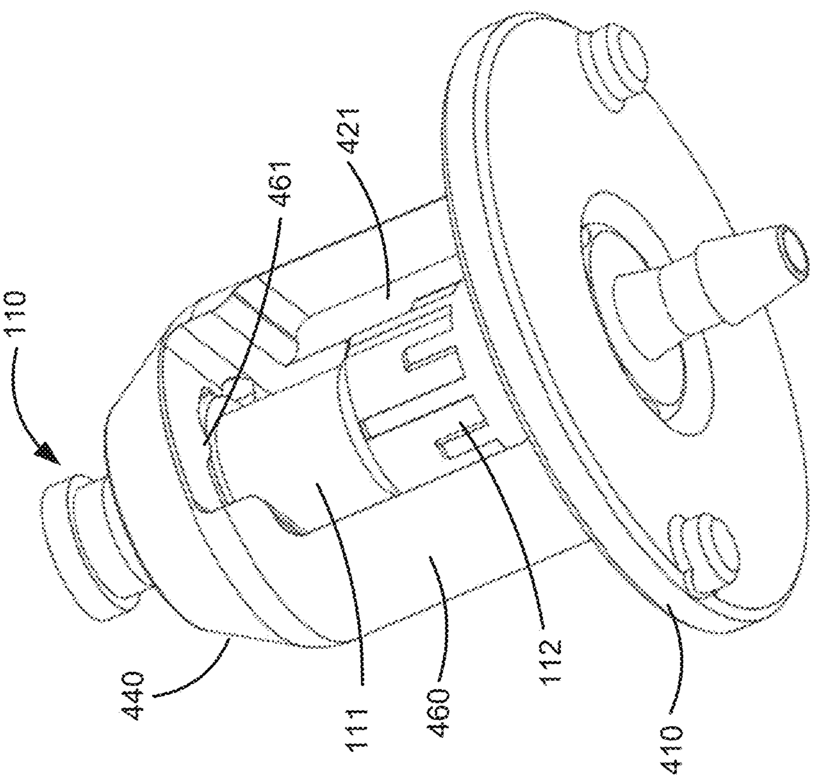
FIG. 4C is a perspective view illustrating an interior of the exemplary port body of FIG. 4A, with a connector held by exemplary port body, in accordance with some exemplary embodiments of the present disclosure.
Figure 4F:
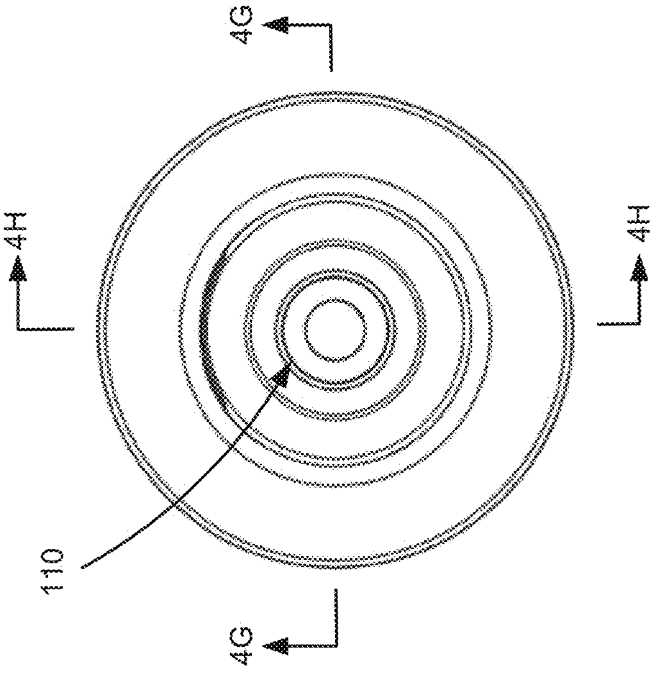
FIG. 4F is a top view illustrating the exemplary port body of FIG. 4A in accordance with some exemplary embodiments of the present disclosure
Figure 4E:
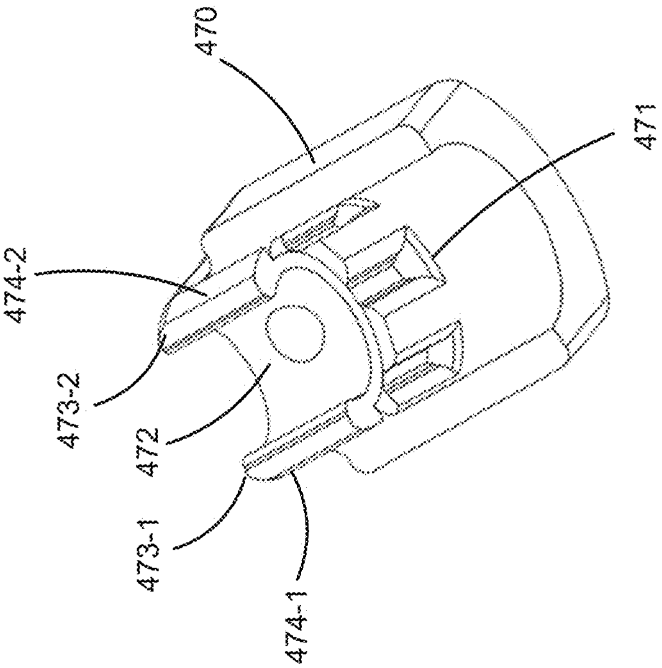
FIG. 4E is a perspective view illustrating a stem member of the exemplary port body of FIG. 4A in accordance with some exemplary embodiments of the present disclosure.

In some embodiments, each internal rib in at least a subset of the plurality of internal ribs includes a first rib portion disposed at or adjacent the free end portion of the stem and a second rib portion disposed between the free end portion of the stem and the base. For instance, as illustrated in FIG. 4D, the rib 462 includes a first rib portion disposed at or adjacent the free end portion of the stem and a second rib portion disposed between the free end portion of the stem and the base. In some embodiments, the second rib portion contacts with a knurled surface 112 of the first device. In some embodiments where the stem includes the first stem member and the second stem member, at least one internal rib in the plurality of internal ribs is formed on each of the first stem member and the second stem member. For instance, one or more ribs 461, one or more ribs 462, or any combination thereof are formed on the first stem member, and one or more ribs 471 are formed on the second stem member.

Figure 4H:
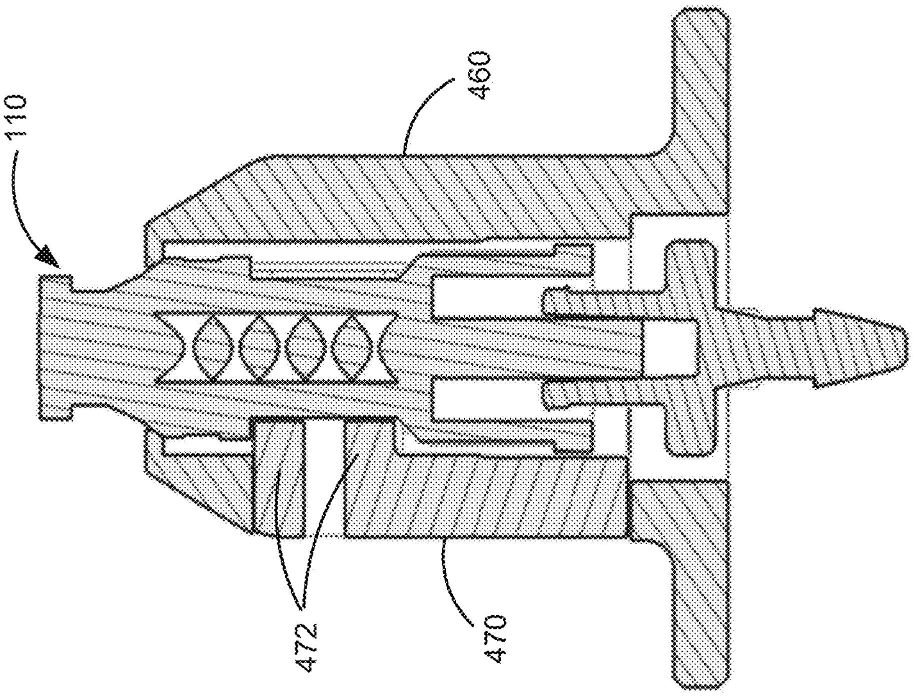
FIG. 4H is a cross-sectional view taken along line 4H-4H of FIG. 4F.
Figure 4G:
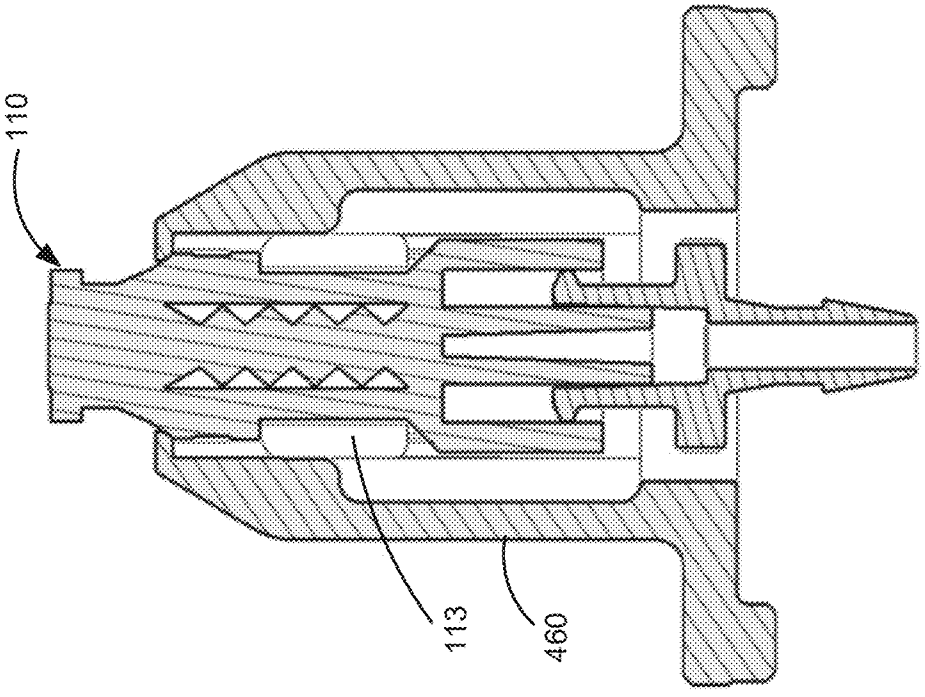
FIG. 4G is a cross-sectional view taken along line 4G-4G of FIG. 4F.

In some embodiments, the second stem member includes an upper portion 472 having a pair of arms 473 configured to couple the second stem member with the first stem member, for instance, in an exemplary embodiment, each arm includes an engaging member (e.g., a snap-fitting joint) 474 to engage with a complementary engaging member disposed at the first stem member. In some embodiments, a segment of the upper portion 472 is inserted into a groove 113 (e.g., a neck, a recess) of the first device as illustrated in FIG. 4H, thereby helping to secure the first device on the port body and restrict the first device from moving axially relative to the port body.

In some embodiments, the port body 400 includes a bore, such as a bore 430, for housing at least a portion of the first device. The bore 430 is the same or substantially the same as the bore 230. For instance, the bore 430 extends from an upper end portion of the stem 420 to a lower end portion of the base 410, i.e., passing completely through the port body 400.

In some embodiments, the port body 400 includes a tip, such as a tip 440, at a free end portion of the stem 420 and configured for guiding a second device (not shown) when connecting the second device and the first device. The tip 440 is the same or substantially the same as the tip 240. For instance, like the tip 240, in some embodiments, the tip 440 is a chamfered tip having the chamfer angle "α" and the chamfer length "L1." In some embodiments, the chamfer angle "α" is at least 45 degrees, at least 50 degrees, at least 55 degrees, or at least 60 degrees. In some embodiments, the chamfer length "L1" is at least 10%, at least 15%, at least 20%, or at least 25% of the length "L2" of the stem.

In some embodiments, the port body 400 includes one or more first anti-rotation members, such as one or more first anti-rotation members 450. The one or more first anti-rotation members 450 is the same or substantially the same as the one or more first anti-rotation members 250. For instance, the one or more first anti-rotation members 450 are disposed at the base 410 and configured to couple with one or more second anti-rotation members disposed at the retainer to restrict the port body 400 from rotating relative to the retainer around an axis of the port body. In some embodiments, each of the one or more first anti-rotation members 450 is a pin formed on the base.

As a second non-limiting example, FIGS. 5A-5E illustrates an exemplary port body, generally designated 500, in accordance with some exemplary embodiments of the present disclosure. Like the port body 200 and the port body 400, the port body 500 is configured to couple with the retainer disclosed here (e.g., the retainer 300 disclosed in FIGS. 3A-3B, 6A-6C, 7A-7H and 8A-8D) to accommodate axial misalignment but resist torsional loads when connecting a first device (e.g., the first device 110) and a second device.

Figure 5B:
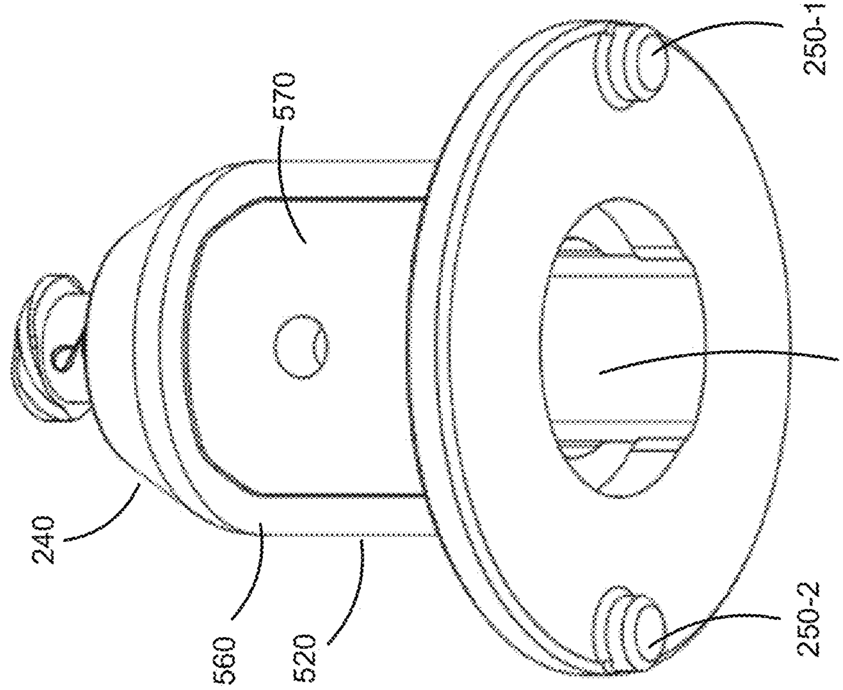
FIG. 5B is another perspective view illustrating the exemplary port body of FIG. 5A.
Figure 5A:
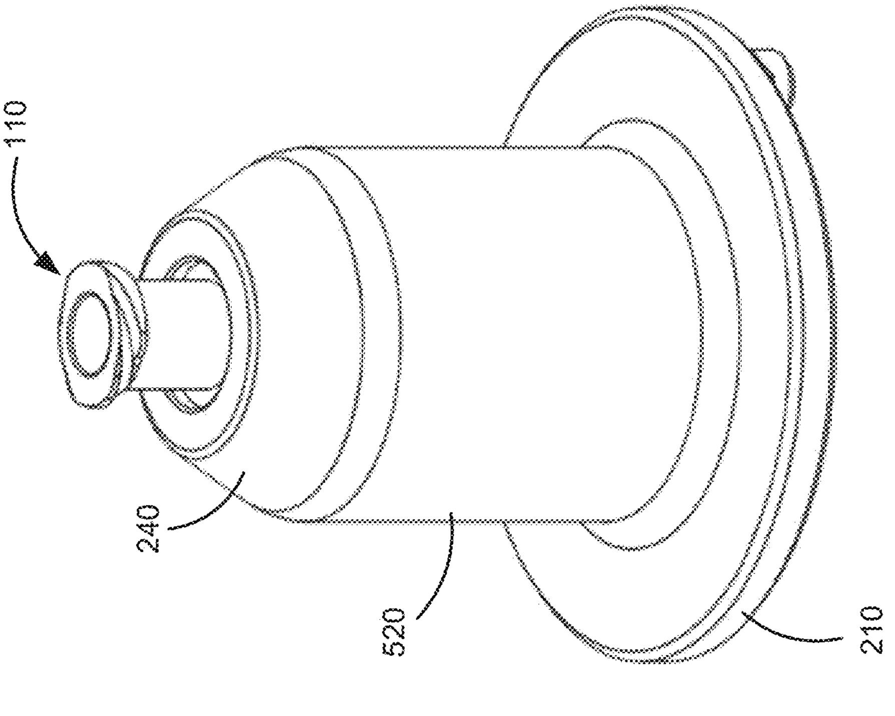
FIG. 5A is a perspective view illustrating an exemplary port body in accordance with some exemplary embodiments of the present disclosure.
Figure 5D:
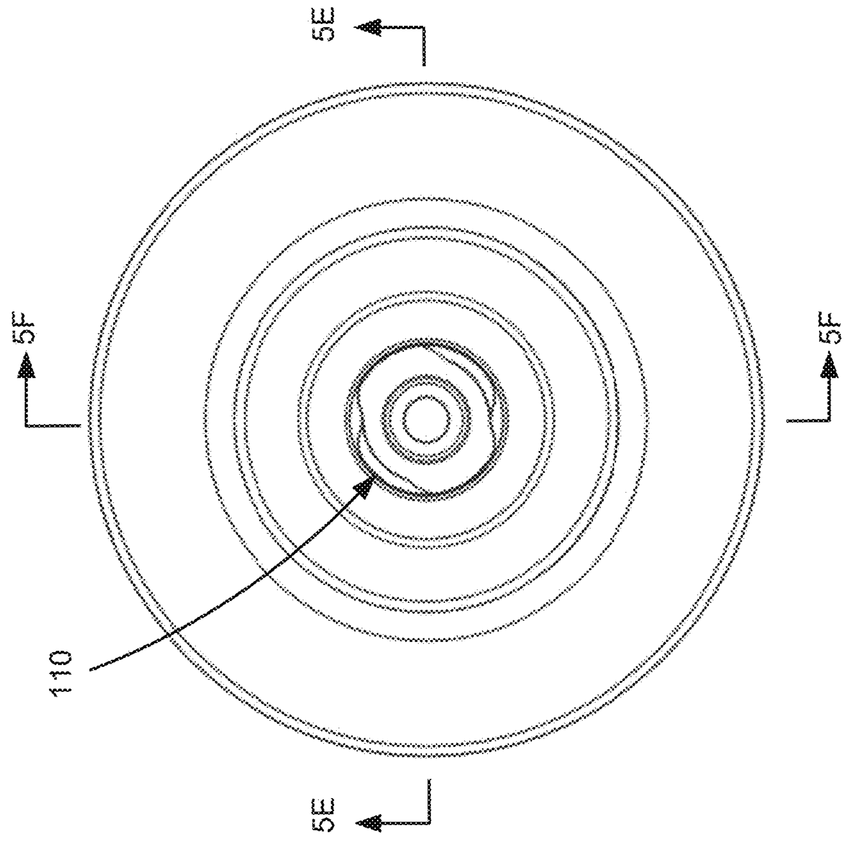
FIG. 5D is a top view illustrating the exemplary port body of FIG. 5A.
Figure 5C:
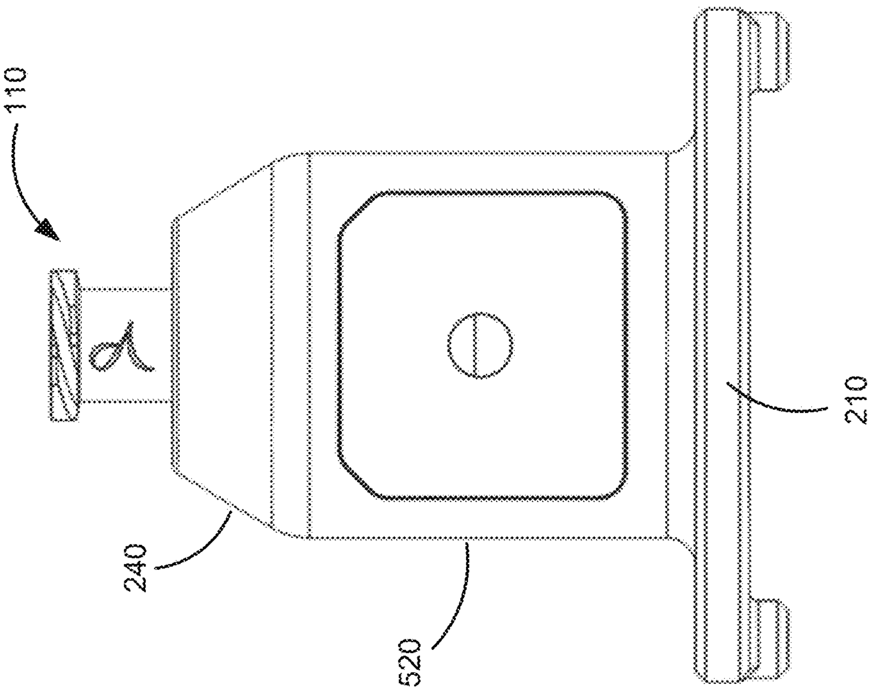
FIG. 5C is a side view illustrating the exemplary port body of FIG. 5A.
Figure 5F:
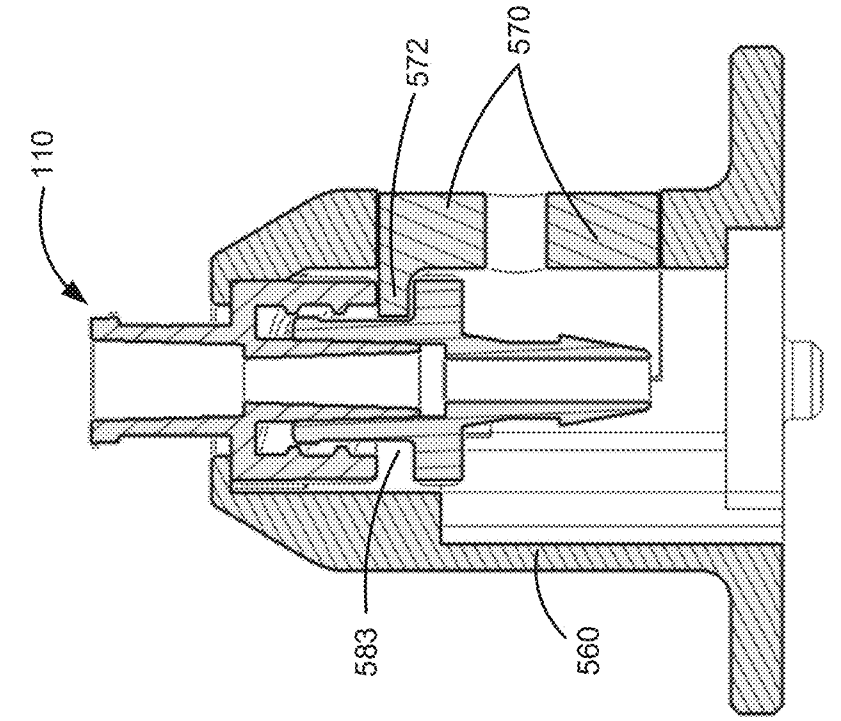
FIG. 5F is another cross-sectional view taken along line 5F-5F of FIG. 5D.
Figure 5E:
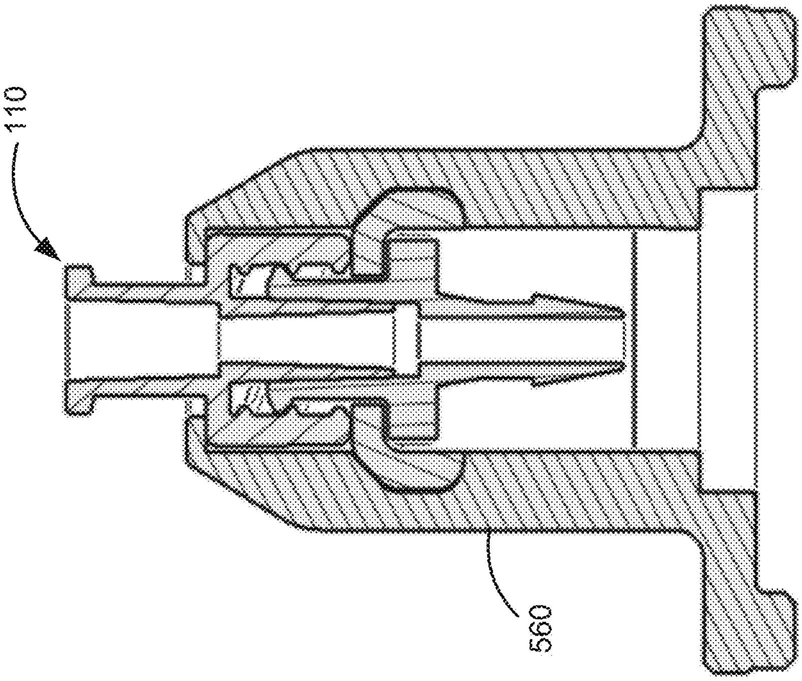
FIG. 5E is a cross-sectional view taken along line 5E-5E of FIG. 5D.

In some embodiments, the port body 500 is configured similarly to the port body 200 and/or the port body 400. For instance, in some embodiments, the port body 500 includes a base, such as a base 210. In some embodiments, the port body 500 includes a stem, such as a stem 520, extended from the base 210. The stem 520 is similar to the stem 220, e.g., it is characterized by a length "L2" and a third dimension (e.g., an outer diameter) "D3" that is smaller than the first dimension "D1" of the base. In some embodiments, the stem includes two or more stem members that are removably coupled (e.g., snap-fitted, interference-fitted) with each other and configured to help secure the connector 500 (e.g., a gas connector) at the port body. For instance, in an exemplary embodiment, the stem includes a first stem member 560 and a second stem member 570 removably coupled with each other. In some embodiments, the first stem member is monolithically formed (e.g., molded) with the base as a single piece, and the second stem member is formed as a separate piece (e.g., an insert) to removably couple with the single piece. In some embodiments, the second stem member includes an upper portion 572 and a segment of the upper portion 572 is inserted into a groove (e.g., a neck, a recess) of the connector as illustrated in FIG. 5D, thereby helping to secure the connector on the port body and restrict the connector from moving axially relative to the port body. In some embodiments, the port body 500 includes a bore, such as a bore 530, for housing at least a portion of the connector. The bore 530 is similar to the bore 230, e.g., it passes completely through the port body. In some embodiments, the port body 500 includes a tip, such as a tip 240, at a free end portion of the stem. In some embodiments, the port body 500 includes one or more first anti-rotation members, such as one or more first anti-rotation members 250.

In some embodiments, the port body 200 or the port body 400 is configured to house a fluid connector, such as a fluid connector comprised of a needle-free valve, a female luer, a barb connector, or any combination thereof. In some embodiments, the port body 500 is configured to house a gas connector. However, the present disclosure is not limited thereto. For instance, any port body disclosed herein can be configured to house an electrical connector or other device.

Figure 6A:
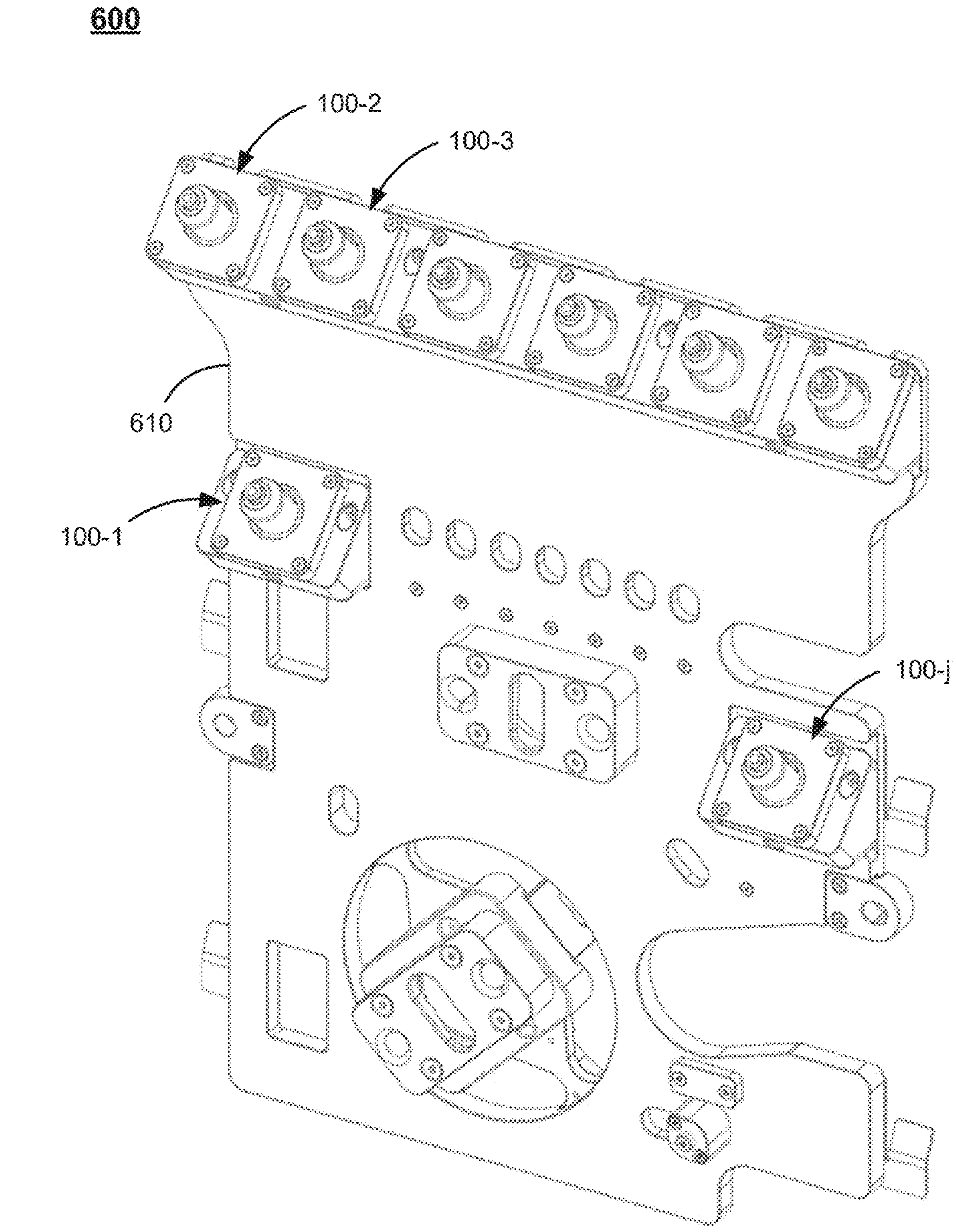
FIG. 6A is a perspective view illustrating an exemplary cartridge including a plurality of port assemblies in accordance with some exemplary embodiments of the present disclosure.
Figure 6B:
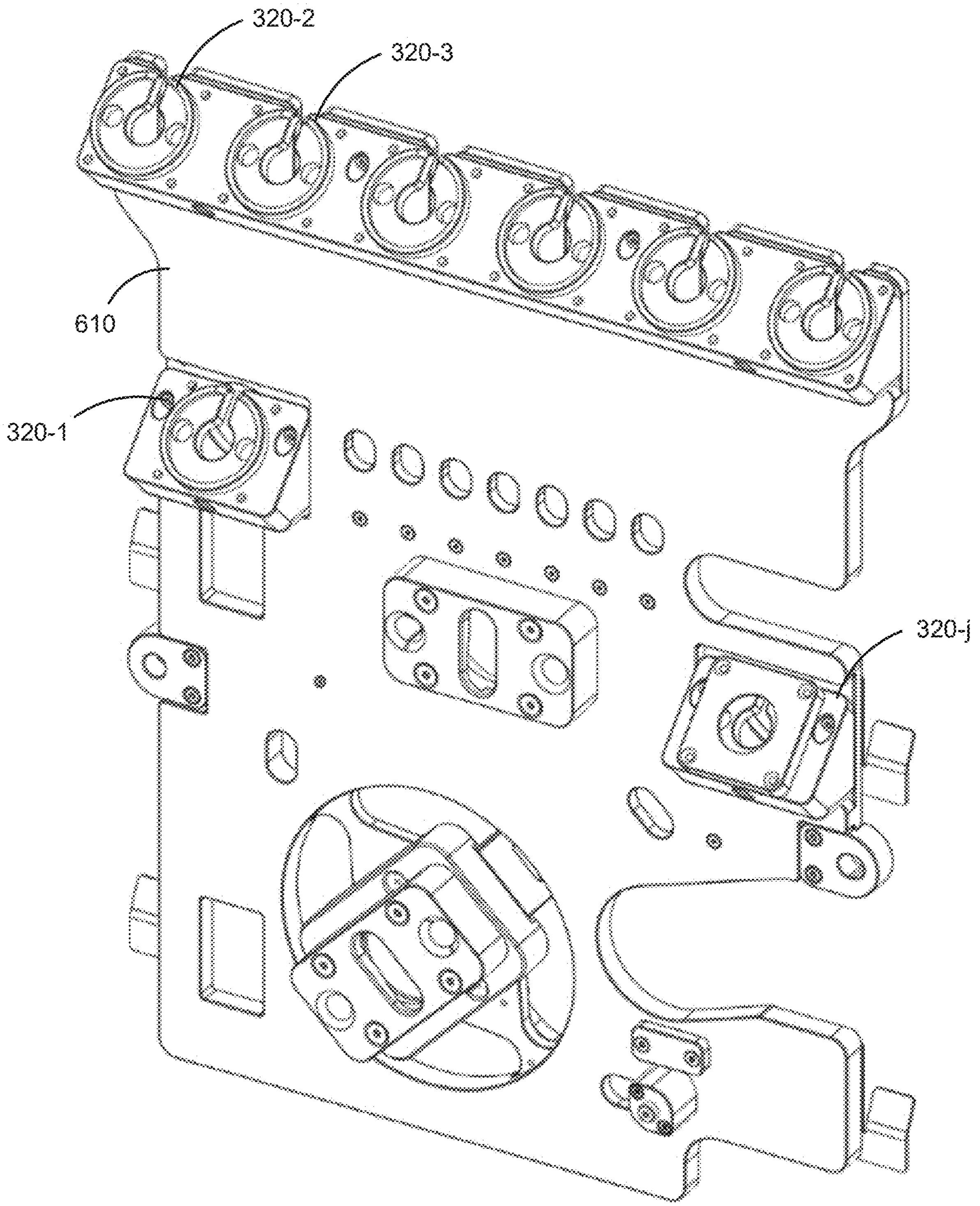
FIG. 6B is a perspective view illustrating the exemplary cartridge of FIG. 6A, where some components of the port assemblies are removed.
Figure 6C:
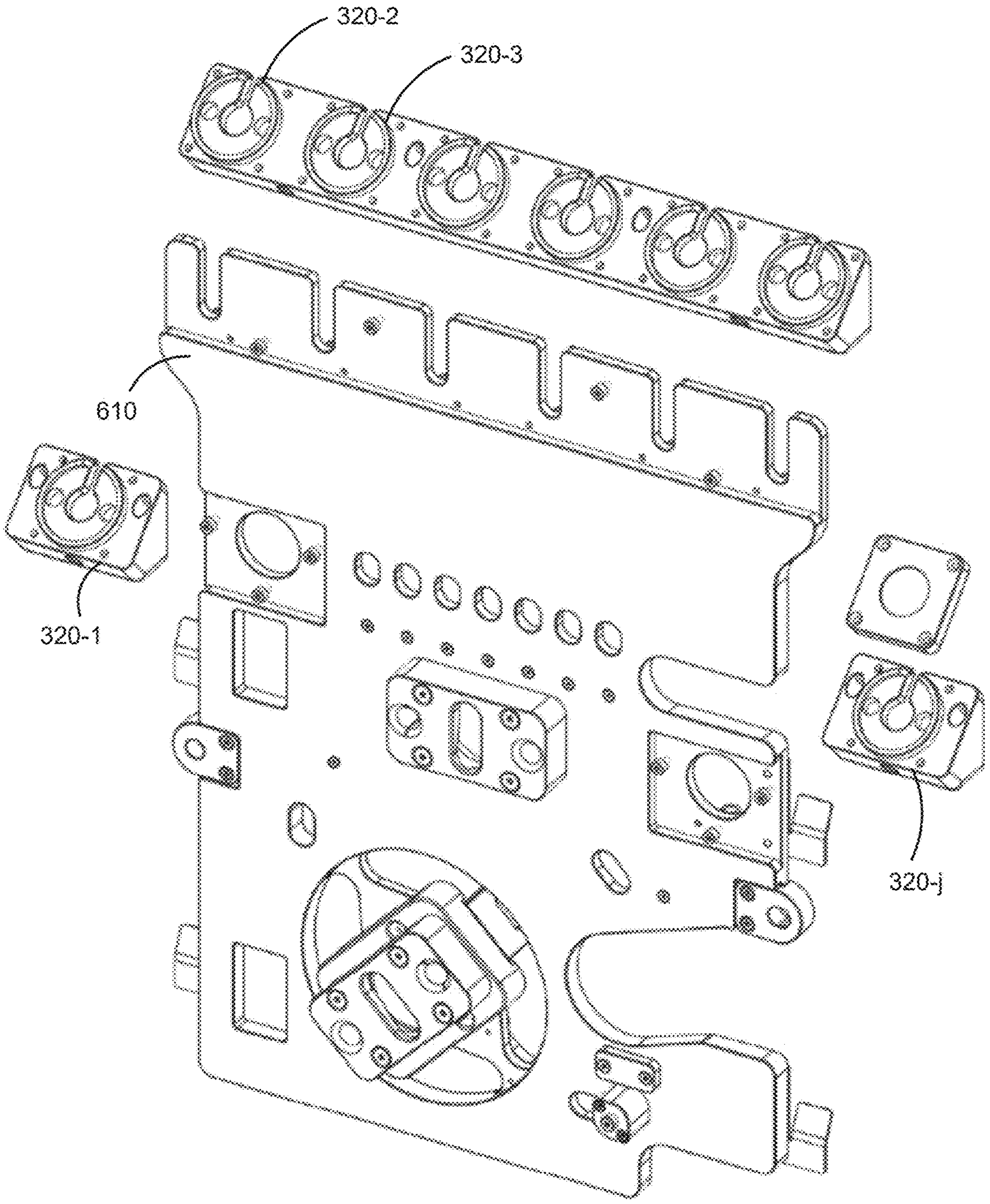
FIG. 6C is a partially exploded view illustrating the exemplary cartridge of FIG. 6B.
Figure 6E:
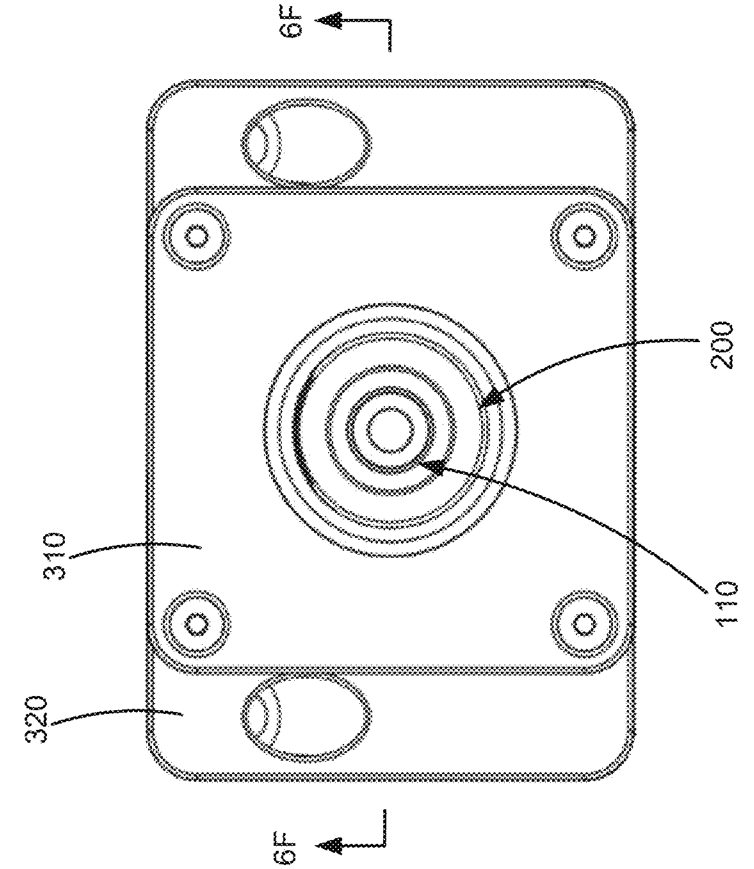
FIG. 6E is a top view illustrating the exemplary apparatus of FIG. 6D.
Figure 6D:
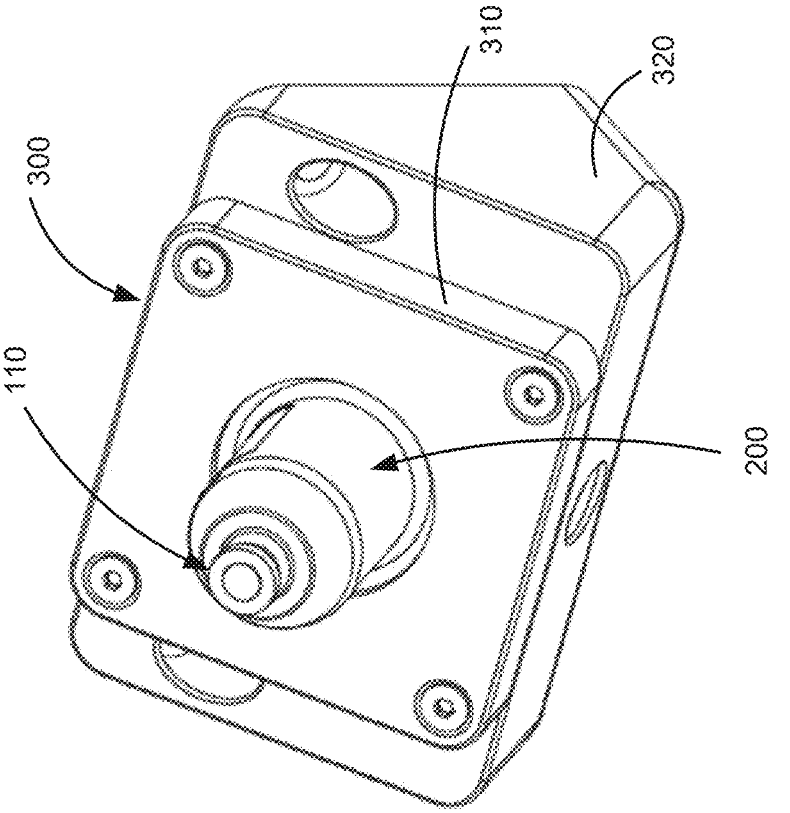
FIG. 6D is a perspective view illustrating an exemplary apparatus (also referred herein as a port assembly) used in the exemplary cartridge of FIG. 6A in accordance with some exemplary embodiments of the present disclosure.
Figure 6F:
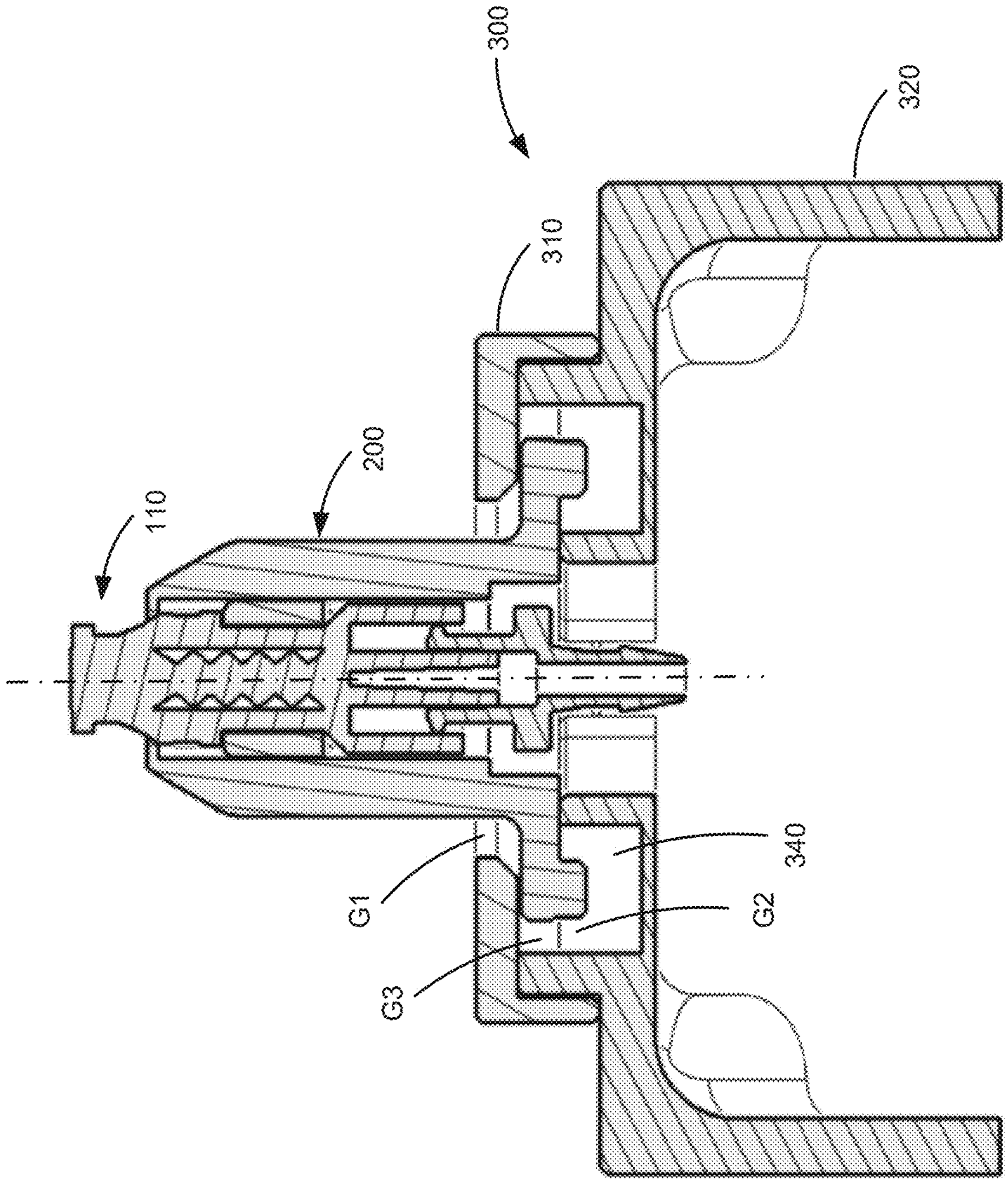
FIG. 6F is a cross-sectional view taken along line 6F-6F of FIG. 6E.
Figure 6G:
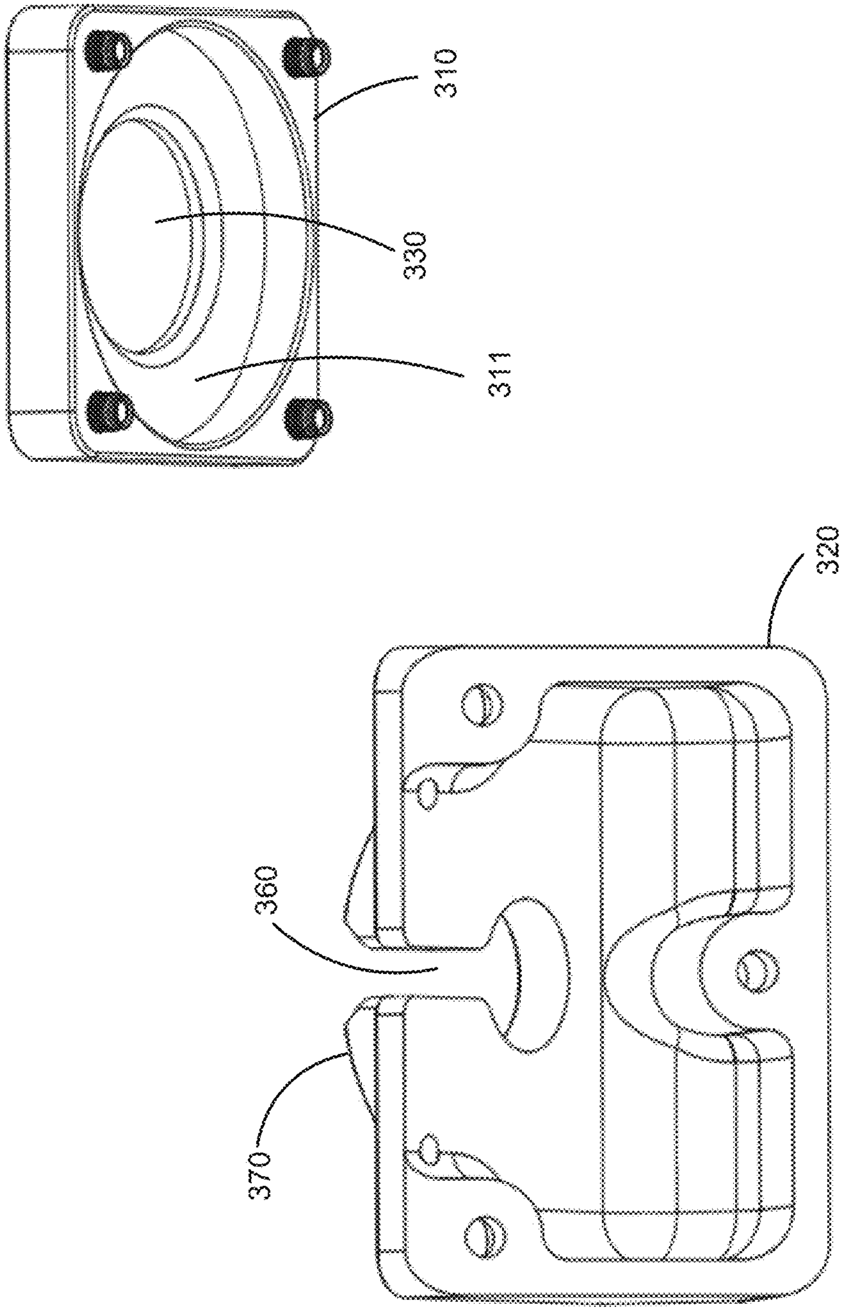
FIG. 6G is an exploded view illustrating an exemplary retainer in accordance with some exemplary embodiments of the present disclosure.
Figure 6H:
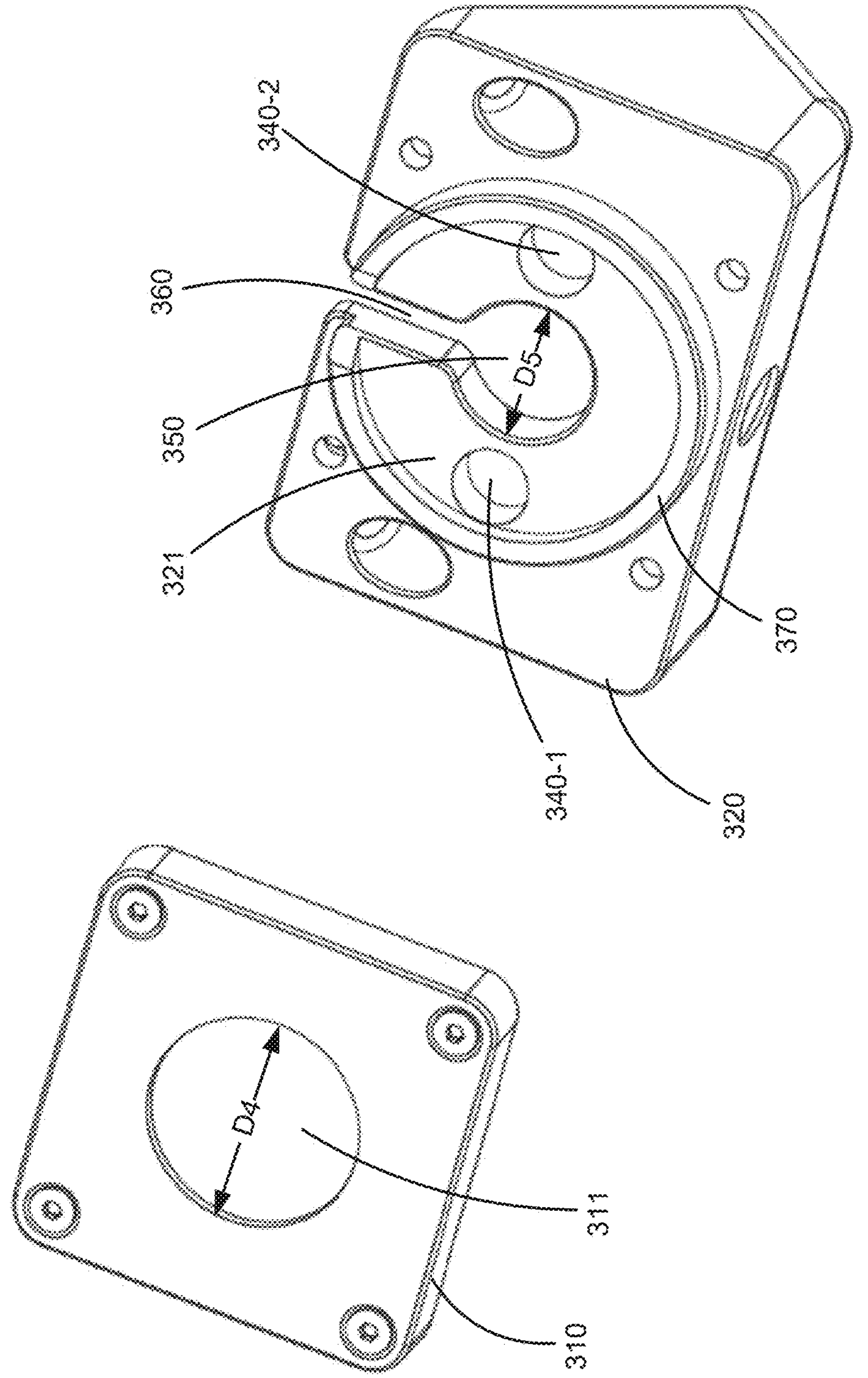
FIG. 6H is another exploded view illustrating the exemplary retainer of FIG. 6G.

As a third non-limiting example, FIGS. 6A-6C illustrate an exemplary cartridge, generally designated 600, in accordance with some exemplary embodiments of the present disclosure. The cartridge includes a mounting member 610 and a plurality of apparatuses 100 disposed at the mounting member. In this non-limiting example, the second retaining member of each of the plurality of apparatuses 100 is configured for mounting the retainer to the mounting member 610 of the cartridge. More specifically, each of the second retaining member 320-1 of the apparatus 100-1 and the second retaining member 320-*j* of the apparatus 100-*j* is an individual piece that is connected to the mounting member. The second retaining members 320-2, 320-3, etc., of the apparatuses 100-2, 100-3, etc., are monolithically formed as a single piece that is connected to the mounting member. In addition, the second retaining member can be configured to any suitable shape, size, and in some cases, can include additional or alternative elements to ensure the port body at a desired orientation. For instance, as a non-limiting example, FIGS. 6D-6H illustrate an apparatus (e.g., the apparatus 100-1 or 100-*j* in FIG. 6A), where the second retaining member is not a planar block.

Figure 7A:
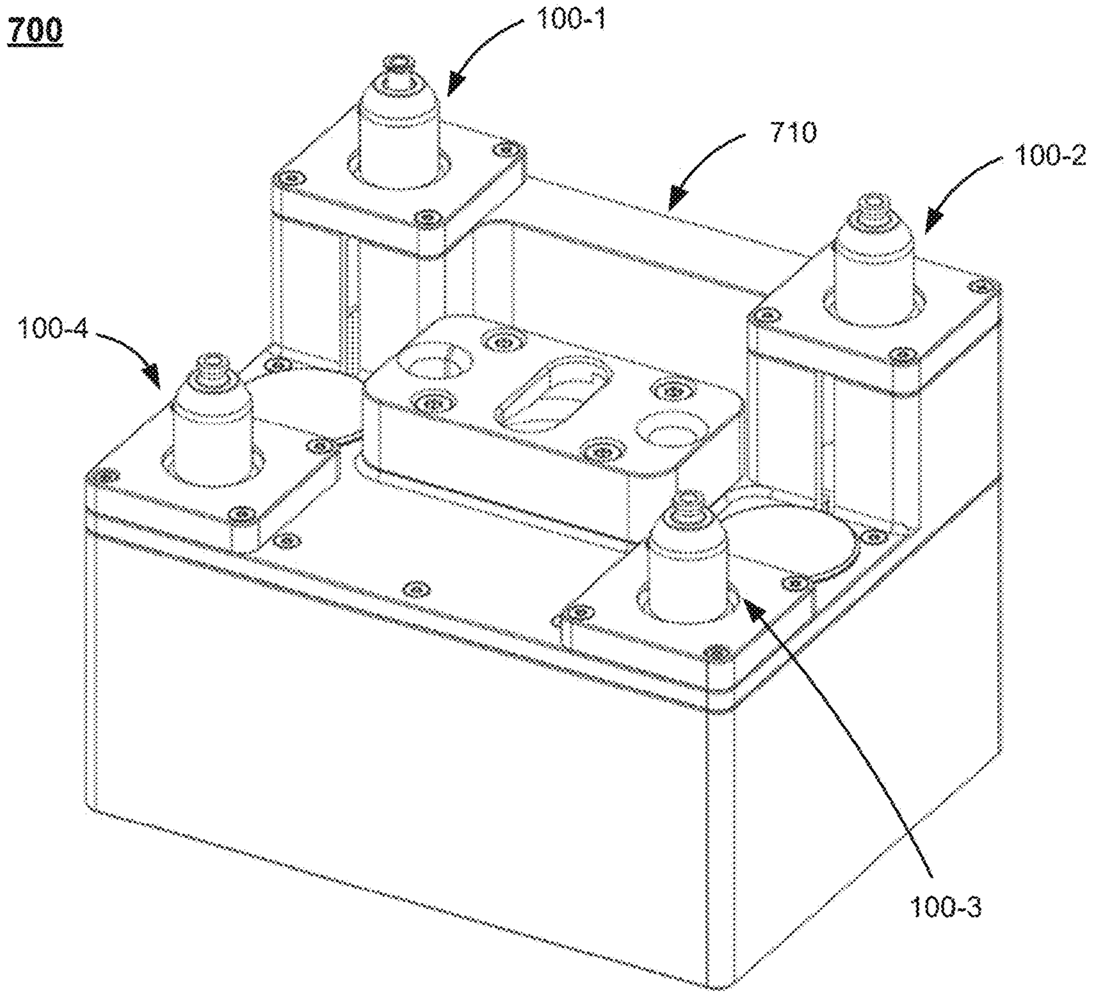
FIG. 7A is a perspective view illustrating another exemplary cartridge including a plurality of port assemblies in accordance with some exemplary embodiments of the present disclosure.
Figure 7B:
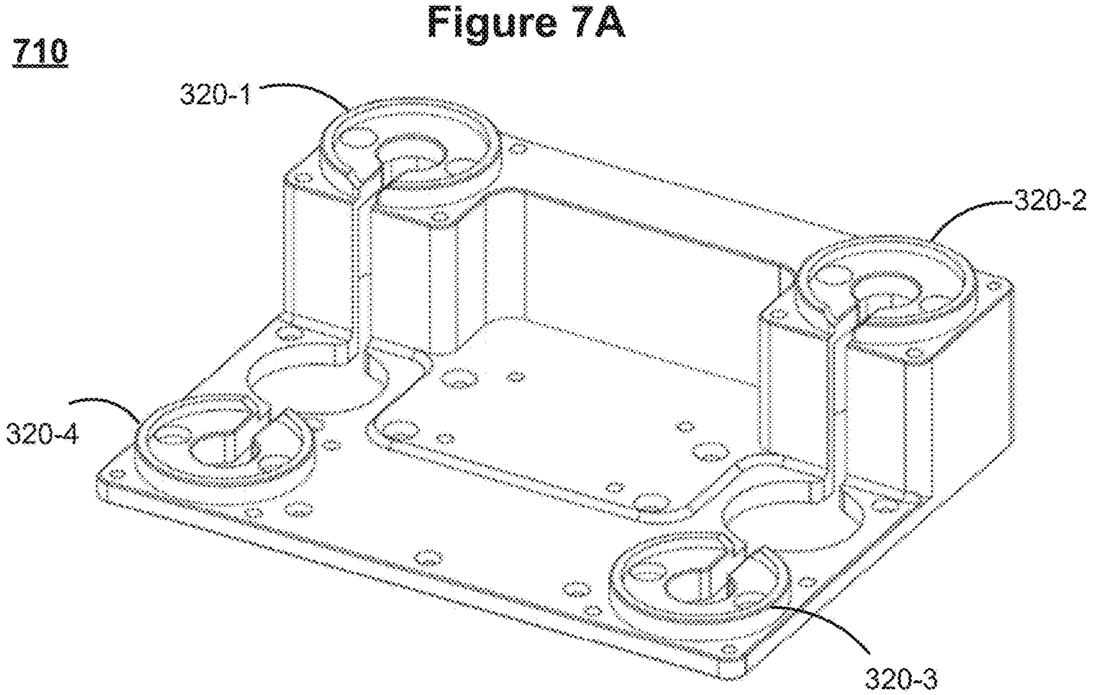
FIG. 7B is a perspective view illustrating an exemplary component of the exemplary cartridge of FIG. 7A.
Figure 7C:
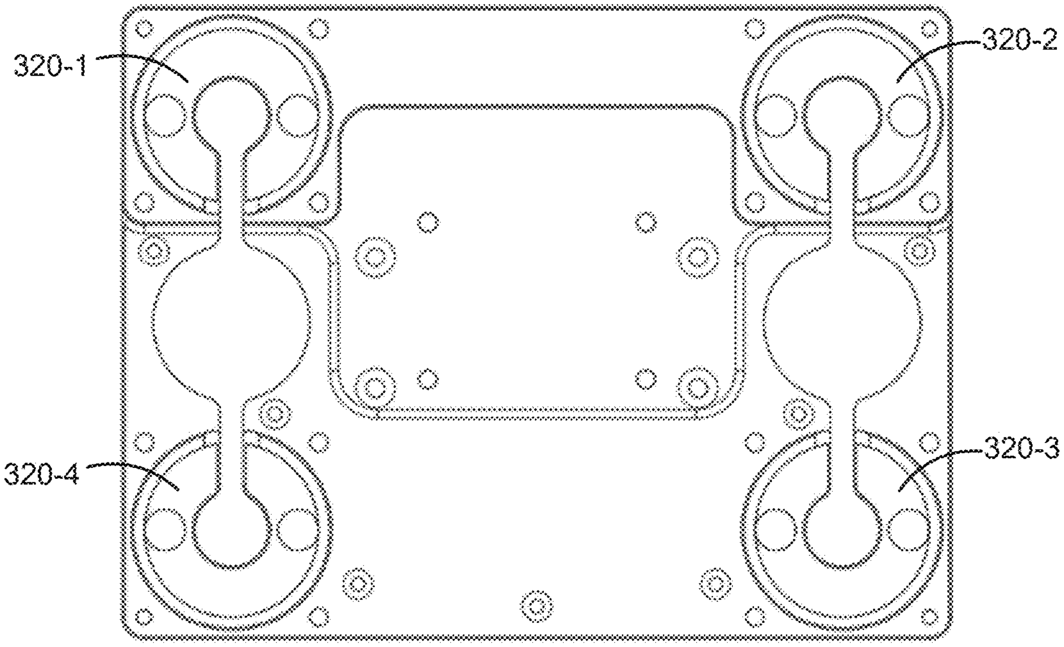
FIG. 7C is a top view illustrating the exemplary component of FIG. 7B.
Figure 7D:
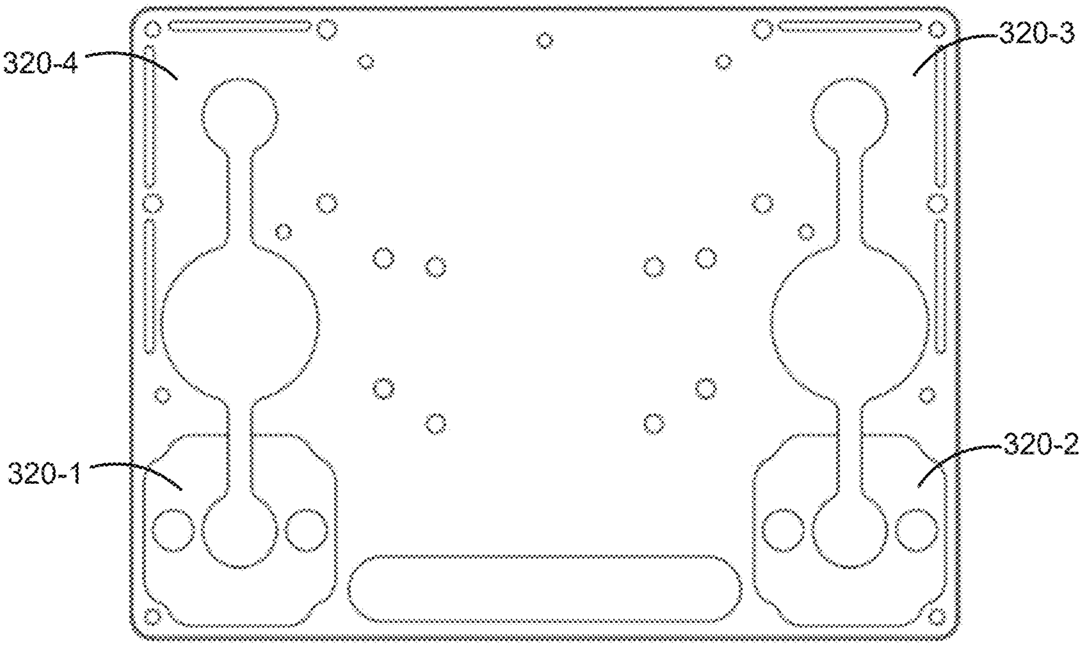
FIG. 7D is a bottom view illustrating the exemplary component of FIG. 7B.
Figure 8B:
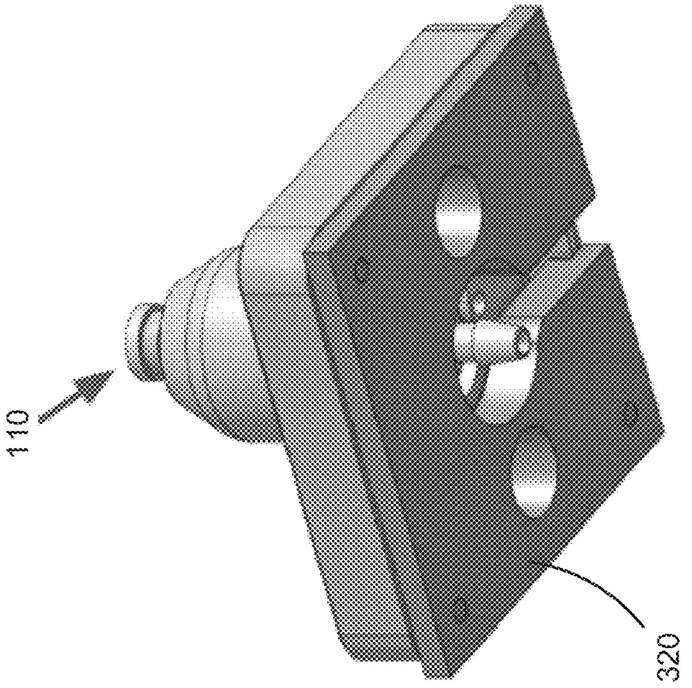
FIG. 8B is another perspective view illustrating the exemplary apparatus of FIG. 8A.
Figure 8A:
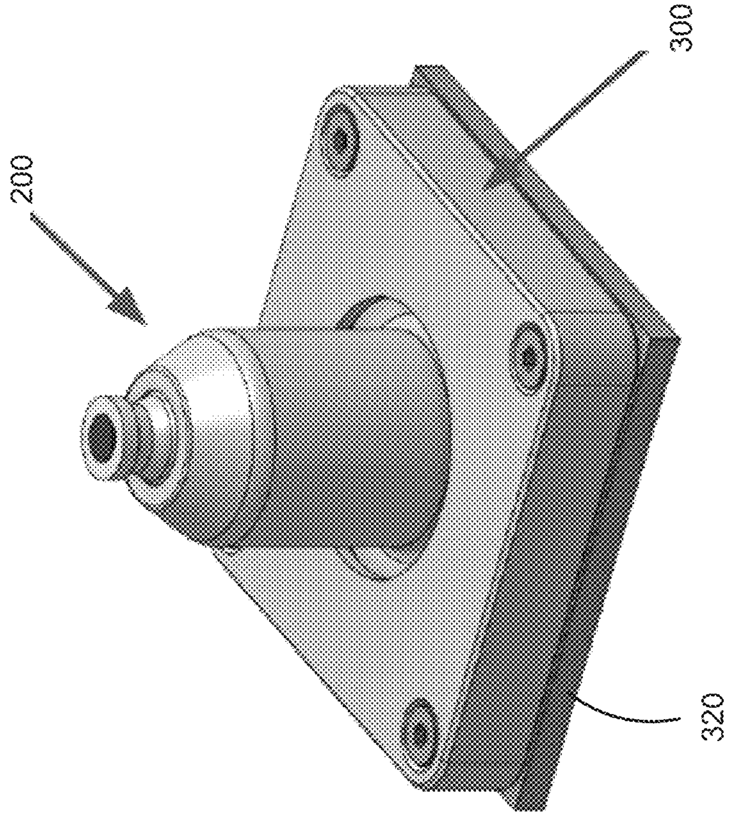
FIG. 8A is a perspective view illustrating an exemplary apparatus (also referred herein as a port assembly) in accordance with some exemplary embodiments of the present disclosure.
Figure 8D:
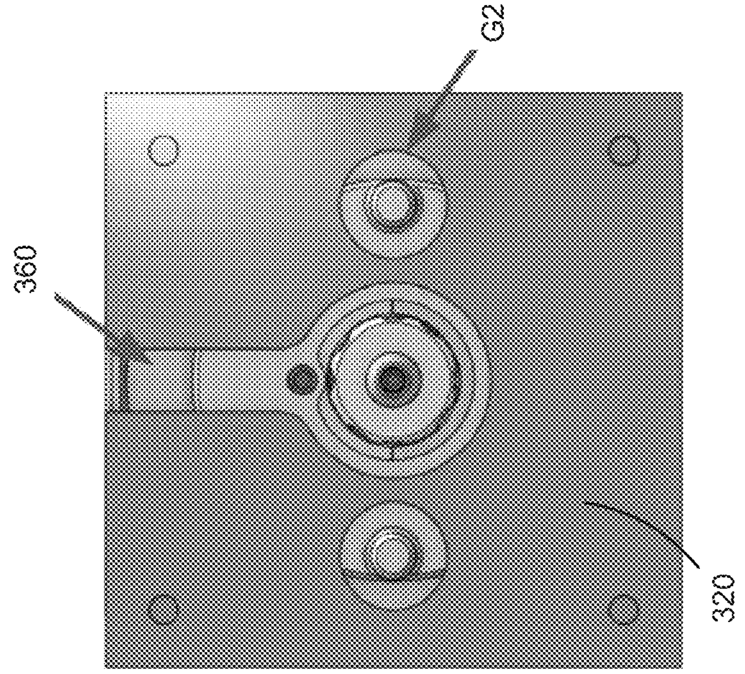
FIG. 8D is a bottom view illustrating the exemplary apparatus of FIG. 8A.
Figure 8C:
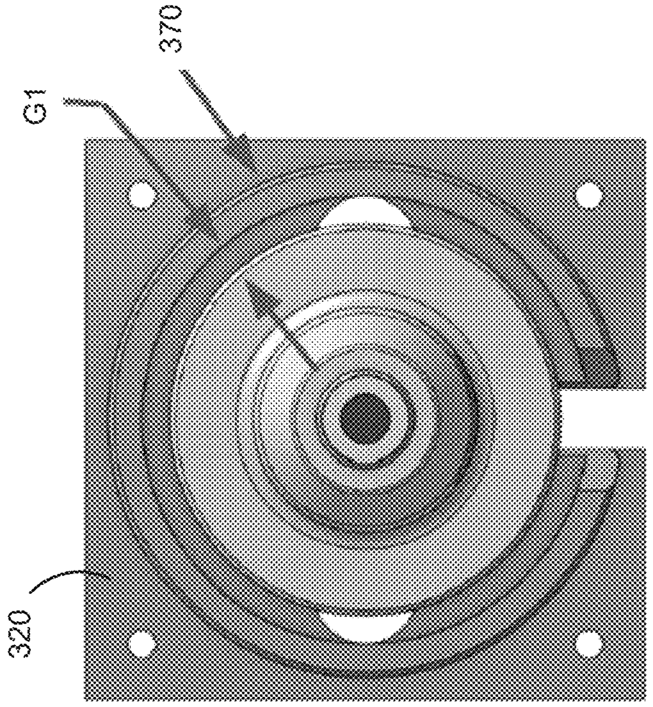
FIG. 8C is a top view illustrating the exemplary apparatus of FIG. 8A.

As a fourth non-limiting example, FIGS. 7A-7D illustrate an exemplary cartridge, generally designated 700, in accordance with some exemplary embodiments of the present disclosure. The cartridge includes an upper member 710 and a plurality of apparatuses 100, where the upper member is configured to serve as the second retaining members of the apparatuses and/or other functions. That is, the second retaining members of the plurality of apparatuses 100 are monolithically formed as a single piece, which is also a component (e.g., a wall) of the cartridge. Specifically, in the illustrated embodiment, the cartridge includes four apparatuses 100-1, 100-2, 100-3 and 100-4, and the upper member includes four second retaining members 320-1, 320-2, 320-3 and 320-4. The second retaining members 320-1 and 320-2 are identical or almost identical to each other, while the second retaining members 320-3 and 320-4 are identical or almost identical to each other. The second retaining members 320-1 and 320-2 are different from the second retaining members 320-3 and 320-4. For instance, as illustrated in FIGS. 7C and 7D, the second anti-rotation members formed at the second retaining members 320-1 and 320-2 are through-holes while the second anti-rotation members formed at the second retaining members 320-3 and 320-4 are blind holes.

As a fifth non-limiting example, FIGS. 8A-8D illustrate an exemplary apparatus 100 in accordance with some exemplary embodiments of the present disclosure. In this non-limiting example, the second retaining member 320 is shaped in a form of a plate.

Referring to FIGS. 9A-9C, there is depicted an exemplary apparatus, generally designated 900, in accordance with some exemplary embodiments of the present disclosure. In some embodiments, the apparatus 900 includes a port body, such as a port body 910, and a retainer, such as a retainer 920, coupled to each other. The port body is configured to grip a device, such as a coupler disclosed herein. The retainer is configured to retain the port body but allow the port body to move in a plane substantially perpendicular to an axial direction of the port body.

In some embodiments, the apparatus 900 is a coupler that includes both coupler gripping features for docking a coupler and a hollow tip to avoid contact with an embedded connector within the coupler. In some embodiments, the apparatus 900 is configured for making transfer connections with couplers, while others are just for locating and retaining (holding) couplers.

In some embodiments, the port body includes a base, a stem and a tip, such as a base 911, a stem 912, and a tip 913. The stem is extended from the base, and is generally cylindrical or substantially cylindrical, with at least a portion of the stem having a circular or substantially circular cross section. In some embodiments, the tip is a chamfered tip the same as or similar to the tip 240 disclosed here to aid the insertion of the port body into the device (e.g., the coupler 420). In some embodiments, the port body includes one or more engaging members are disposed on the stem of the port body for engaging the port body with the first device. In some embodiments, an engaging member in the one or more engaging members is a spring loaded ball plunger.

In some embodiments, the retainer 920 includes a first retaining member and a second retaining member, such as a first retaining member 921 and a second retaining member 922. The first retaining member and the second retaining member are coupled with each other, with the base of the port body disposed in between. A through-hole, such as a through-hole 912, is formed at the first retaining member. The first through-hole is configured to allow the stem of the port body to pass through and to move relative to the first retaining member but prevent the base of the port body from pulling out of the retainer via the first through-hole (e.g., the cross section of the first through-hole is larger than that of the stem but smaller than that of the base). This allows the port body to move relative to the retainer in a plane substantially perpendicular to an axial direction of the port body, and the movement of the port body is bounded the gap between the stem of the port body and the through-hole formed on the first retaining member (e.g., a gap between an outer surface of the stem and a surface of the first retaining member that defines the through-hole 923).

Figure 10B:
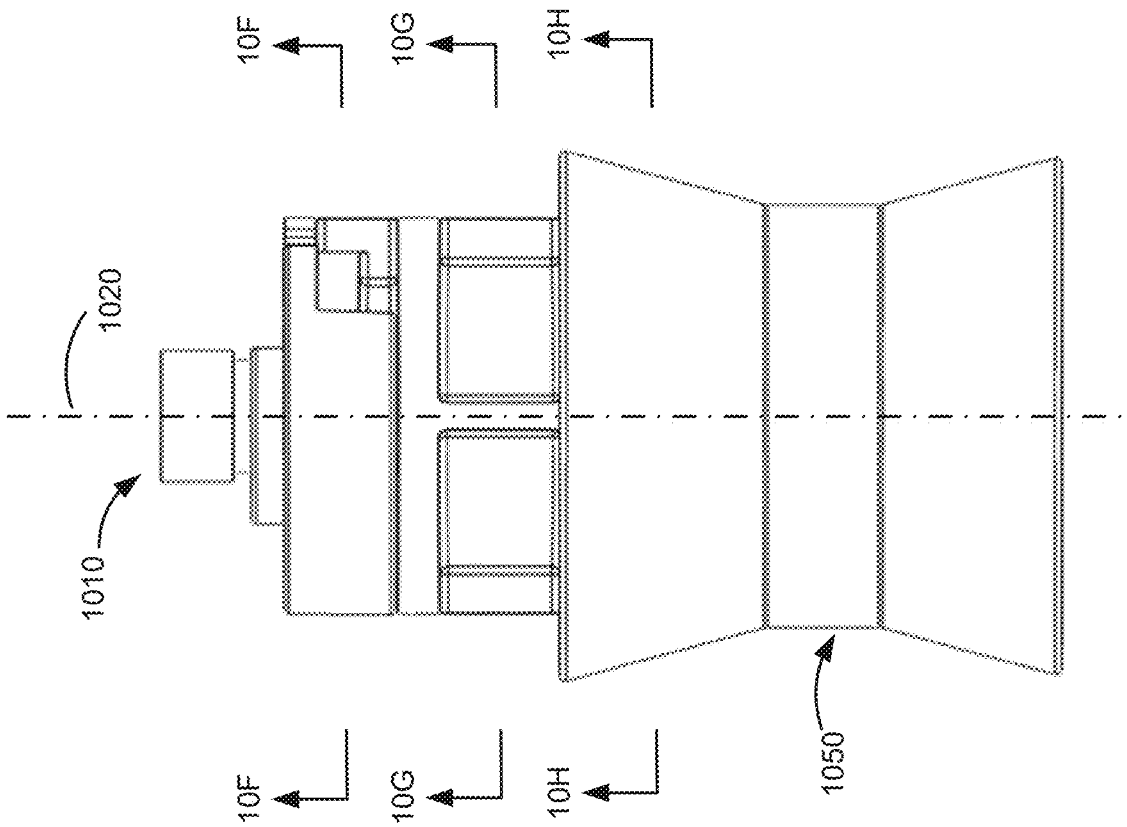
FIG. 10B is a side view illustrating the exemplary apparatus of FIG. 10A.
Figure 10A:
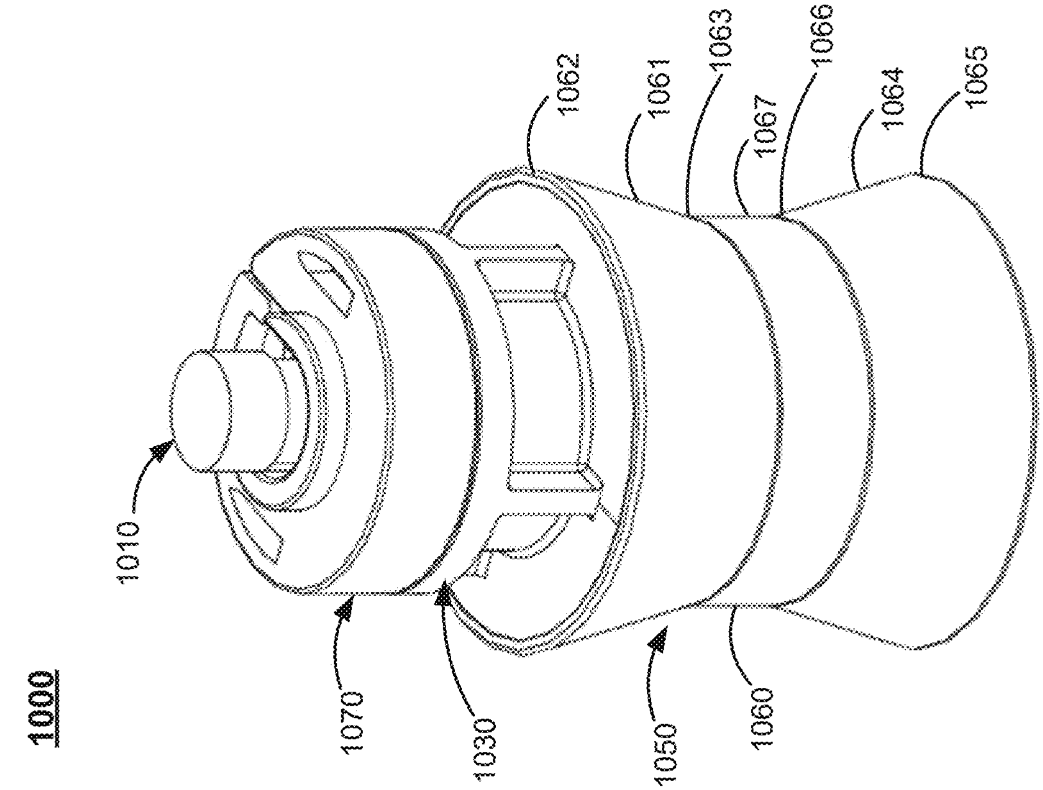
FIG. 10A is a perspective view illustrating an exemplary apparatus (also referred herein as a coupler) in accordance with some exemplary embodiments of the present disclosure.
Figure 10C:
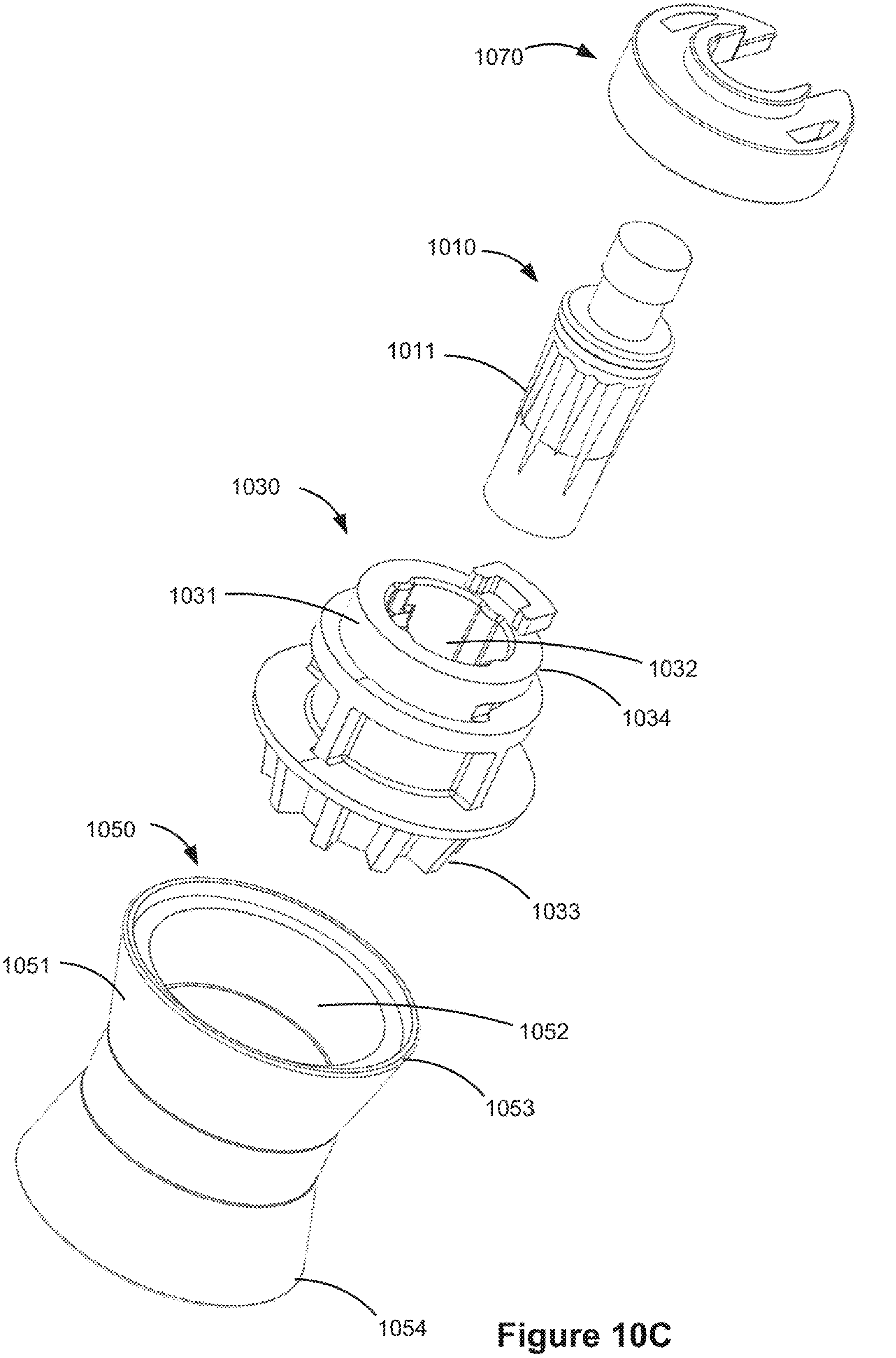
FIG. 10C is an exploded view illustrating the exemplary apparatus of FIG. 10A.
Figure 10E:
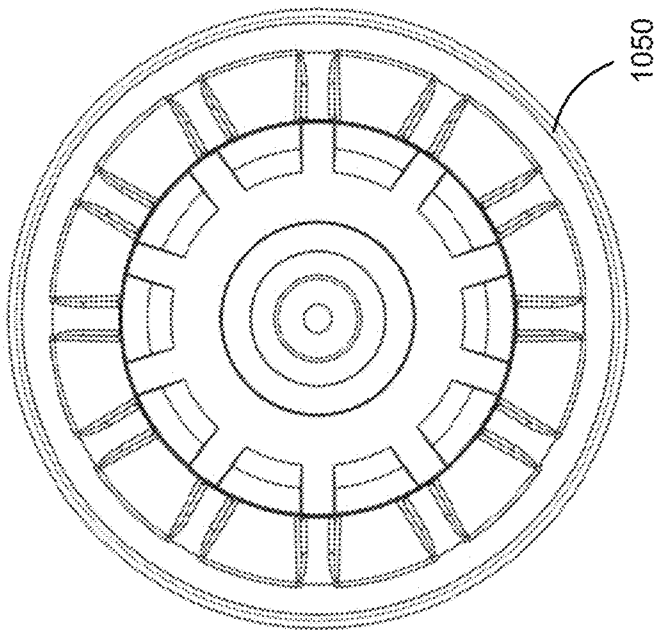
FIG. 10E is a bottom view illustrating the exemplary apparatus of FIG. 10A.
Figure 10D:
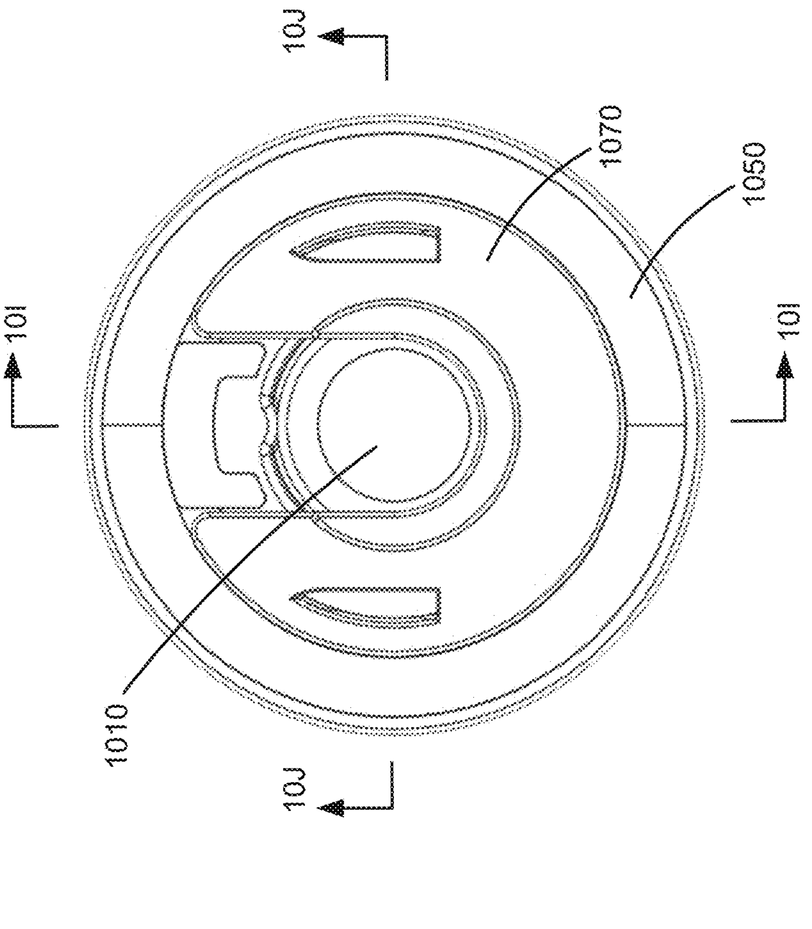
FIG. 10D is a top view illustrating the exemplary apparatus of FIG. 10A.
Figure 10F:
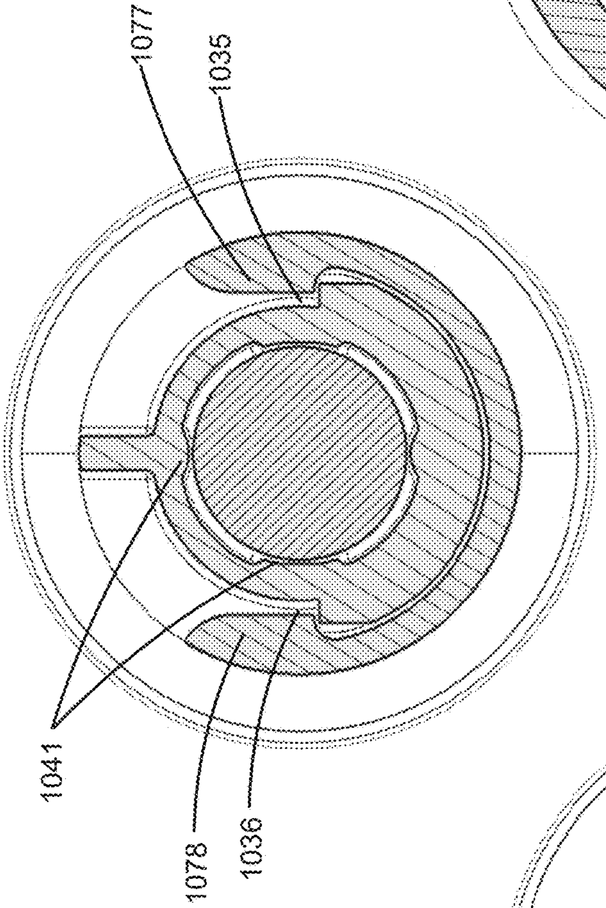
FIG. 10F is a cross-sectional view taken along line 10F-10F of FIG. 10B.
Figure 10H:
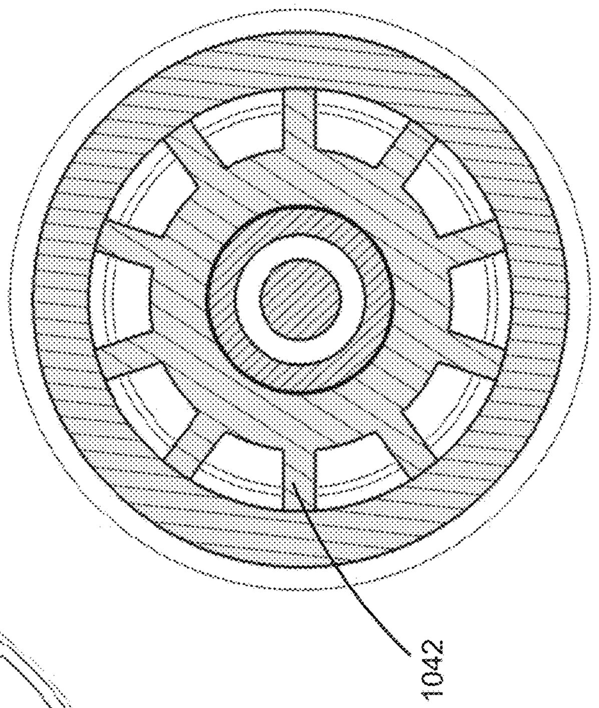
FIG. 10H is a cross-sectional view taken along line 10H-10H of FIG. 10B.
Figure 10G:
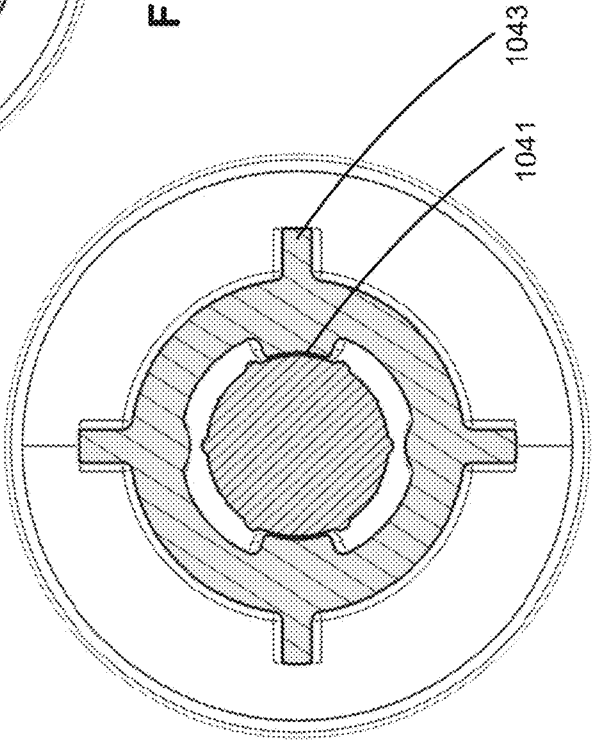
FIG. 10G is a cross-sectional view taken along line 10G-10G of FIG. 10B.
Figure 10J:
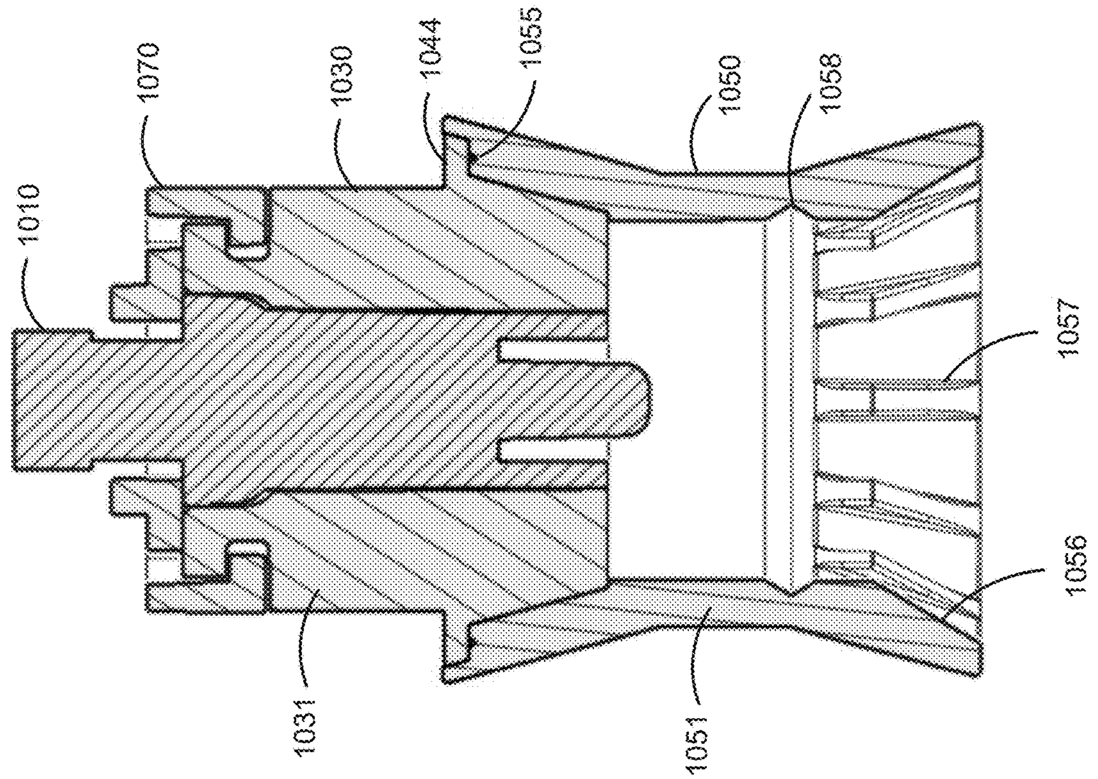
FIG. 10J is a cross-sectional view taken along line 10J-10J of FIG. 10D.
Figure 10I:
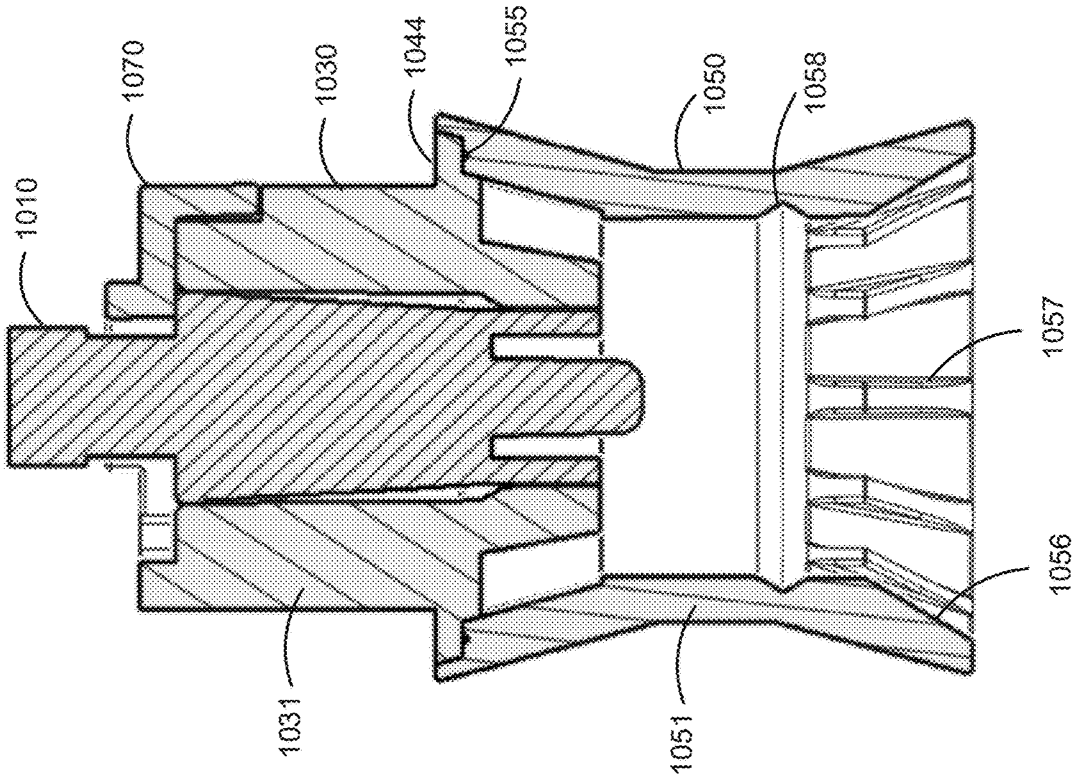
FIG. 10I is a cross-sectional view taken along line 10I-10I of FIG. 10D.
Figure 10L:
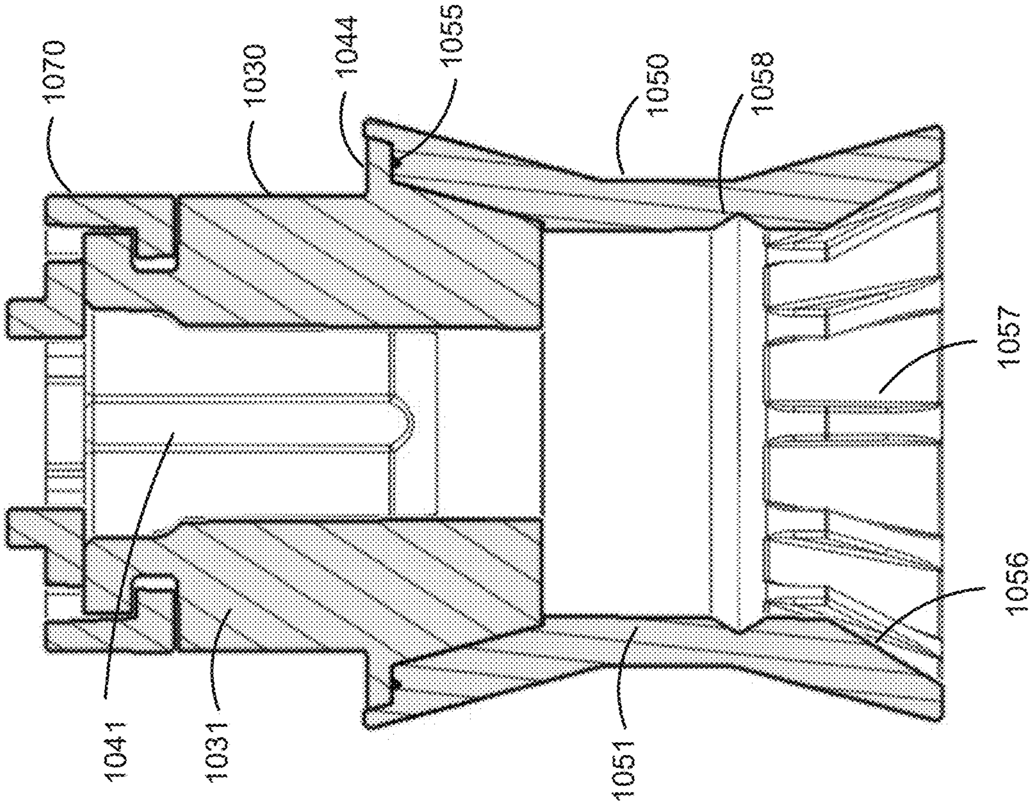
FIG. 10L is a cross-sectional view of FIG. 10J, where a connector is removed.
Figure 10K:
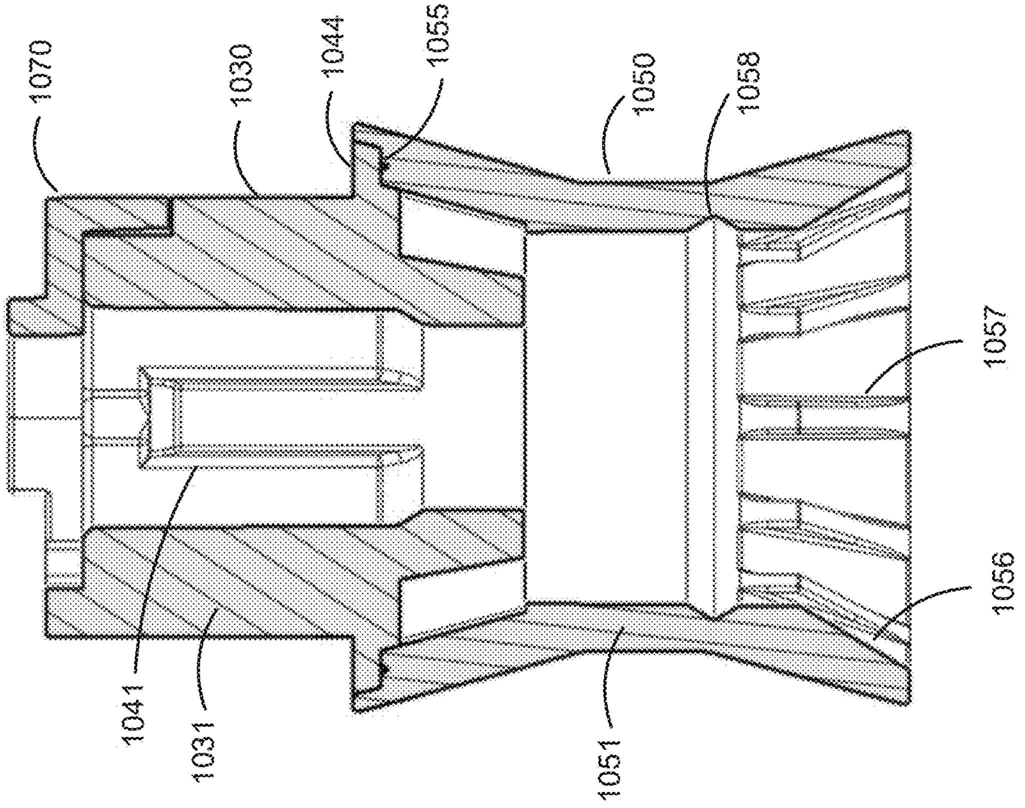
FIG. 10K is a cross-sectional view of FIG. 10I, where a connector is removed.
Figure 10N:
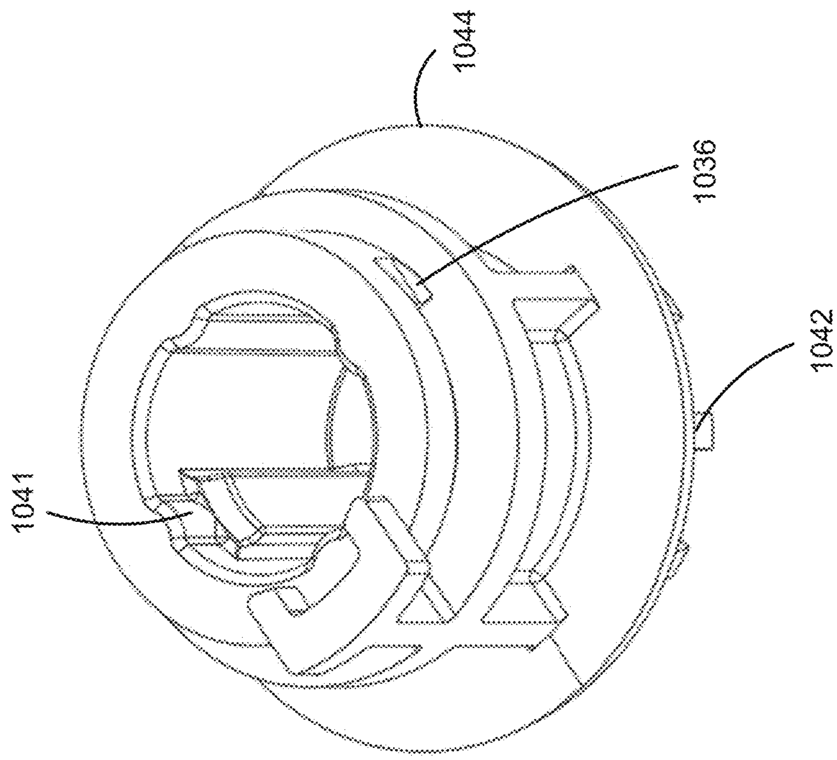
FIGS. 10M and 10N are perspective views illustrating an exemplary component of the exemplary apparatus of FIG. 10A in accordance with some exemplary embodiments of the present disclosure.
Figure 10M:
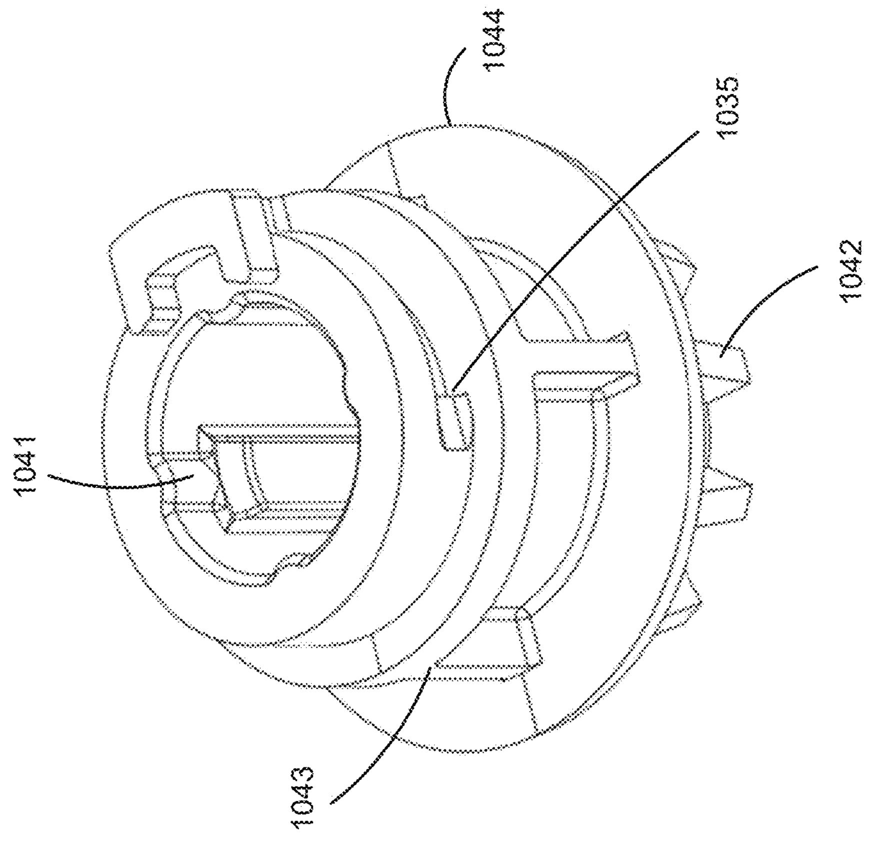
Figure 10P:
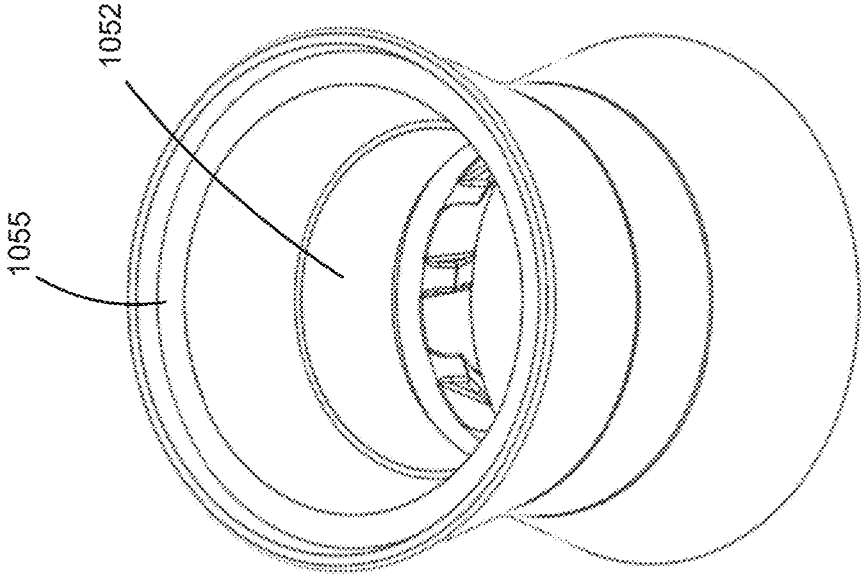
FIGS. 10O and 10P are perspective views illustrating another exemplary component of the exemplary apparatus of FIG. 10A in accordance with some exemplary embodiments of the present disclosure.
Figure 10O:
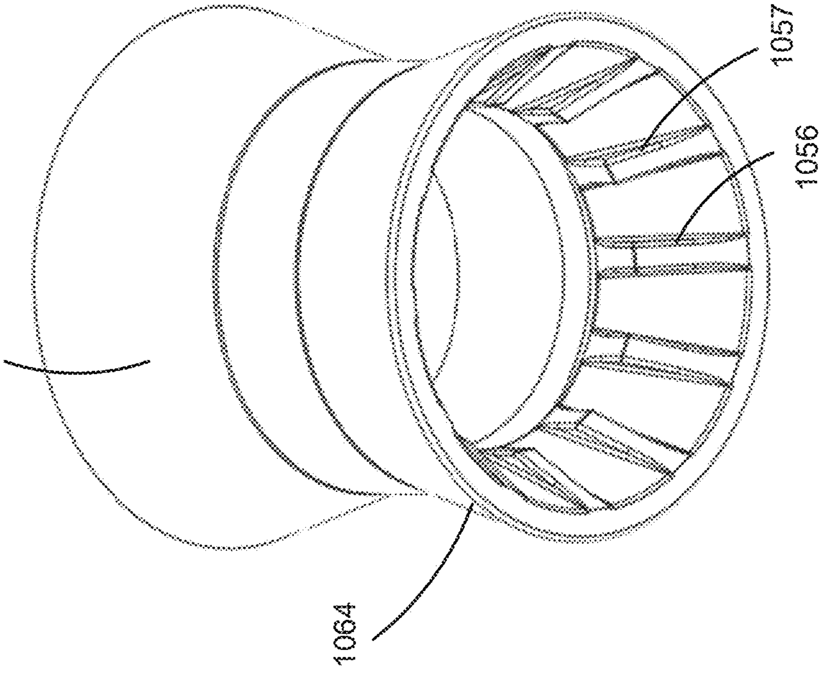
Figure 10Q:
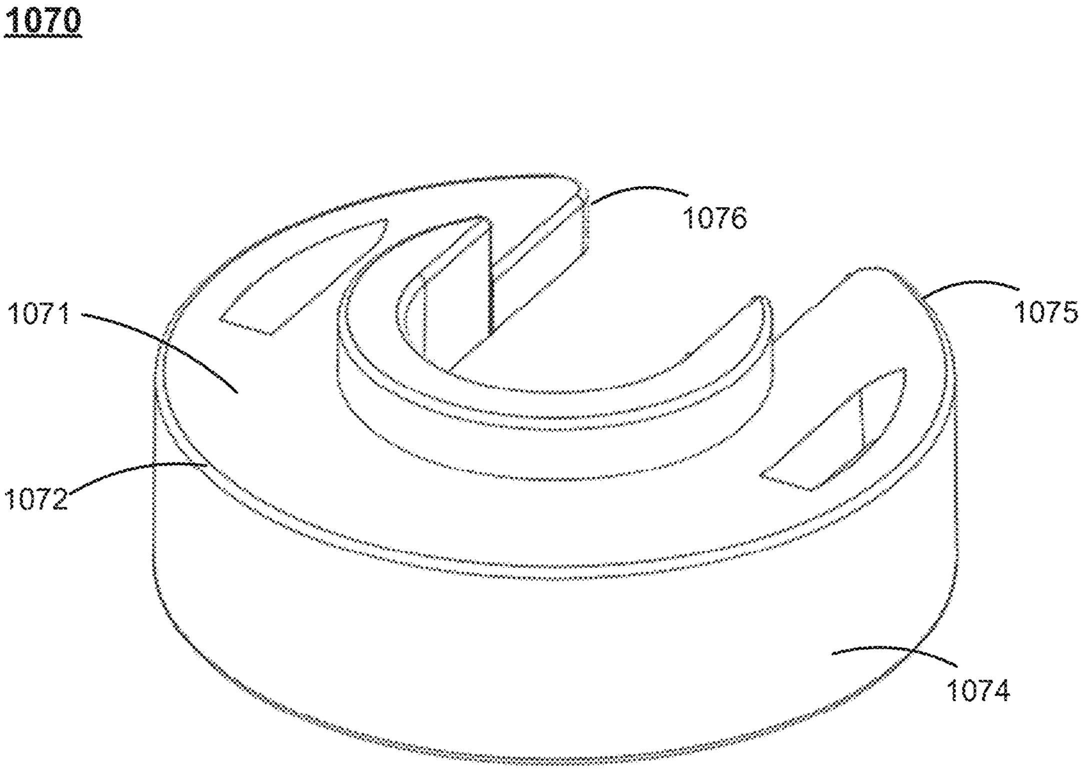
FIGS. 10Q and 10R are perspective views illustrating another exemplary component of the exemplary apparatus of FIG. 10A in accordance with some exemplary embodiments of the present disclosure.
Figure 10R:
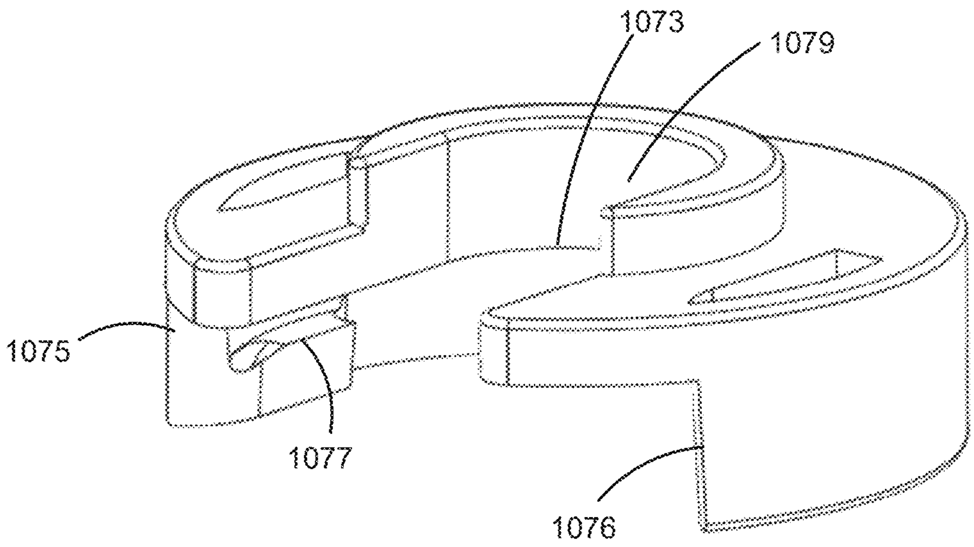

Referring to FIG. 10A-10R, there is depicted an exemplary apparatus, generally designated 1000, in accordance with some exemplary embodiments of the present disclosure. In various embodiments, the apparatus 1000 includes a dual function design with external drive and alignment features and internal features for compatibility with a variety of fluid and non-fluid connectors. Accordingly, the apparatus 1000 is also referred herein as a coupler. In some embodiments, one of the key innovations is the dual function aspect of the design that can convert a variety of industry standard connectors into robot-grippable-robot-drivable (twist) connectors with specific features to accommodate axial misalignment during mating with the corresponding port. In some embodiments, the apparatus 1000 is configured for facilitating automation of a connector, e.g., allowing a robot to operate the connector. The apparatus 1000 generally includes a first coupling member and a second coupling member connected to or formed with the first coupling member. The first coupling member is configured for holding a first device and the second coupling member is configured for coupling with a second device (e.g., a port body or a port assembly disclosed herein). The second coupling member is also configured to serve as a robotic operable interface for a robot, such as a robotic end of arm tool (EOAT), to grip, hold and/or rotate.

Referring in particular to FIGS. 10A and 10C, in some embodiments, the apparatus 1000 includes a first coupling member, such as the first coupling member 1030, and a second coupling member, such as the second coupling member 1050. The first coupling member includes a first side wall defining a first bore for receiving at least a portion of a first device. For instance, in some embodiments, the first coupling member 1030 includes a first side wall 1031 defining a first bore 1032 for receiving at least a portion of a first device 1010. In some embodiments, the first device 1010 is a fluid connector, a gas connector, an electrical connector, or any combination thereof.

In some embodiments, the first coupling member is connected to the first device by a retainer. For instance, in the illustrated embodiment, the first coupling member 1030 is connected to the first device 1010 by a retainer 1070. The retainer can be a component of the first device 1010 or a component of the apparatus 1000, and can be of any suitable shape and size. In some embodiments, the retainer 1070 is a clip having an open side to allow the clip to fit on the first coupling member.

For instance, referring in particular to FIGS. 10F, 10M-10N and 10Q-10R, in some embodiments, the first coupling member 1030 includes a first external recess and a second external recess, such as a first external recess 1035 and a second external recess 1036. The first and second external recesses are formed on the first side wall at or adjacent a distal end portion 1034 of the first coupling member. In some embodiments, each of the first and second external recesses is a circumferential groove. The retainer 1070 (e.g., the clip) includes an upper wall, an outer side wall, a first clip protrusion and a second clip protrusion, such as an upper wall 1071, an outer side wall 1074, a first clip protrusion 1077 and a second clip protrusion 1078. In some embodiments, the upper wall is configured for abutting a surface of the distal end portion of the first coupling member and a surface of the first device, thereby restricting the first device from moving relative to the first coupling member in a direction parallel or substantially parallel to the rotational axis of the apparatus. In some embodiments, the upper wall includes an outer curved edge and/or an inner curved edge, such as such as an outer curved edge 1072 and/or an inner curved edge 1073. The outer side wall extends downward from at least a portion of the outer curved edge of the upper wall and includes a first clip end and a second clip end, such as a first clip end 1075 and a second clip end 1076, at the open side of the clip. The first clip protrusion protrudes inward from the outer side wall at or adjacent to the first clip end and configured for engaging with the first external recess formed on the first side wall. The second clip protrusion protrudes inward from the outer side wall at or adjacent to the second clip end for engaging with the second external recess formed on the first side wall. In some embodiments, the clip further includes an inner side wall, such as an inner side wall 1079, extending upward from at least a portion of the inner curved edge of the upper wall to assist in retaining the first device. However, the present disclosure is not limited thereof. The first coupling member and the clip can include additional, optional or alternative components, and can be coupled with each other by other means.

In some embodiments, the first coupling member 1030 includes a mechanism to restrict the first device from rotating relative to the first coupling member around the rotational axis of the apparatus. For instance, referring in particular to FIGS. 10F-10N, in some embodiments, the first coupling member includes a plurality of first internal ribs, such as first internal ribs 1041, formed on the first side wall and distributed circumferentially around the rotational axis of the apparatus. The plurality of first internal ribs is configured for abutting an external side wall 1011 of the first device, thereby restricting the first device from rotating relative to the first coupling member around the rotational axis of the apparatus.

In some embodiments, the first coupling member 1030 includes one or more external strengthening members, such as external strengthening members 1043. The one or more external strengthening members are formed on the first side wall of the first coupling member to enhance the strength of the first coupling member. An external strengthening member can be of any type (e.g., rim, rib) and of any shape and size. In some embodiments, the one or more external strengthening members include one or more external rims, one or more external ribs, or any combination thereof. Advantageously, by including one or more external strengthening members, material can be cored out so that the first coupling member can be configured with a uniform or substantially uniform wall thickness for injection molding.

Referring in particular to FIGS. 10A, 10C and 10O-10P, the second coupling member 1050 is connected to or formed with the first coupling member at a proximal end portion of the first coupling member. As used herein, a proximal end portion of the first coupling member (e.g., a proximal end portion 1033) refers to a portion of the first coupling member that is closer to the second coupling member and a distal end portion of the first coupling member (e.g., a distal end portion 1034) refers to a portion of the first coupling member that is away from the second coupling member. Similarly, a proximal end portion (e.g., a proximal end portion 1053) of the second coupling member refers to a portion of the second coupling member that is closer to the first coupling member and a distal end portion (e.g., a distal end portion 1054) of the second coupling member refers to a portion of the second coupling member that is away from the first coupling member. In the embodiment illustrated in FIGS. 10A and 10B, the proximal end portion of the first coupling member is a lower end portion of the first coupling member and a distal end portion of the first coupling member is an upper end portion of the first coupling member. The proximal end portion of the second coupling member is an upper end portion of the second coupling member and a distal end portion of the second coupling member is a lower end portion of the first coupling member.

In some embodiments, the second coupling member 1050 includes a second side wall, such as a second side wall 1051. The second side wall defines a second bore, such as a second bore 1052. In some embodiments, the first coupling member and the second coupling member are individual parts, for instance, each formed by an injection molding of a plastic (e.g., a medical grade plastic). The first coupling member and the second coupling member are connected to each other, for instance, by ultrasonic welding, adhesive bonding, or other means. In some embodiments, the proximal end portion of the first coupling member is inserted into the proximal end portion of the second coupling member, e.g., inserted into a portion of the second bore formed at the proximal end portion of the second coupling member. The first coupling member includes an external flange, such as an external flange 1044, at or adjacent the proximal end portion 1033 of the first coupling member. The second coupling member includes a shoulder, such as a shoulder 1055, at or adjacent the proximal end portion of the second coupling member. The shoulder of the second coupling member is configured to hold the external flange of the first coupling member. The external flange of the first coupling member and the shoulder of the second coupling member are connected to each other, for instance, by ultrasonic welding, adhesive bonding, or other means.

In some embodiments, at least one of the first coupling member 1030 and the second coupling member 1050 includes a mechanism to assist in securing the first coupling member with the second coupling member. For instance, referring in particular to FIGS. 10H and 10M-10N, in some embodiments, the proximal end portion of the first coupling member includes a plurality of first external ribs, such as first external ribs 1042. The plurality of first external ribs is formed on the first side wall and distributed circumferentially around the rotational axis of the apparatus for abutting the proximal end portion of the second coupling member, e.g., abutting an inner surface of the proximal end portion of the second coupling member, thereby help to secure the first coupling member with the second coupling member.

Referring in particular to FIG. 10A, in various embodiments, the second side wall 1051 of the second coupling member has an exterior surface defined by revolving a continuous curve about a rotational axis of the apparatus to facilitate operation by a robotic arm. For instance, in some embodiments, the second side wall has an exterior surface 1060 defined by revolving a continuous curve about a rotational axis, such as a rotational axis 1020, of the apparatus. A continuous curve can be a smooth curve, a piecewise smooth curve, or a non-smooth curve. As a non-limiting example, it is illustrated that the exterior surface 1060 is defined by revolving a piecewise smooth curve comprised of three smooth segments, each being a substantially straight line.

In some embodiments, the revolving exterior surface includes a first revolving segment, such as a first revolving segment 1061, proximal to the first coupling member. The revolving exterior surface also includes a second revolving segment, such as a second revolving segment 1064, distal to the first coupling member. The first and second revolving segments of the revolving exterior surface can be but do not have to be identical or symmetrical to each other. As a non-limiting example, the first and second revolving segments of the revolving exterior surface are illustrated to be identical or substantially identical (e.g., substantially the same in size and shape).

In some embodiments, each of the first and second revolving segments of the revolving exterior surface has a first side and a second side that is narrower than the first side. For instance, the first revolving segment 1061 has a first side 1062 and a second side 1063 that is narrower than the first side 1062, and the second revolving segment 1064 has a first side 1065 and a second side 1066 that is narrower than the first side 165. The second sides of the first and second revolving segments of the revolving exterior surface (e.g., the second side 1063 and the second side 1065) face each other.

In some embodiments, the first or second revolving segment of the revolving exterior surface is a non-cylindrical segment. In some embodiments, each of the first and second revolving segments of the revolving exterior surface is a non-cylindrical segment. For instance, in an exemplary embodiment, one of the first and second revolving segments of the revolving exterior surface is a conical or substantially conical surface (e.g., a revolving surface defined by a slanted straight or substantially straight line), and the other of the first and second revolving segments of the revolving exterior surface is an inverted conical or substantially conical surface. In some embodiments, the revolving exterior surface further includes a third revolving segment, such as a third revolving segment 1067. The third revolving segment is disposed between the first and second revolving segments and connects the second side of the first revolving segment with the second side of the second revolving segment. In an exemplary embodiment, the third revolving segment of revolving exterior surface is a cylindrical or substantially cylindrical surface (e.g., a revolving surface defined by a straight or substantially straight line). However, the present disclosure is not limited thereto. The revolving exterior surface can have other shapes. For instance, the revolving exterior surface can include a single revolving segment or more than three revolving segments.

Referring in particular to FIGS. 10I-10L and 10O-10P, the second bore 1052 of the second coupling member is configured to receive at least a portion of a second device, such as a port body or a port assembly disclosed herein. In some embodiments, the second coupling member 1050 includes an internal chamfer, such as an internal chamfer 1056. The internal chamfer is formed at the second end portion of the second coupling member and configured to guide connection of the apparatus 1000 with the second device (e.g., the port body 200, 400, or 500). In some embodiments, the second coupling member includes a plurality of second internal ribs, such as second internal ribs 1057. The plurality of second internal ribs is on the second side wall of the second coupling member and distributed circumferentially around the rotational axis of the apparatus. In some such embodiments, the internal chamfer is formed collectively by the plurality of second internal ribs, e.g., the plurality of second internal ribs defines the chamfer angle and chamfer length of the internal chamfer. Like the one or more strengthening members of the first coupling member, the plurality of second internal ribs advantageously allows for the design of the second coupling member with a substantially uniform wall thickness while meeting required strength and/or other properties.

In some embodiments, the second coupling member 1050 includes a recess, such as a recess 1058, formed circumferentially on the second side wall (e.g., an inner surface of the second side wall) of the second coupling member at or adjacent the internal chamfer. The recess can have any suitable shape and size. In an exemplary embodiment, the recess 1058 is a tapered internal recess. The recess in general will reduce the stiffness of the second coupling member and thus facilitate smooth interaction between the apparatus and the second device.

Referring to FIGS. 11A-11F, there is depicted an exemplary robotic end of arm tool (EOAT), generally designated 1100, in accordance with some exemplary embodiments of the present disclosure. In some embodiments, the robotic EOAT includes a robotic grasp and rotate structure that allows for grasping a device and rotating the device once grasped by the robotic EOAT. In some embodiments, this robotic EOAT includes the combination of axial grasping with position control along the rotation axis, and the simultaneous ability to rotate the grasped part (e.g., a coupler, a port, etc.) via a friction drive wheel against one or more exterior surfaces of the part (hold and rotate the part while the EOAT body remains stationary), such as a first surface or at least two surfaces. However, the present disclosure is not limited thereto.

In some embodiments, this robotic EOAT includes a motor, such as a dual tire drive wheel, and a pair of bifurcated angular actuated jaws with ball transfers at each end portion thereof, which provide at least two separate mechanical circuits of at least three points contact with the grasped part (e.g., a coupler, a port, a syringe, etc.). In some embodiments, the at least two ball transfers are positioned on the same plane as each drive wheel tire of the motor. In this way, the grasp of the EOAT on the part is very stable as it simultaneously draws the upper and lower halves of the part inward towards the drive wheel. However, the present disclosure is not limited thereto.

In some embodiments, this robotic EOAT is configured for operating a part that includes a revolving exterior surface around a rotational axis of the part. In some embodiments, the revolving exterior surface includes a first non-cylindrical segment and a second non-cylindrical segment. For instance, in some embodiments, the part is configured the same as or similarly to the apparatus 1000, which includes the revolving exterior surface 1060 having a first non-cylindrical segment 1061 and a second non-cylindrical segment 1064.

In some embodiments, the robotic EOAT includes a support, a first jaw, a second jaw, and a wheel, such as a support 1110, a first jaw 1120, a second jaw 1130, and a wheel 1140. In some embodiments, the first jaw, the second jaw and the wheel are disposed at a side of the support.

The first jaw and the second jaw are connected to the support and operable between an open position and a closed position for gripping and releasing the part (e.g., the coupler 1000). The first and second jaws can be but do not have to be identical or substantially symmetrical to each other with respect to the wheel. As a non-limiting example, the first and second jaws are illustrated to be substantially the same and substantially symmetrical to each other with respect to the wheel.

In some embodiments, to facilitate gripping and/or rotating of the part (e.g., the coupler 1000), each of the first and second jaws includes a first contact bearing and a second contact bearing. In some embodiments, each of the first and second jaws is split like a split finger or fork. For instance, in an exemplary embodiment, the first jaw 1120 includes a first contact bearing 1121 and a second contact bearing 1122, and the second jaw 1130 includes a first contact bearing 1131 and a second contact bearing 1132. A bearing in the first and second contact bearings of the first and second jaws can be any suitable type of bearings including but not limited to a ball of a ball transfer unit. The first and second contact bearings of the first or second jaw can be but do not have to be aligned in a direction substantially parallel to the rotational axis of the wheel. As a non-limiting example, it is illustrated that the first and second contact bearings of the first jaw are aligned with each other in a direction substantially parallel to the rotational axis of the wheel, and the first and second contact bearings of the second jaw are aligned with each other in a direction substantially parallel to the rotational axis of the wheel.

In some embodiments, each of the first and second jaws includes a jaw surface, and the first and second contact bearings are disposed at the jaw surface. For instance, in some embodiments, the first jaw 1120 includes a first jaw surface 1123, at which the first contact bearing 1121 and the second contact bearing 1122 are disposed. Similarly, the second jaw 1130 includes a second jaw surface 1133, at which the first contact bearing 1131 and the second contact bearing 1132 are disposed.

Figure 11A:
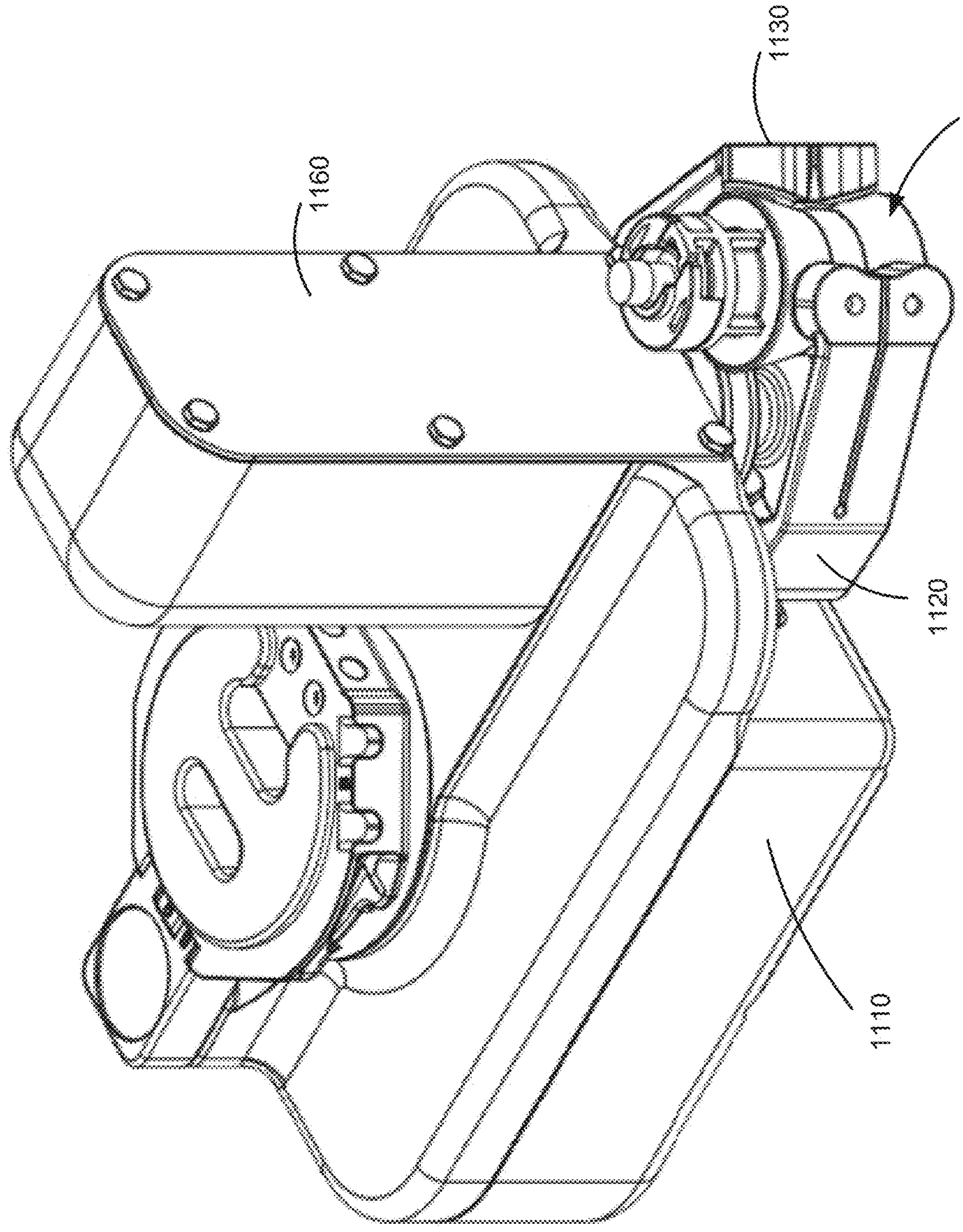
FIG. 11A is a perspective view illustrating an exemplary robotic end of arm tool (EOAT) for operating the exemplary apparatus of FIG. 10A in accordance with some exemplary embodiments of the present disclosure.
Figure 11B:
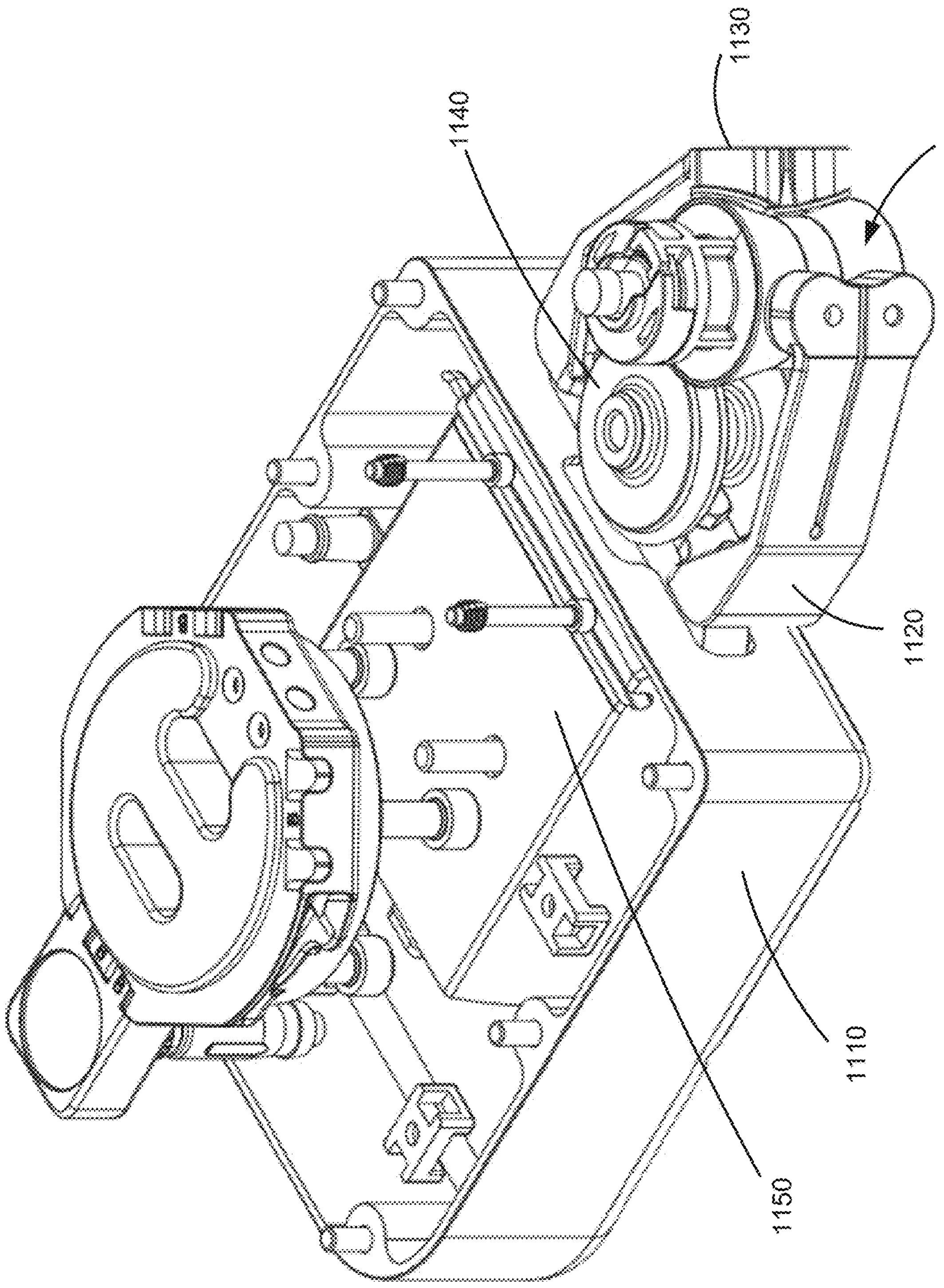
FIG. 11B is a perspective view illustrating the exemplary EOAT of FIG. 11A, where some components are removed to show an interior of the exemplary EOAT of FIG. 11A.
Figure 11C:
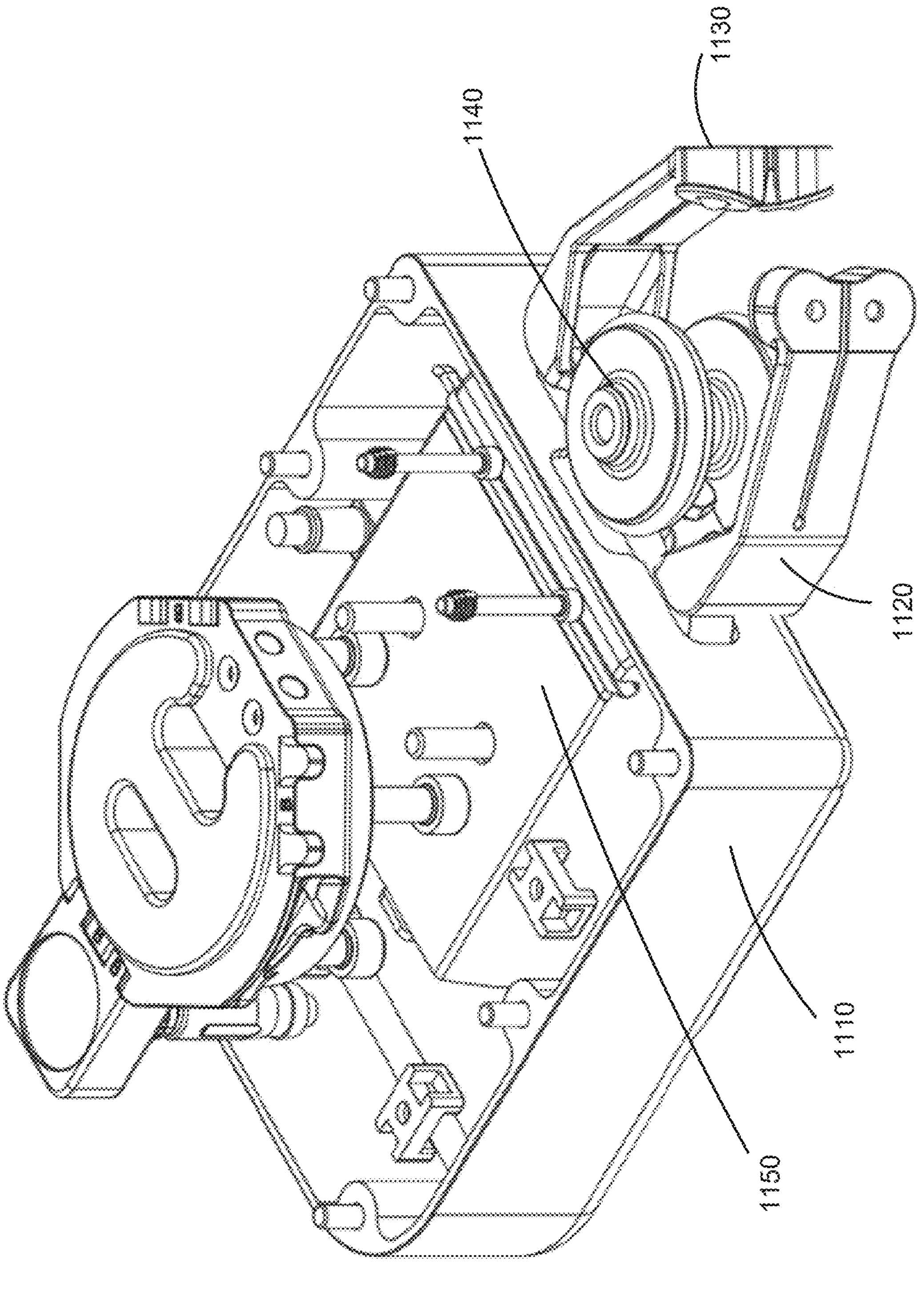
FIG. 11C is a perspective view illustrating the exemplary EOAT of FIG. 11B, where the exemplary apparatus of FIG. 10A is removed.
Figure 11D:
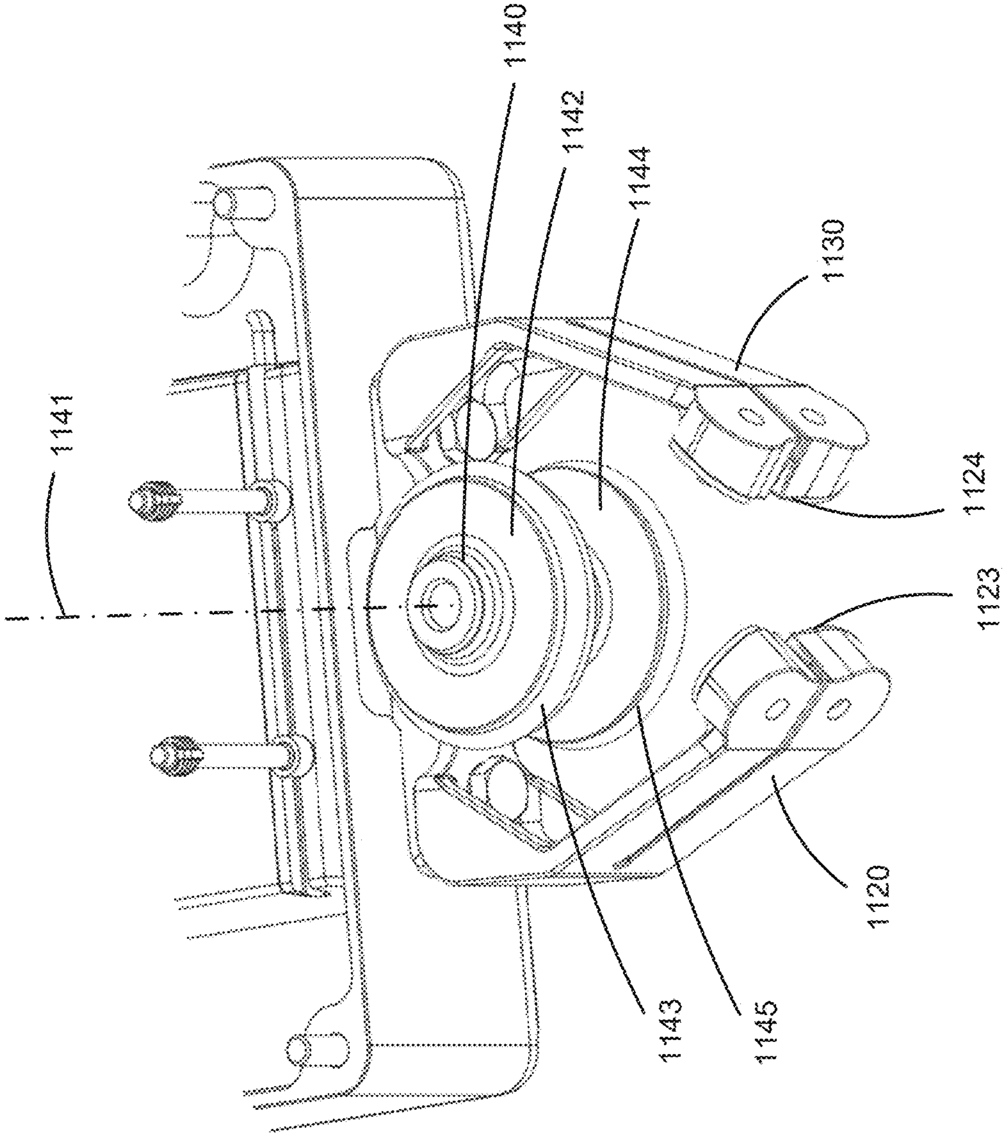
FIG. 11D is a perspective view illustrating a portion of the exemplary EOAT of FIG. 11C.
Figure 11E:
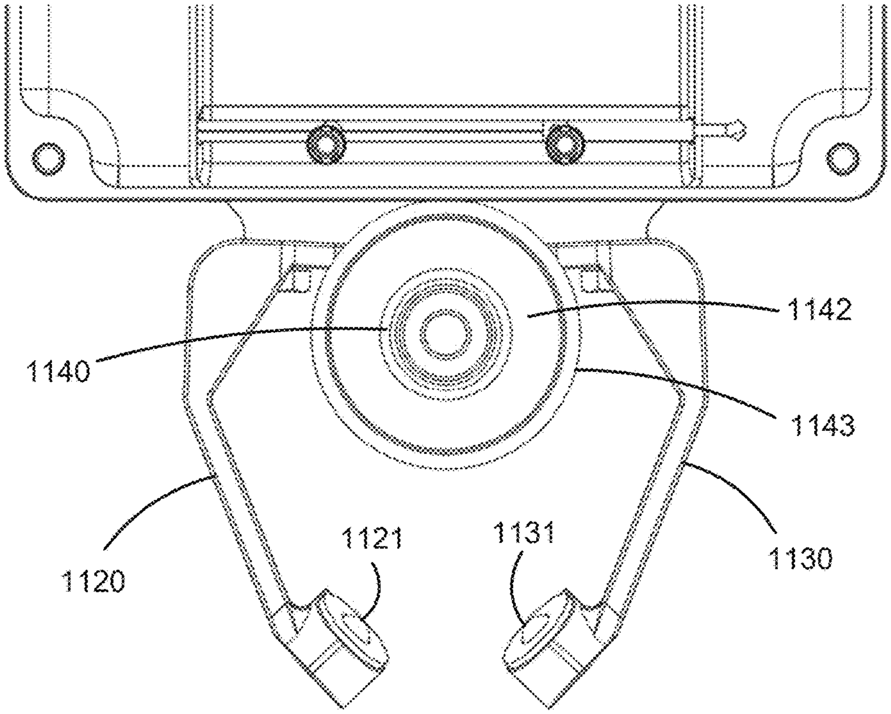
FIG. 11E is a top view illustrating a portion of the exemplary EOAT of FIG. 11C.
Figure 11F:
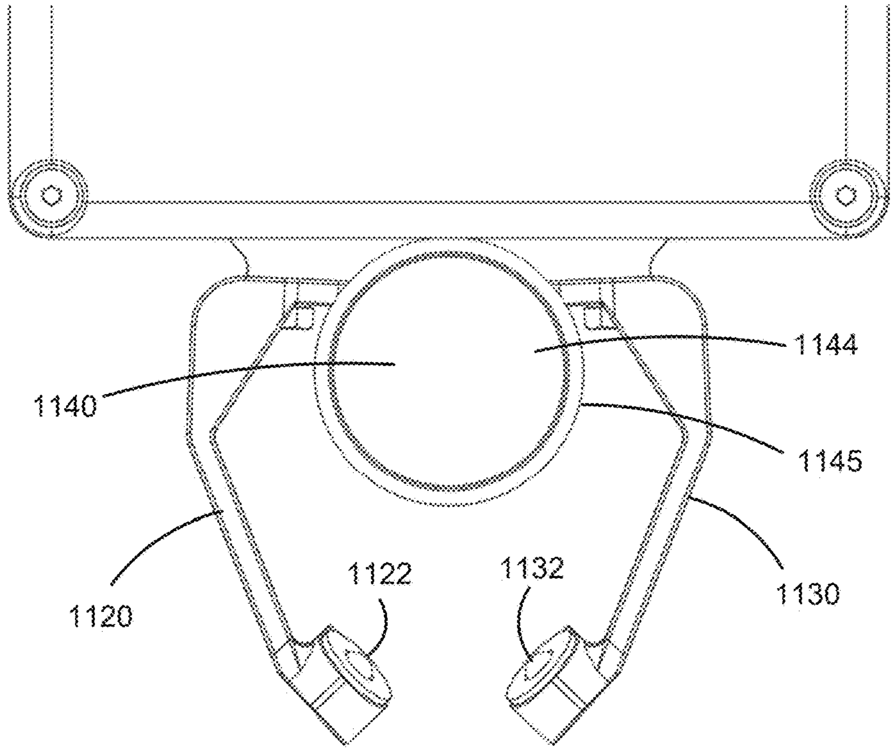
FIG. 11F is a bottom view illustrating a portion of the exemplary EOAT of FIG. 11C.

In some embodiments, to further assist in gripping and/or rotating of the part (e.g., the coupler 1000), the first or second jaw surface is profiled in accordance with the revolving exterior surface of the part (e.g., the revolving exterior surface 1060 of the coupler 1000). For instance, in some embodiments, each of the first and second jaw surfaces includes a first segment and a second segment profiled respectively in accordance with the first revolving segment 1061 and second revolving segment 1064 of the revolving exterior surface of the part as illustrated in FIGS. 11A and 11B.

The wheel is connected to the support and operable to rotate around a rotational axis, such as a rotational axis 1141, of the wheel. In some embodiments, the wheel includes a first rim and a second rim, such as a first rim 1142 and a second rim 1144. In some embodiments, each of the first and second rims of the wheel includes a tire. For instance, the first rim 1142 includes a first tire 1143 and the second rim 1144 includes a second tire 1145. The first and second tires can be made of any suitable material including but not limited to silicone rubber. In some embodiments, the first or second tire is an O-ring.

When the first and second jaws are in the closed position with the part (e.g., the coupler 1000) in between, the first contact bearing of the first jaw, the first contact bearing of the second jaw and the first rim of the wheel are leveled substantially with each other and abut the first non-cylindrical segment of the revolving exterior surface of the part (e.g., the coupler 1000). Similarly, the second contact bearing of the first jaw, the second contact bearing of the second jaw and the second rim of the wheel are leveled substantially with each other and abut the second non-cylindrical segment of the revolving exterior surface of the part (e.g., the coupler 1000). This not only restricts the part (e.g., the coupler 1000) from moving axially but also restricts the part (e.g., the coupler 1000) from moving translationally in a plane substantially perpendicular to the rotational axis of the part (e.g., the coupler 1000). In the meantime, this allows the wheel to rotate the part (e.g., the coupler 1000) to rotate around the rotational axis of the part (e.g., the coupler 1000), thereby facilitating connection of the device held by the part (e.g., the device 1010 held by the coupler 1000) with another device (e.g., the device 110 held by a port body disclosed herein).

In some embodiments, the robotic EOAT includes additional, optional or alternative components. For instance, in some embodiments, the robotic EOAT includes an actuator, such as an actuator 1150, to open and close the first and second jaws, a motor, such as a motor 1160, to drive the wheel, or both of the actuator and the motor. In some such embodiments, the first and second jaws are connected to the support through the actuator, and the wheel is connected to the support through the motor.

Figure 12A:
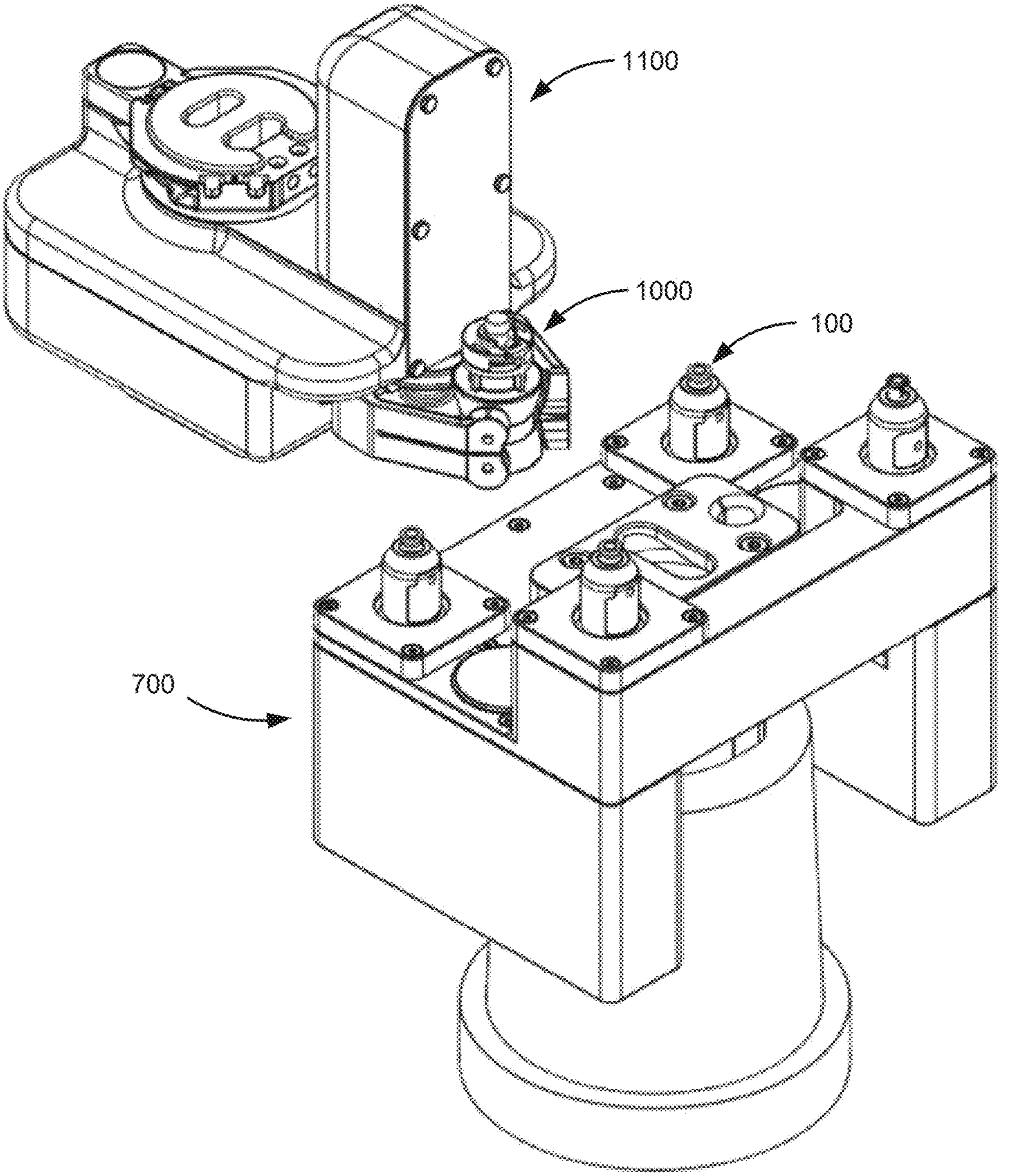
FIGS. 12A and 12B are perspective views illustrating an exemplary process for connecting two devices in accordance with some exemplary embodiments of the present disclosure.
Figure 12B:
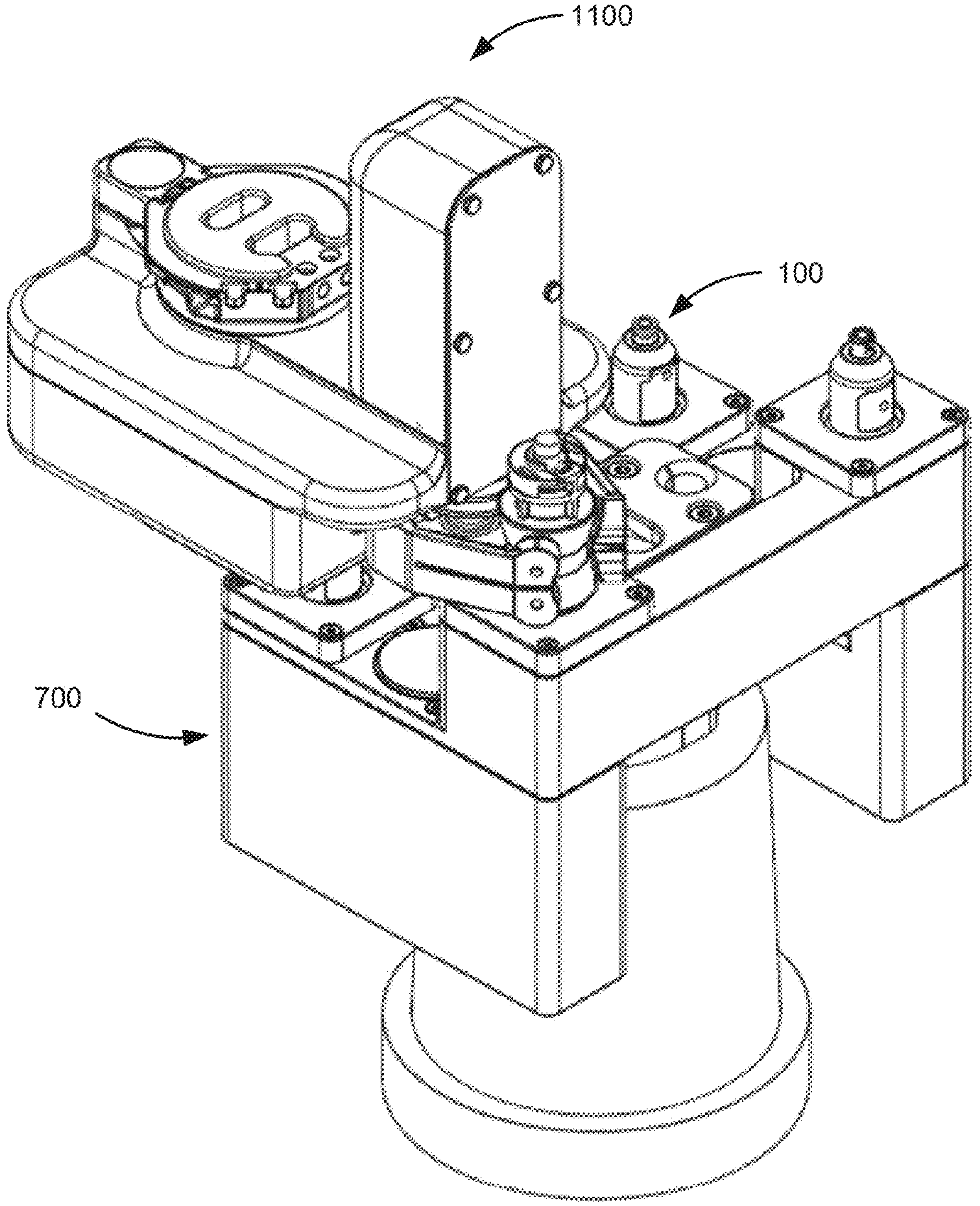
Figure 12C:
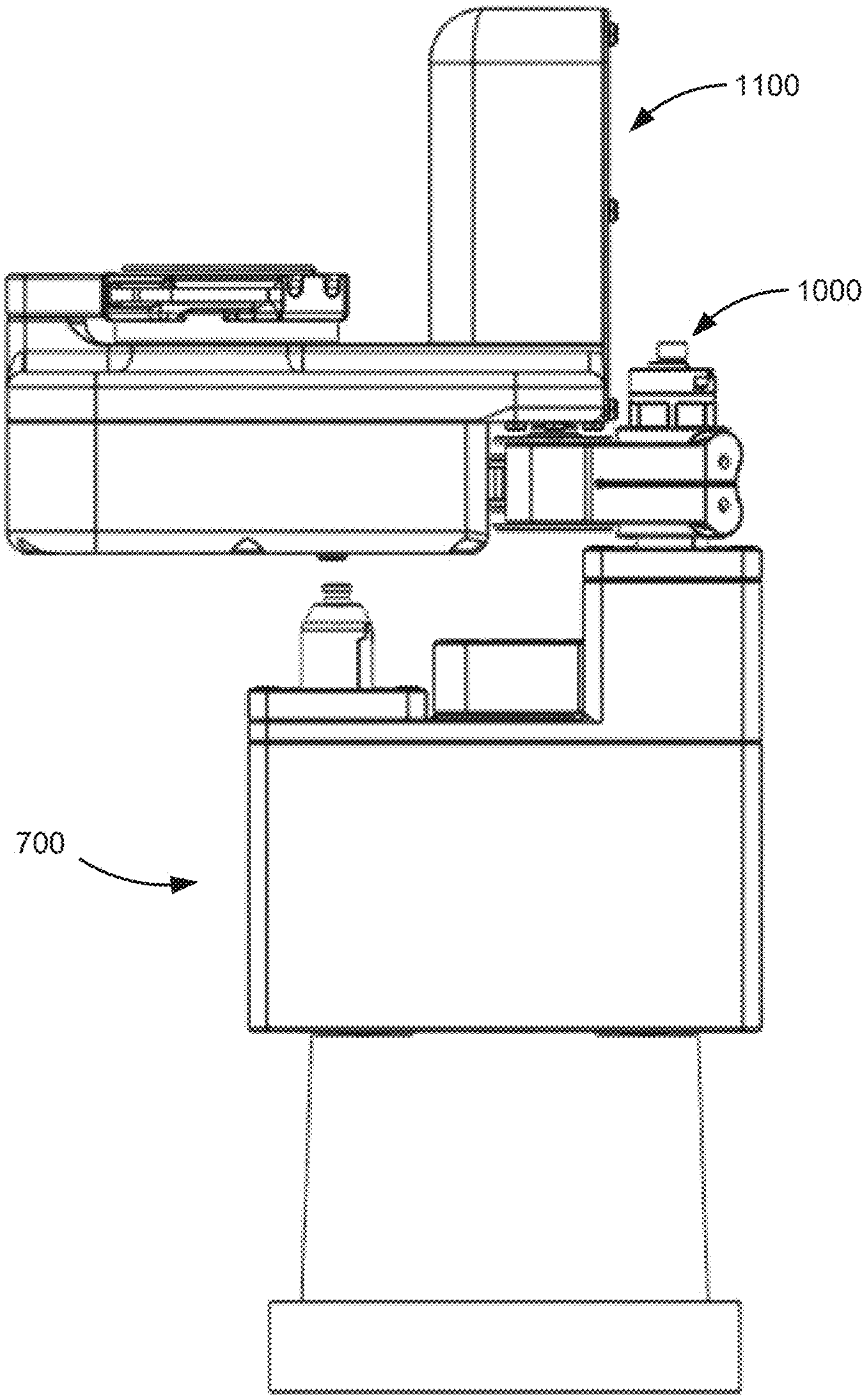
FIG. 12C is a side view illustrating the exemplary process of FIG. 12B.

Referring to FIGS. 12A-12G, there is depicted an exemplary process, generally designated 1200, for connecting two devices in accordance with some exemplary embodiments of the present disclosure. While FIGS. 12A-12C illustrate the use of the exemplary robotic EOAT 1100 for coupling the exemplary apparatus of FIG. 10A with an exemplary port assembly 100 disposed at an exemplary cartridge 700, it should be noted that this is by way of example and it is non-limiting. Other robotic EOAT can be used to couple the exemplary apparatus of FIG. 10A with an exemplary port assembly. Moreover, the exemplary apparatus of FIG. 10A can be coupled with other port assemblies including but not limited to those disclosed herein. Further, a port assembly to be coupled with the exemplary apparatus of FIG. 10A can be a standalone device or a component disposed at other devices including but not limited to the cartridges disclosed herein.

Figure 12D:
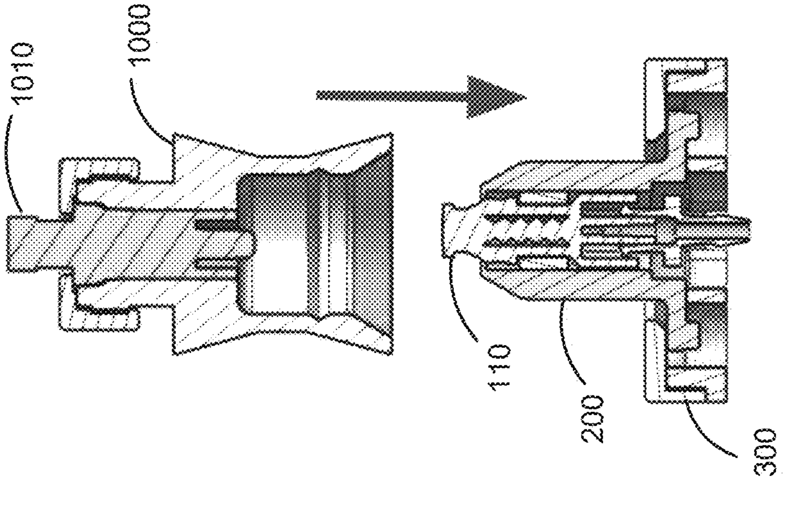
FIGS. 12D, 12E, 12F and 12G are cross-sectional views collectively illustrating an exemplary process that accommodates axial misalignment when connecting the two devices in accordance with some exemplary embodiments of the present disclosure.
Figure 12E:
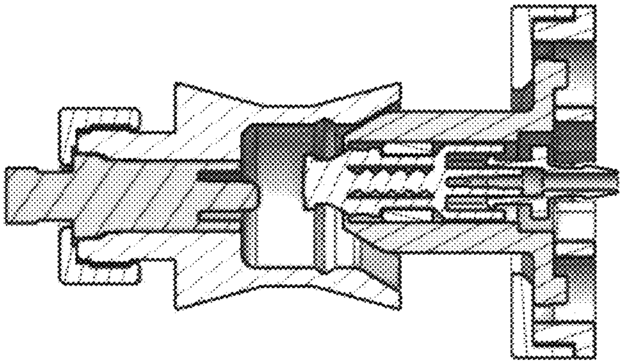
Figure 12F:
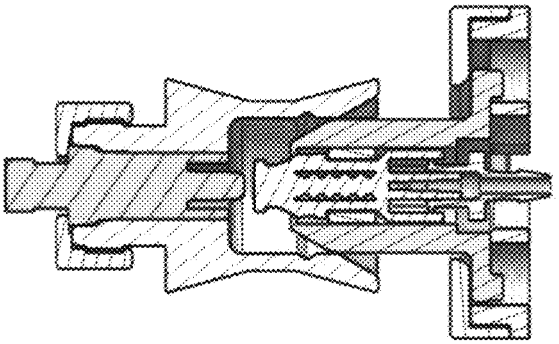
Figure 12G:
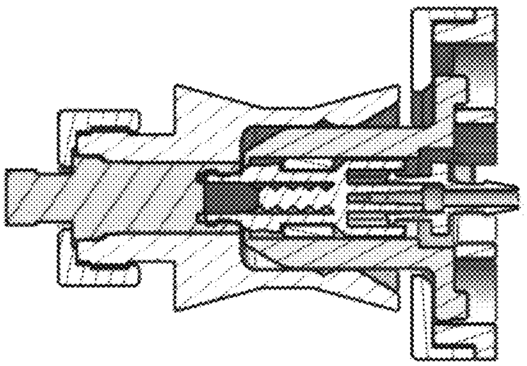

In some embodiments, the port body (e.g., the port body 200) holds a first device (e.g., the device 110), and the coupler 1000 holds a second device (e.g., the second device 1010). The port body and the coupler are moved relative to each other, for instance, by moving the coupler (and thus the second device) toward the port body using the robotic EOAT 1100 as illustrated in FIGS. 12A, 12B and 12D. Unless the port body and the coupler are precisely aligned with each other (which is unusual and difficult in automation), the coupler (e.g., the inner chamfer 1056 of the coupler 1000) will form a first contact with the tip of the port body as illustrated in FIG. 12E. Through this contact, the coupler pushes the port body when moved further toward the port body. Pushed by the coupler and constrained by the retainer (e.g., the retainer 300), the port body moves translationally relative to the retainer, thereby aligning the first device held by the port body with the second device held by the coupler as illustrated in FIG. 12F. Thus, advantageously, this accommodates axial misalignment if necessary when connecting the first and second devices. The first and second devices can then be connected to each other by moving the coupler further toward the port body and/or rotating the coupler relative to the port body as illustrated in FIG. 12G.

The devices and apparatuses of the present disclosure can be used alone or in combination with other devices to implement automated production of cellular engineering targets (e.g., cell therapies) at a biological foundry. Moreover, the components of the devices and the apparatuses (e.g., the port body, the retainer, the coupler, the EOAT) disclosed herein are combinable in any useful number and combination. Further, at least some components of the apparatuses disclosed herein (e.g., the port body, the coupler) can be used alone or in combination with other devices different than the apparatuses disclosed herein.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that includes a computer program mechanism embedded in a non-transitory computer-readable storage medium. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. An apparatus for facilitating automated connection of a first device and a second device, the apparatus comprising:
- a port body comprising:
  - a base;
  - a stem extending from the base;
  - a bore extending from an upper end portion of the stem to a lower end portion of the base and configured for receiving at least a portion of the first device;
  - a tip disposed at a free end portion of the stem and configured for guiding the second device when connecting the second device and the first device; and
  - one or more first anti-rotation members disposed at the base; and
- a retainer comprising:
  - a first retaining member having a first surface;
  - a second retaining member coupled or formed with the first retaining member and having a second surface spaced apart from the first surface of the first retaining member in an axial direction of the port body, wherein the base of the port body is disposed between the first surface of the first retaining member and the second surface of the second retaining member;
  - a first circular or substantially circular through-hole disposed on the first retaining member and having a diameter larger or substantially larger than an outer diameter of the stem to allow the stem of the port body to pass through and to move relative to the first retaining member; and
  - one or more second anti-rotation members disposed at the first retaining member or the second retaining member and coupled with the one or more first anti-rotation members to restrict the port body from rotating relative to the retainer,
- wherein the port body is movable translationally relative to the retainer in a plane substantially perpendicular to the axial direction of the port body.

2. The apparatus of claim 1, wherein the base is circular.

3. The apparatus of claim 1, wherein the base is non-circular.

4. The apparatus of claim 1, wherein the base is substantially planar.

5. The apparatus of claim 4, wherein a thickness of the base equals or substantially equals a distance between the first surface of the first retaining member and the second surface of the second retaining member.

6. The apparatus of claim 1, wherein the first device comprises a fluid connector or an electrical connector.

7. The apparatus of claim 6, wherein the second device comprises a corresponding fluid connector or a corresponding electrical connector.

8. The apparatus of claim 1, wherein at least a portion of the stem is circular or substantially circular.

9. The apparatus of claim 1, wherein the port body further comprises:
- a plurality of internal ribs disposed on an inner surface of the stem and distributed circumferentially, wherein each internal rib in the plurality of internal ribs comprises a surface for abutting an external wall of the first device to secure the first device with the port body.

10. The apparatus of claim 9, wherein each internal rib in at least a subset of the plurality of internal ribs comprises:
- a first rib portion disposed at or adjacent the free end portion of the stem; and
- a second rib portion disposed between the free end portion of the stem and the base.

11. The apparatus of claim 10, wherein the second rib portion contacts with a knurled surface of the first device.

12. The apparatus of claim 9, wherein:
- the stem comprises a first stem member and a second stem member removably coupled with each other.

13. The apparatus of claim 12, wherein:
- at least one internal rib in the plurality of internal ribs is formed on each of the first stem member and the second stem member.

14. The apparatus of claim 12, wherein the first stem member and the second stem member are coupled with each other by snap-fit.

15. The apparatus of claim 12, wherein
- the first stem member comprises a plurality of internal recesses formed on the first stem member; and
- the second stem member comprises a plurality of protrusions, each snap-fitted into a corresponding internal recess in the plurality of internal recesses formed on the first stem member.

16. The apparatus of claim 12, wherein the first stem member is monolithically formed with the base as a single piece.

17. The apparatus of claim 12, wherein the second stem member includes an upper portion, wherein at least a segment of the upper portion is inserted into a groove of the first device, thereby helping to secure the first device on the port body and restrict the first device from moving axially relative to the port body.

18. The apparatus of claim 1, wherein the second retaining member is a component of the second device.

19. The apparatus of claim 1, wherein a second circular or substantially circular through-hole is formed on the second retaining member and concentric with the first circular or substantially circular through-hole formed on the first retaining member.

20. The apparatus of claim 19, wherein one or more slots are formed at the second retaining member, each extending from the second circular or substantially circular through-hole to an edge of the second retaining member to accommodate tubing or cable.

21. The apparatus of claim 1, wherein:

each of the one or more first anti-rotation members is formed adjacent to an outer edge of the base.

22. The apparatus of claim 1, wherein:

each of the one or more first anti-rotation members is a pin formed on the base; and each of the one or more second anti-rotation members is a hole formed on the second retaining member to receive a corresponding pin formed on the base, wherein a size of the hole is larger than a size of the corresponding pin.

23. The apparatus of claim 1, wherein the retainer further comprises:

a rim formed on the first surface of the first retaining member or the second surface of the second retaining member to set a boundary for translational movement of the port body.

24. The apparatus of claim 23, wherein the port body is movable translationally relative to the retainer in the plane substantially perpendicular to the axial direction of the port body within a range defined by (i) a gap between the first circular or substantially circular through-hole formed on the first retaining member and the stem, (ii) a gap between each respective first anti-rotation member in the one or more first anti-rotation members and a corresponding second anti-rotation member in the one or more second anti-rotation members, (iii) a gap between the rim formed on the first surface of the first retaining member or the second surface of the second retaining member and an outer edge of the base of the port body, or (iv) a combination thereof.

25. The apparatus of claim 23, wherein the rim is formed on the second surface of the second retaining member.

26. The apparatus of claim 23, wherein the rim comprises one or more rim segments.

27. The apparatus of claim 23, wherein the rim is in a closed form shape surrounding the base.

28. An apparatus for facilitating automated connection of a first device and a second device, the apparatus comprising:

a port body comprising:

a base;

a stem extending from the base, wherein at least a portion of the stem comprises a circular or substantially circular cross-section;

a bore extending from an upper end portion of the stem to a lower end portion of the base and configured for receiving at least a portion of the first device; and a tip disposed at a free end portion of the stem and configured for guiding the second device when connecting the second device and the first device; and a retainer comprising:

a first retaining member having a first surface;

a second retaining member coupled with the first retaining member and having a second surface spaced apart from the first surface of the first retaining member in an axial direction of the port body, wherein the base of the port body is disposed between the first surface of the first retaining member and the second surface of the second retaining member;

a first circular or substantially circular through-hole formed on the first retaining member and having a diameter larger than an outer diameter of the stem to allow the stem of the port body to pass through and to move relative to the first retaining member; and a rim formed on the first surface of the first retaining member or the second surface of the second retaining member to set a boundary for translational movement of the port body, wherein the port body is movable translationally relative to the retainer in a plane substantially perpendicular to the axial direction of the port body within a range defined by (i) a gap between the first circular or substantially circular through-hole formed on the first retaining member and the stem, (ii) a gap between the rim formed on the first surface of the first retaining member or the second surface of the second retaining member and an outer edge of the base of the port body, or (iii) a combination thereof.

29. An apparatus for facilitating automated connection of a first device and a second device, the apparatus comprising:

a port body comprising:

a base;

a stem extending from the base and comprising a first stem member and a second stem member removably coupled with each other;

a bore extending from an upper end portion of the stem to a lower end portion of the base and configured for receiving at least a portion of the first device;

a tip disposed at a free end portion of the stem and configured for guiding the second device when connecting the second device and the first device; and a plurality of internal ribs formed on the stem and distributed circumferentially for abutting an external wall of the first device to secure the first device with the port body, wherein (i) at least one internal rib in the plurality of internal ribs is formed on each of the first stem member and the second stem member, and (ii) each internal rib in at least a subset of the plurality of internal ribs comprises a first rib portion disposed at or adjacent the free end portion of the stem and a second rib portion disposed between the free end portion of the stem and the base; and a retainer coupled with the port body and configured to restrict the port body from rotating relative to the retainer but allow the port body to move translationally relative to the retainer in a plane substantially perpendicular to an axial direction of the port body.

30. The apparatus of claim 29, wherein the first stem member is monolithically formed with the base as a single piece.

* * * * *